United States Patent [19]

Takatani et al.

[11] Patent Number: 5,244,908
[45] Date of Patent: Sep. 14, 1993

[54] IMIDAZOPYRIDINE DERIVATIVES AND THEIR PHARMACEUTICAL USE

[75] Inventors: Muneo Takatani, Kyoto; Yoshio Kozai, Toyonaka; Kiminori Tomimatsu, Minoo; Yumiko Shibouta, Suita, all of Japan

[73] Assignee: Takeda Chemical Industries, Ltd., Osaka, Japan

[21] Appl. No.: 736,957

[22] Filed: Jul. 30, 1991

[30] Foreign Application Priority Data

| Jul. 30, 1990 | [JP] | Japan | 2-202963 |
| Jul. 30, 1990 | [JP] | Japan | 2-202964 |
| May 27, 1991 | [JP] | Japan | 3-121277 |
| Jun. 12, 1991 | [JP] | Japan | 3-140186 |

[51] Int. Cl.$^5$ .................................. C07D 471/04
[52] U.S. Cl. .................................. 514/300; 546/121
[58] Field of Search .................... 546/121; 514/300

[56] References Cited

U.S. PATENT DOCUMENTS

| 3,509,167 | 4/1970 | Miller | 546/121 |
| 4,096,264 | 6/1978 | Bochis et al. | 424/256 |
| 4,177,274 | 12/1979 | Bochis et al. | 424/256 |
| 4,409,226 | 10/1983 | Bristol et al. | 424/256 |
| 4,831,041 | 5/1989 | Shiokawa et al. | 514/300 |
| 4,833,149 | 5/1989 | Press | 514/300 |
| 4,839,351 | 6/1989 | Nishimura et al. | 514/206 |
| 4,920,129 | 4/1990 | Shiokawa et al. | 514/300 |

FOREIGN PATENT DOCUMENTS

| 0006614 | 1/1980 | European Pat. Off. |
| 0185345 | 6/1986 | European Pat. Off. |
| 0249170 | 12/1987 | European Pat. Off. |
| 2820938 | 11/1978 | Fed. Rep. of Germany |
| 63-10792 | 1/1988 | Japan |
| 1601041 | 10/1981 | United Kingdom |

Primary Examiner—Bernard Dentz
Attorney, Agent, or Firm—Wegner, Cantor, Mueller & Player

[57] ABSTRACT

A calmodulin inhibitory composition containing a compound of the formula (I):

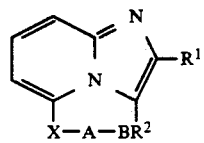

as well as an angiogenesis inhibitory composition containing a compound of the formula (1):

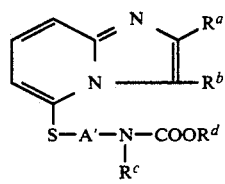

are disclosed.

7 Claims, No Drawings

IMIDAZOPYRIDINE DERIVATIVES AND THEIR PHARMACEUTICAL USE

FIELD OF THE INVENTION

The present invention relates to imidazopyridine derivatives and their use. Particularly, it relates to imidazo[1,2-a]pyridine derivatives which are useful as medicines and a calmodulin inhibitor containing the same.

BACKGROUND OF THE INVENTION

Recently, various cerebrovascular or cardiovascular ischemic diseases have been increased with increasing in population of people of advanced age. At present, as one of medicines for treating these diseases, a calcium channel blocker has been widely used clinically and, therefore, cerebrovascular disorders caused by hypertension are decreased. However, it is said that cardiac ischemic disorders are not decreased, and development of medicines having superior mechanism of activities has been desired.

On the other hand, it has been reported that chlorpromazine having an inhibitory activity to calmodulin which is an intracellular calcium-binding protein is effective for experimental ischemic disorders [G. E. Thomas, S. Levitsky and H. Feinberg, J. Med. Cell Cardiol., 15, 621 (1983); J. I. Dahlager and T. Bilde, Scand. J. Urol Nephrol., 10, 126 (1976); and K. R. Chien, J. Adams, R. G. Pfan and J. L. Farber, Am. J. Pathol., 88, 539 (1977)], and it is also said that calmodulin plays an important role in ischemic disorders [S. W. Schaffer, R. S. Roy and J. M. McMcord, Eur. Heart J., 4 (Suppl. H), 81 (1983)]. However, phenothiadines such as chlorpromazine have a strong central depressant activity and, therefore, there is a drawback in the use thereof as a medicine for circulatory system. Therefore, development of a more superior calmodulin inhibitor has been desired.

There are lot of reports relating to imidazo[1,2-a]pyridine derivatives. However, there is few reports about pharmacological activities of compounds wherein a hydrocarbon having a functional group is bound at the 5-position through S, S(O), S(O)₂, O or N. For example, European Patent Application P87108189.9 reports such compounds as starting materials for synthesis of cephem compounds. Japanese Patent Liad Open Publication Nos. 277393/1987 and 10792/1988 report them as cephem compounds. EP-A-6614 and DE2820938 report them as hypotensors. However, none of them discloses calmodulin inhibitory activity.

OBJECTS OF THE INVENTION

Under these circumstances, the present inventors have intensively studied about activities and synthesis of imidazo[1,2-a]pyridine derivatives wherein a hydrocarbon group having a functional group is bound at the 5-position through S, S(O), S(O)₂, O or N. As a result, certain derivatives having excellent calmodulin inhibitory activities have been found. Thus, the present invention has been completed.

SUMMARY OF THE INVENTION

According to the present invention, there is provided a calmodulin inhibitory composition comprising a compound of the formula (I):

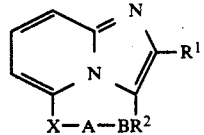

(I)

wherein X is S, S(O), S(O)$_2$, O or NR$^3$ (wherein R$^3$ is a hydrogen or an optionally substituted hydrocarbon group); A is a divalent C$_{1-15}$ hydrocarbon group which may contain an ethereal oxygen at any possible position and may have a substituent at a branched part of the hydrocarbon group; B is an acylated amino group or an acylated or etherified hydroxyl group and the nitrogen atom of the amino group of B may form a ring together with the carbon atom of A or R$^3$; R$^1$ and R$^2$ are the same or different and are hydrogen, an optionally substituted hydrocarbon group, halogen, nitro group, nitroso group, an optionally protected amino group, a lower alkoxycarbonyl group or a lower alkyl carbamoyl group, or a salt thereof (including a solvate).

DETAILED DESCRIPTION OF THE INVENTION

In the formula (I), X is S, S(O), S(O)$_2$, O or NR$^3$ (wherein R$^3$ is a hydrogen or an optionally substituted hydrocarbon group). Preferably, X is S or O. Examples of the optionally substituted hydrocarbon group represented by R$^3$ include a lower alkyl group, an aralkyl group and the like.

Examples of the divalent C$_{1-15}$ hydrocarbon group which may contain an ethereal oxygen at any possible position and may have a substituent at a branched part of the hydrocarbon group represented by A include a group represented by the formula:

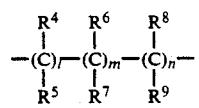

wherein l, m and n are integers of 0 to 5, respectively; R$^4$, R$^5$, R$^6$, R$^7$, R$^8$ and R$^9$ are hydrogen, an optionally substituted lower alkyl, aralkyl or aryl group, respectively; and R$^4$ and R$^5$, R$^6$ and R$^7$ or R$^8$ and R$^9$ may bind together to form a ring, or R$^4$ or R$^6$ may bind together with R$^8$ or R$^9$ to form a ring, a group represented by the formula:

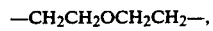

—CH$_2$CH$_2$OCH$_2$CH$_2$—, or a group represented by the formula:

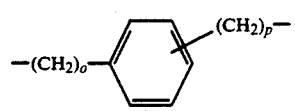

wherein o and p are integers of 0 to 5, respectively.

Examples of the optionally substituted hydrocarbon group represented by R$^1$ and R$^2$ include an optionally substituted lower alkyl, aralkyl or aryl group.

Examples of the acylated amino group represented by B include a group represented by the formula: —NR$^{10}$R$^{11}$ [wherein R$^{10}$ is hydrogen, an optionally substituted alkyl, aralkyl or aryl group, or a group represented by the formula: —CO—$R^{12}$ (wherein $R^{12}$ is hydrogen, or an optionally substituted alkyl, aralkyl or aryl group), —$SO_2R^{13}$ (wherein $R^{13}$ is an optionally substituted alkyl, aralkyl or aryl group), —CO—$NR^{14}R^{15}$ (wherein $R^{14}$ and $R^{15}$ are hydrogen, or an optionally substituted alkyl, aralkyl or aryl group and $R^{14}$ and $R^{15}$ may bind together to form a ring) or —CS—$NR^{14}R^{15}$ (wherein $R^{14}$ and $R^{15}$ are as defined above); $R^{11}$ is a group represented by the formula: —CO—$R^{16}$ (wherein $R^{16}$ is an optionally substituted alkyl, aralkyl or aryl group), —CO—$OR^6$ (wherein $R^{16}$ is as defined above), —$SO_2R^{17}$ (wherein $R^{17}$ is an optionally substituted alkyl, aralkyl or aryl group), —CO—$NR^{14}R^{15}$ (wherein $R^{14}$ and $R^{15}$ are as defined above) or —CS—$NR^{14}R^{15}$ (wherein $R^{14}$ and $R^{15}$ are as defined above); and $R^{10}$ may bind together with $R^3$, $R^4$, $R^6$, $R^8$, $R^{11}$, $R^{16}$ or $R^{17}$ to form a ring]. Examples of the acylated or etherificated hydroxyl group include a group represented by the formula: —O—$R^{18}$ [wherein $R^{18}$ is an optionally substituted alkyl, aralkyl or aryl group, or a group represented by the formula: —CO—$NR^{14}R^{15}$ (wherein $R^{14}$ and $R^{15}$ are as defined above) or —CO—$R^{19}$ (wherein $R^{19}$ is an optionally substituted alkyl, aralkyl or aryl group].

As the lower alkyl group in each substituent in the formula (I), for example, there is a straight or branched alkyl group having 1 to 6 carbon atoms such as methyl, ethyl, propyl, isopropyl, butyl, isobutyl, sec-butyl, tert-butyl, pentyl, hexyl and the like. The alkyl group may have an unsaturated bond and, as the unsaturated alkyl group, for example, there are an alkenyl group having 2 to 6 carbon atoms such as vinyl, allyl, 2-butenyl, 3-butenyl and the like. The lower alkyl group may have 1 to 4 substituents such as halogen, nitro, amino, lower alkylamino, cyclic amino, lower alkoxy, aryloxy, carbamoyl, cyano, hydroxy, carboxy, lower alkoxycarbonyl, lower alkoxycarbamoyl and the like. Examples of halogen include fluorine, bromine, chlorine and iodine.

Examples of the lower alkylamino group as the above substituent include a N-monoalkylamino group of which alkyl moiety has 1 to 6 carbon atoms such as methylamino, ethylamino, propylamino, butylamino and the like, and a N,N-dialkylamino group of which alkyl moiety has 1 to 6 carbon atoms such as dimethylamino, diethylamino, dibutylamino, methylethylamino and the like.

Examples of the cyclic amino group as the above substituent include a 4 to 7 membered cyclic amino group such as N-pyrrolidinyl, piperidino, piperazinyl, morpholino, homopiperazino and the like.

Examples of the lower alkoxy group as the above substitutent include a straight or branched alkoxy group having 1 to 6 carbon atoms such as methoxy, ethoxy, propoxy, isopropoxy, butoxy, pentoxy and the like.

Examples of the aryloxy group as the above substituent include a $C_{6-10}$ aryloxy group such as phenoxy, 1-naphthoxy, 2-naphthoxy group and the like.

Examples of the lower alkoxycarbonyl group as the above substituent include an alkoxycarbonyl group of which alkoxy moiety has 1 to 6 carbon atoms such as methoxycarbonyl, ethoxycarbonyl propoxycarbonyl, butoxycarbonyl and the like.

Examples of the lower alkylcarbamoyl group as the above substituent include a N-monoalkylcarbamoyl group of which alkyl moiety has 1 to 6 carbon atoms such as methylcarbamoyl, ethylcarbamoyl, propylcarbamoyl, butylcarbamoyl and the like, and a N,N-dialkylcarbamoyl group of which alkyl moiety has 1 to 6 carbon atoms such as dimethylcarbamoyl, diethylcarbamoyl, dibutylcarbamoyl, methylethylcarbamoyl and the like.

As the alkyl group in the formula (I), for example, there are a straight or branched alkyl group having 1 to 30, preferably 1 to 10 carbon atoms such as methyl, ethyl, propyl, butyl, pentyl, hexyl, heptyl, octyl, nonyl, decyl, undecyl, tridecyl, tetradecyl, pentadecyl, hexadecyl, heptadecyl, octadecyl, nonadecyl, eicosanyl, heneicosanyl, docosanyl, tricosanyl, tetracosanyl, pentacosanyl, hexacosanyl, heptacosanyl, octacosanyl, nonacosanyl, triacontanyl, farnesyl, dihydrophytyl and the like; a cycloalkyl group having 3 to 8 carbon atoms such as cyclopropyl, cyclobutyl, cyclopentyl, cyclohexyl, cycloheptyl, cyclooctyl and the like; an saturated bicyclic hydrocarbon group formed by binding 5 to 8 membered rings to each other such as norbornyl, bicyclo[2.2.2.]octyl, bicyclo[3.3.1]nonyl, bicyclo[3.3.0]octyl, perhydropentalenyl, perhydroindenyl, perhydroazulenyl, perhydrocyclopentacyclooctenyl, perhydronaphthyl, perhydrobenzocycloheptenyl, perhydrobenzocyclooctenyl, perhydroheptalenyl, perhydrocycloheptacyclooctenyl and the like; and a saturated tricyclic hydrocarbon group formed by binding 5 to 8 membered rings to each other such as adamantylperhydroindacenyl (as, s), perhydroacenaphthylenyl, perhydrophenanthryl, perhydroanthryl and the like.

The above alkyl group may has an unsaturated bond, and examples of the alkyl having an unsaturated bond include an alkenyl group having 2 to 30 carbon atoms such as vinyl, allyl, 9-octadecenyl and the like; a cycloalkenyl group having 5 to 8 carbon atoms such as cyclopentenyl, cyclohexenyl and the like; an unsaturated bicyclic hydrocarbon group such as bicyclo[2.2.2]oct-2-enyl, indanyl (e.g. 1-indanyl, 2-indanyl, etc.), indenyl (e.g. 1H-inden-1-yl, 1H-inden-2-yl, 1H-inden-3-yl, etc.), dihydronaphthyl (e.g. 1,2-dihydro-1-naphthyl, 1,2-dihydro-2-naphthyl, etc.), tetrahydronaphthyl (e.g. 5,6,7,8-tetrahydro-1-naphthyl, 5,6,7,8-tetrahydro-2-naphthyl, etc.), 5H-benzocycloheptenyl (5H-5-benzocycloheptenyl, 5H-8-benzocycloheptenyl, etc.), dihydro-5H-benzocycloheptenyl (e.g. 6,7-dihydro-5H-8-benzohydrocycloheptenyl, etc.), tetrahydrobenzocyclooctenyl (e.g. 5,6,7,8-tetrahydro-9-benzocyclooctenyl, etc.) and the like; and an unsaturated tricyclic hydrocarbon group such as acenaphthenyl (e.g. 1-acenaphthenyl, etc.), tetrahydroanthryl (e.g. 1,2,3,4-tetrahydro-1-anthryl, etc.) and the like.

The above alkyl group having 1 to 30 carbon atoms and alkenyl group having 2 to 30 carbon atoms may be substituted with about 1 to 4, preferably 1 or 2 substituents such as cycloalkyl group having 3 to 8 carbon atoms (e.g., cyclopropyl, etc.), phenyl, naphthyl, halogen (e.g., Br, Cl, etc.), cyano, oxo, lower alkoxy group having 1 to 6 carbon atoms and the like. The phenyl group as the substituent for the alkyl and alkenyl group may be substituted with 1 to 4 substituents such as lower alkyl group having 1 to 6 carbon atoms, lower alkoxy group having 1 to 6 carbon atoms, hydroxy, nitro, halogen and the like.

The cycloalkyl group, bicyclic hydrocarbon group, tricyclic hydrocarbon group and groups having an unsaturated bond thereof included in the alkyl group may be substituted with 1 to 4, preferably 1 or 2 substituents such as lower alkyl group, halogeno lower alkyl group, hydroxy lower alkyl group, acyloxy lower alkyl group, lower alkoxy-lower alkyl group, lower alkoxy group, halogeno lower alkoxy group, lower alkoxycarbonyl-lower alkoxy group, lower alkenyloxy group, aralkyloxy group, lower alkoxy-lower alkoxy group, lower alkoxycarbonyl group, carboxy group, carbamoyl group, N,N-di lower alkylcarbamoyl group, N-lower alkylcarbamoyl group, halogen, cyano, nitro, hydroxy, acyloxy group, amino group, lower alkylsulfonylamino group, acylamino group, lower alkoxycarbonylamino group, acyl group, mercapto, lower alkylthio group, lower alkylsulfinyl group, lower alkylsulfonyl group, oxo and the like. When they are substituted with 2 or more substituents, the substituents may be the same or different.

Examples of the lower alkyl group as the above substituent include an alkyl group having 1 to 6 carbon atoms such as methyl, ethyl, propyl, isopropyl, butyl, isobutyl, sec-butyl, tert-butyl and the like.

As the halogeno lower alkyl group, for example, there is an alkyl group having 1 to 6 carbon atoms which is substituted with 1 to 3 halogen atoms such as trifluoromethyl, fluoromethyl, chloroethyl, fluoroethyl and the like.

As the hydroxy lower alkyl group, for example, there is a hydroxyalkyl group having 1 to 6 carbon atoms such as hydroxymethyl, hydroxyethyl, hydroxypropyl, hydroxybutyl and the like.

As the acyloxy lower alkyl group, for example, there is an alkyl group having 1 to 6 carbon atoms which is substituted with a lower alkanoyloxy or benzoyloxy group having 2 to 6 carbon atoms such as acetoxyethyl, benzoyloxyethyl and the like.

As the lower alkoxy-lower alkyl group, for example, there is an alkyl group having 1 to 6 carbon atoms which is substituted with an alkoxy group having 1 to 6 carbon atoms such as methoxyethyl, ethoxyethyl, propoxyethhyl, butoxyethyl, methoxypropyl, methoxybutyl, ethoxypropyl, ethoxybutyl and the like.

As the lower alkoxy group, for example, there is an alkoxy group having 1 to 6 carbon atoms such as methoxy, ethoxy, propoxy, isopropoxy, butoxy, isobutoxy, sec-butoxy, tert-butoxy and the like.

As the halogeno lower alkoxy group, for example, there is an alkoxy group having 1 to 6 carbon atoms which is substituted with 1 to 3 halogen atoms such as chloroethoxy, fluoroethoxy, difluoroethoxy, trifluoroethoxy, chloropropoxy, chlorobutoxy and the like.

As the lower alkoxycarbonyl-lower alkoxy group, for example, there is an alkoxy group having 1 to 6 carbon atoms which is substituted with an alkoxycarbonyl group of which alkoxy moiety has 1 to 6 carbon atoms such as methoxycarbonylmethoxy, ethoxycarbonylmethoxy, butoxycarbonylmethoxy, methoxycarbonylpropoxy, ethoxycarbonylethoxy and the like.

As the lower alkenyloxy group, for example, there is an alkenyloxy group having 2 to 6 carbon atoms such as vinyloxy, allyloxy, butenyloxy and the like.

As the aralkyloxy group, for example, there is a phenyl lower alkyloxy group of which lower alkyl moiety has 1 to 6 carbon atoms such as benzyloxy, phenethyloxy, 3-phenylpropyloxy, α-methylphenethyloxy, α-methylbenzyloxy, α-ethylbenzyloxy, β-ethylphenethyloxy, β-methylphenethyloxy and the like.

As the lower alkoxy-lower alkoxy group, for example, there is an alkoxy group having 1 to 6 carbon atoms which is substituted with an alkoxy group having 1 to 6 carbon atoms such as ethoxymethoxy, methoxyethoxy, butoxyethoxy, ethoxypropoxy and the like.

As the lower alkoxycarbonyl, for example, there is an alkoxycarbonyl group having 1 to 6 carbon atoms of which alkoxy moiety has 1 to 6 carbon atoms such as methoxycarbonyl, ethoxycarbonyl, propoxycarbonyl, butoxycarbonyl and the like.

As the N,N-di lower alkylcarbamoyl group, for example, there is a N,N-dialkylcarbamoyl group of which alkyl moiety has 1 to 6 carbon atoms such as N,N-dimethylcarbamoyl, N,N-diethylcarbamoyl, N,N-dipropylcarbamoyl, N,N-dibutylcarbamoyl, N-ethyl-N-methylcarbamoyl and the like and a N,N-di lower alkylcarbamoyl group of which alkyl moieties bound together to form 5 or 6 membered ring structure (e.g. N-pyrrolidinylcarbonyl, piperidinocarbonyl, etc.).

As the N-lower alkylcarbamoyl group, for example, there is a N-alkylcarbamoyl group of which alkyl moiety has 1 to 6 carbon atoms such as N-methylcarbamoyl, N-ethylcarbamoyl, N-propylcarbamoyl, N-butylcarbamoyl and the like.

Examples of halogen include chloro, fluoro, bromo, and iodo.

As the acyloxy group, for example, there is an alkanoyloxy group having 2 to 6 carbon atoms such as acetoxy, propanoyloxy, butyloxy, pivaloyloxy and the like, and benzoyloxy group.

As the lower alkylsulfonylamino group, for example, there is an alkylsulfonylamino group having 1 to 6 carbon atoms such as methanesulfonylamino, ethanesulfonylamino and the like.

As the acylamino group, for example, there is an alkanoylamino having 2 to 6 carbon atoms such as acetamide, propanoylamino, butylylamino, pivaloylamino and the like, and benzamide group.

As the lower alkoxycarbonylamino group, for example, there is an alkoxycarbonylamino group of which alkoxy moiety has 1 to 6 carbon atoms such as methoxycarbonylamino, ethoxycarbonylamino, propoxycarbonylamino, butoxycarbonylamino and the like.

As the acyl group, for example, there is an alkanoyl group having 2 to 6 carbon atoms such as acetyl, propanoyl, butylyl, pivaloyl and the like, and benzoyl group.

As the lower alkylthio group, for example, there is an alkylthio group having 1 to 6 carbon atoms such as methylthio, ethylthio, propylthio, butylthio and the like.

As the lower alkylsulfinyl group, for example, there is an alkylsulfinyl group having 1 to 6 carbon atoms such as methylsulfinyl, ethylsulfinyl, propylsulfinyl, butylsulfinyl and the like.

As the lower alkylsulfonyl, for example, there is an alkylsulfonyl having 1 to 6 carbon atoms such as methylsulfonyl, ethylsulfonyl, propylsulfonyl, butylsulfonyl and the like.

As the aralkyl group in the formula (I), for example, there is a phenyl lower alkyl group of which alkyl moiety has 1 to 6 carbon atoms such as benzyl, phenethyl, 3-phenylpropyl, 4-phenylbutyl and the like, and a naphthyl-lower alkyl of which alkyl moiety has 1 to 6 carbon atoms such as (1-naphthyl)methyl, 2-(1-naphthyl)ethyl, 2-(2-naphthyl)ethyl and the like.

The phenyl moiety of the phenyl-lower alkyl group and the naphthyl moiety of the naphthyl lower alkyl group may be substituted with 1 to 4 substituents such as halogen, lower alkyl group, lower alkoxy group, nitro, cyano, hydroxy, lower alkoxycarbonyl group, carbamoyl group, lower alkylcarbamoyl group and the like.

Examples of halogen include fluoro, bromo, chloro and iodo. As the lower alkyl group, for example, there is the same lower alkyl group as that in the above formula (I).

As the lower alkoxy group, for example, there is a straight or branched alkoxy group having 1 to 6 carbon atoms such as methoxy, ethoxy, propoxy, isopropoxy, butoxy, pentoxy and the like.

As the lower alkoxycarbonyl group, for example, there is an alkoxycarbonyl group having 1 to 6 carbon atoms such as methoxycarbonyl, ethoxycarbonyl, propoxycarbonyl, butoxycarbonyl and the like.

As the lower alkylcarbamoyl group, for example, there is a N-alkylcarbamoyl group of which alkyl moiety has 1 to 6 carbon atoms such as methylcarbamoyl, ethylcarbamoyl, propylcarbamoyl, butylcarbamoyl and the like, and a N,N-dialkylcarbamoyl group of which alkyl moiety has 1 to 6 carbon atoms such as dimethylcarbamoyl, diethylcarbamoyl, dibutylcarbamoyl, methylethylcarbamoyl and the like.

As the aryl group in the formula (I), that having 4 to 24 carbon atoms is preferred. For example, there is an aromatic monocyclic, bicyclic or tricyclic hydrocarbon group such as phenyl, 1-naphthyl, 2-naphthyl, phenanthryl, anthryl and the like, and an aromatic monocyclic or bicyclic heterocyclic group such as thienyl, furyl, benzothienyl, benzofuranyl and the like.

The aryl group may substituted with 1 to 4, preferably 1 or 2 substituents such as halogen, lower alkyl group, lower alkoxy group, nitro, cyano, oxo, hydroxy, amino, lower alkoxycarbonyl group, carbamoyl, lower alkylcarbamoyl group and the like.

Examples of halogen include fluoro, bromo, chloro and iodo.

As the lower alkyl group, for example, there is an alkyl group having 1 to 6 carbon atoms, or the lower alkyl group may has an unsaturated bond.

As the lower alkyl group having an unsaturated bond, for example, there is a lower alkenyl group having 2 to 6 carbon atoms.

As the alkyl group having 1 to 6 carbon atoms and the lower alkenyl group having 2 to 6 carbon atoms, for example, there is the same group as the lower alkyl group in the above formula (I).

Examples of the lower alkoxy group include an alkoxy group having 1 to 6 carbon atoms, examples of the lower alkoxycarbonyl group include an alkoxycarbonyl group of which alkoxy moiety has 1 to 6 carbon atoms, and examples of the lower alkylcarbamoyl group include a N-alkylcarbamoyl group of which alkyl moiety has 1 to 6 carbon atoms and a N,N-dialkylcarbamoyl group of which alkyl moiety has about 1 to 6 carbon atoms. Examples of these groups include the same groups as the lower alkoxy, lower alkoxycarbonyl and lower alkylcarbamoyl substitutents of the phenyl moiety in the above aralkyl group.

As the aryl group containing oxo, for example, there are benzoquinolyl, naphthoquinolyl, anthraquinolyl and the like.

Examples of halogen in $R^1$ and $R^2$ include fluoro, bromo, chloro and iodo.

As the lower alkoxycarbonyl group and the lower alkylcarbamoyl group in $R^1$ and $R^2$, for example, there is the same groups as the lower alkoxycarbonyl and lower alkylcarbamoyl substitutents on the phenyl moiety of the above aralkyl group.

Examples of the group wherein $R^{10}$ and $R^3$ are bound together to from a ring include that a group represented by the formula:

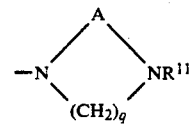

wherein q is 2 or 3, and A and $R^{11}$ are as defined above.

Examples of the group wherein $R^{10}$ is bound with $R^4$, $R^6$ or $R^8$ to form a ring include a group represented by the formula:

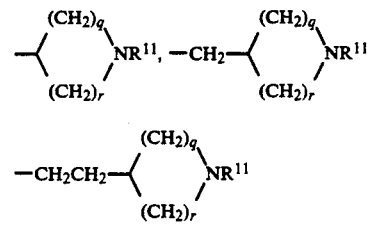

wherein q and r are 2 or 3, respectively; and $R^{11}$ is as defined above.

Examples of the group wherein $-NR^{10}R^{11}$ forms a ring in B include a group represented by the formula:

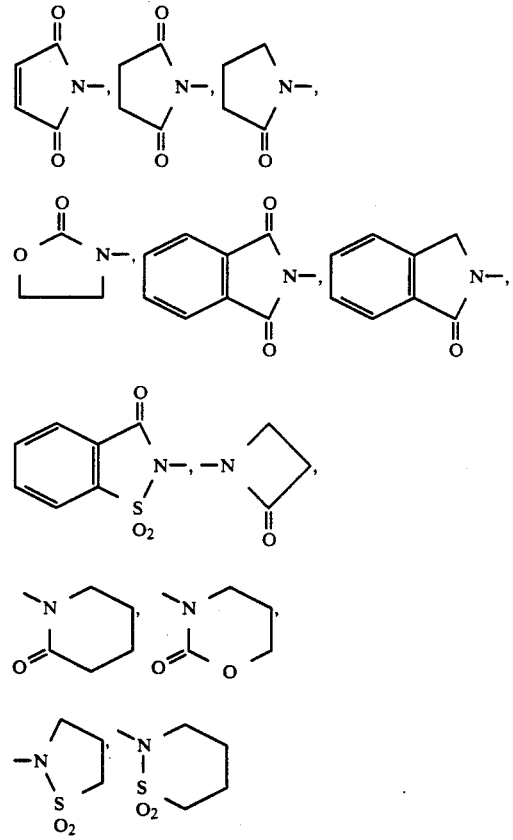

and the like.

The above hetero ring may be substituted with 1 to 4, preferably 1 or 2 substituents such as lower alkyl group, halogeno lower alkyl group, hydroxy lower alkyl group, acyloxy lower alkyl group, lower alkoxy-lower alkyl group, lower alkoxy group, halogeno lower alkoxy group, lower alkoxycarbonyl-lower alkoxy group, lower alkenyloxy group, aralkyloxy group, lower alkoxy-lower alkoxy group, lower alkoxycarbonyl group, carboxy group, carbamoyl group, N,N-di lower alkylcarbamoyl group, N-lower alkylcarbamoyl group, halogen, cyano, nitro, hydroxy, acyloxy group, amino, lower alkylsulfonylamino group, acylamino group, lower alkoxycarbonylamino group, acyl group, mercapto group, lower alkylthio group, lower alkylsulfinyl group, lower alkylsulfonyl group, oxo and the like. When they are substituted with 2 or more substituents, the substituents may be the same or different.

Examples of the lower alkyl group as the above substituent include an alkyl group having 1 to 6 carbon atoms such as methyl, ethyl, propyl, isopropyl, butyl, isobutyl, sec-butyl, tert-butyl and the like.

As the halogeno lower alkyl group, for example, there is an alkyl group having 1 to 6 carbon atoms which is substituted with 1 to 3 halogens such as trifluoromethyl, fluoromethyl, chloromethyl, chloroethyl, fluoroethyl and the like.

As the hydroxy lower alkyl group, for example, there is a hydroxyalkyl group having 1 to 6 carbon atoms such as hydroxymethyl, hydroxyethyl, hydroxypropyl, hydroxybutyl and the like.

As the acyloxy lower alkyl group, for example, there is an alkyl group having 1 to 6 carbon atoms which is substituted with a lower alkanoyl having 2 to 6 carbon atoms or benzoyloxyethyl such as acetoxyethyl, benzoyloxyethyl and the like.

As the lower alkoxy-lower alkyl group, for example, there is an alkyl group having 1 to 6 carbon atoms which is substituted with an alkoxy group having 1 to 6 carbon atoms such as methoxyethyl, ethoxyethyl, propoxyethyl, butoxyethyl, methoxypropyl, methoxybutyl, ethoxypropyl, ethoxybutyl and the like.

As the lower alkoxy group, for example, there is an alkoxy group having 1 to 6 carbon atoms such as methoxy, ethoxy, propoxy, isopropoxy, butoxy, isobutoxy, sec-butoxy, tert-butoxy and the like.

As the halogeno lower alkoxy group, for example, there is an alkoxy group having 1 to 6 carbon atoms which is substituted with 1 to 3 halogen atoms such as chloroethoxy, fluoroethoxy, difluoroethoxy, trifluoroethoxy, chloropropoxy, chlorobutoxy and the like.

As the lower alkoxycarbonyl lower alkoxy group, for example, there is an alkoxy group having 1 to 6 carbon atoms of which alkoxy moiety is substituted with an alkoxycarbonyl group having 1 to 6 carbon atoms such as methoxycarbonylmethoxy, ethoxycarbonylmethoxy, butoxycarbonylmethoxy, methoxycarbonylpropoxy, ethoxycarbonylethoxy and the like.

As the lower alkenyloxy group, for example, there is an alkenyloxy group having 2 to 6 carbon atoms such as vinyloxy, allyloxy, butenyloxy and the like.

As the aralkyloxy group, for example, there is a phenyl lower alkyloxy group of which lower alkyl moiety has 1 to 6 carbon atoms such as benzyloxy, phenethyloxy, 3-phenylpropyloxy α-methylphenethyloxy, α-methylbenzyloxy, α-ethylbenzyloxy, β-ethylphenethyloxy, β-methylphenethyloxy and the like.

As the lower alkoxy-lower alkoxy group, for example, there is an alkoxy group having 1 to 6 carbon atoms which is substituted with an alkoxy group having 1 to 6 carbon atoms such as ethoxymethoxy, methoxyethoxy, butoxyethoxy, ethoxypropoxy and the like.

As the lower alkoxycarbonyl, for example, there is an alkoxycarbonyl group of which alkoxy moiety has 1 to 6 carbon atoms such as methoxycarbonyl, ethoxycarbonyl, propoxycarbonyl, butoxycarbonyl and the like.

As the N,N-di lower alkylcarbamoyl group, for example, there is a N,N-dialykylcarbamoyl group of which alkyl moiety has 1 to 6 carbon atoms such as N,N-dimethylcarbamoyl, N,N-diethylcarbamoyl, N,N-dipropylcarbamoyl, N,N-dibutylcarbamoyl, N-ethyl-N-methylcarbamoyl and the like and a N,N-di lower alkylcarbamoyl group of which alkyl moieties are bound together to form a 5 or 6 membered ring (e.g. N-pyrrolidinylcarbonyl, piperidinocarbonyl, etc.).

As the N-lower alkylcarbamoyl group, for example, there is a N-alkylcarbamoyl group of which alkyl moiety has 1 to 6 carbon atoms such as N-methylcarbamoyl, N-ethylcarbamoyl, N-propylcarbamoyl, N-butylcarbamoyl and the like.

Examples of halogen include chloro, fluoro, bromo and iodo.

As the acyloxy group, for example, there is an alkanoyloxy group having 2 to 6 carbon atoms such as acetoxy, propanoyloxy, butylyloxy, pivaloyloxy and the like, and benzoyloxy group.

As the lower alkylsulfonylamino group, for example, there is an alkylsulfonylamino group having 1 to 6 carbon atoms such as methanesulfonylamino, ethanesulfonylamino and the like.

As the acylamino group, for example, there is an alkanoylamino group having 1 to 6 carbon atoms such as acetamide, propanoylamino, butylylamino, pivaloylamino and the like and benzamide group.

As the lower alkoxycarbonylamino group, for example, there is an alkoxycarbonylamino group of which alkoxy moiety has 1 to 6 carbon atoms such as methoxycarbonylamino, ethoxycarbonylamino, propoxycarbonylamino, butoxycarbonylamino and the like.

As the acyl group, for example, there is an alkanoyl group having 2 to 6 carbon atoms such as acetyl, propanoyl, butylyl, pivaloyl and the like and benzoyl group.

As the lower alkylthio group, for example, there is an alkylthio group having 1 to 6 carbon atoms such as methylthio, ethylthio, propylthio, butylthio and the like.

As the lower alkylsulfinyl group, for example, there is an alkylsulfinyl group having 1 to 6 carbon atoms such as methylsulfinyl, ethylsulfinyl, propylsulfinyl, butylsulfinyl and the like.

As the lower alkylsulfonyl group, for example, there is an alkylsulfonyl group having 1 to 6 carbon atoms such as methylsulfonyl, ethylsulfonyl, propylsulfonyl, butylsulfonyl and the like.

In $-NR^{14}R^{15}$, examples of the group wherein $R^{14}$ and $R^{15}$ together with the adjacent nitrogen atom are bound together to form a ring include a 3 to 8 membered monocyclic heterocyclic group such as 1-aziridinyl, 1-azetidinyl, piperidino, perhydro-1-azepinyl, perhydro-1-azocynyl, morpholino, thiomorpholino, 1-piperazinyl, 3-thiazolidinyl and the like; a condensed bicyclic or bridged bicyclic heterocyclic group such as 1-indolyl, perhydro-1-indolyl, 2-isoindolyl, perhydro-2-isoindolyl, 1,2,3,4-tetrahydro-1-quinolyl, 1,2,3,4-tetarhydro-2-isoquinolyl, perhydro-1-quinolyl, perhydro-2-isoquinolyl, 3-azabicyclo[3.2.2.]non-3-yl and the like; a condensed tricyclic heterocyclic group such as 9-carbazolyl, 10-acridanyl,

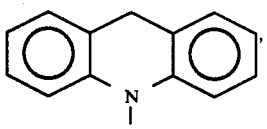

10,11-dihydro-5H-5-dibenz[b,f]azepinyl, 5,6,11,12-tetrahydro-5-dibenz[b,f]azocinyl, 1,2,3,4-tetrahydro-9-carbazolyl, 10-phenoxadinyl, 10-phenothiadinyl and the like.

As the substituent of the above heterocyclic group, for example, there are the same groups as those of $-NR^{10}R^{11}$.

As the optionally protected amino group of $R^1$ and $R^2$, for example, there are amino group, acylamino group and trimethylamino group, and examples of the acyl group include the same groups as those of $R^{11}$.

As the ring formed by connecting $R^4$ with $R^5$, or $R^6$ with $R^7$, or $R^8$ with $R^9$, for example, there are cyclopropyl, cyclobutyl, cyclopentyl, cyclohexyl and the like.

As the ring formed by connecting $R^4$ or $R^6$ with $R^8$ or $R^9$, respectively, for example, there are cyclopropyl, cyclobutyl, cyclopentyl, cyclohexyl and the like.

The compound of the formula (I) forms a salt, for example, an acid addition salt with an inorganic acid such as hydrochloric acid, hydrobromic acid, sulfuric acid, phophoric acid or the like, or an organic acid such as acetic acid, oxalic acid, methanesulfonic acid, maleic acid, fumaric acid, citric acid, tartaric acid, lactic acid or the like.

Examples of a solvent of the solvate include alcohols such as methanol, ethanol, propanol, isopropanol and the like; ketones such as acetone and the like; ethers such as tetrahydrofuran, dioxane and the like.

The compound of the formula (I) may contain an assymetric carbon in the molecule. When two kinds of stereoisomers of R-configuration and S-configuration are present, not only the separated isomers, but also a mixture thereof are included in the scope of the present invention.

Among the compounds represented by the formula (I), the compounds of the formula (I'):

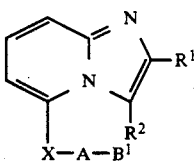

(I')

wherein X, A, $R^1$ and $R^2$ are as defined above and $B^1$ is an amino group acylated by an acyl group derived from carboxylic acid having 2 or more carbon atoms, sulfonic acid, carbamic acid or thiocarbamic acid; the compounds of the formula (I''):

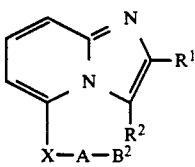

(I'')

wherein X, A, $R^1$ and $R^2$ are as defined above and $B^2$ is an acylated amino group, and the nitrogen atom of the amino group of $B^2$ connects with the carbon atom of A or $R^3$ to form a ring; and the compounds of the formula (I'''):

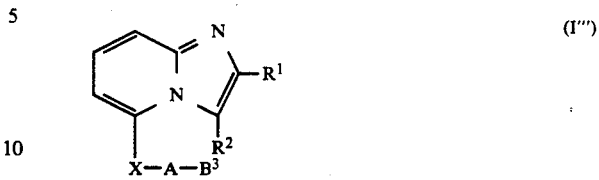

(I''')

wherein X, A, $R^1$ and $R^2$ are as defined above and $B^3$ is a hydroxyl group acylated by an acyl group derived from carboxylic acid or N-hydrocarbon substituted carbamic acid; and acid addition salts and solvates of these compounds have not been described heretofore in the prior art. Therefore, the present invention also provides these novel compounds.

As the amino group acylated by an acyl group derived from carboxylic acid having 2 or more carbon atoms, sulfonic acid, carbamic acid or thiocarbamic acid, there is, for example, a group of the formula: $-NR^{10'}R^{11'}$ [wherein $R^{10'}$ is a hydrogen, or an optionally substituted alkyl, aralkyl or aryl group, or a group of the formula: $-CO-R^{12}$, $-SO_2R^{13}$, $-CO-NR^{14}R^{15}$ or $-CS-N-R^{14}R^{15}$, $R^{11'}$ is a group of the formula: $-CO-R^{16}$, $-SO_2R^{17}$, $-CO-NR^{14}R^{15}$ or $-CS-NR^{14}R^{15}$ (all other symbols are as defined above)]. $R^{10'}$ is preferably hydrogen or, an optionally substituted alkyl, aralkyl or aryl group or, a group of the formula: $-SO_2R^{13}$, $-CO-NR^{14}R^{15}$ or $-CS-NR^{14}R^{15}$. $R^{11'}$ is preferably a group of the formula: $-SO_2R^{17}$, $-CO-NR^{14}R^{15}$ or $-CS-NR^{14}R^{15}$. Particularly, $R^{10'}$ is hydrogen and $R^{11'}$ is a group of the formula: $-SO_2R^{13}$ (all the symbols are as defined above).

Examples of the ring formed by connecting the nitrogen atom of the acylated amino group of $B^2$ with the carbon atom of A or $R^3$ include the above rings formed by connecting $R^{10}$ with $R^3$, $R^4$, $R^6$ or $R^8$.

As the hydroxyl group acylated by an acyl group derived from a carboxylic acid or N-hydrocarbon substituted carbamic acid, there is, for example, a group of the formula: $-O-CO-NR^{15}R^{16}$ or $-O-CO-R^{19}$ (wherein all the symbols are as defined above).

$B^3$ is preferably a group of the formula: $-O-CO-NHR^{16}$ (wherein $R^{16}$ os as defined above).

Among the compounds of the formula (I), those wherein X is S or O, B is (1) an amino group acylated by an acyl group derived from a sulfonic acid, a carbamic acid or thiocarbamic acid, (2) a hydoxyyl group acylated with an acyl group derived from a carboxylic acid or a carbamic acid, or (3) a ring formed by connecting the nitrogen atom of the acylated amino group of B with a carbon atom of A or $R^3$. As the group B, an amino group acylated by an acyl group derived from a sulfonic acid is particularly preferred.

The starting materials or intermediates used for the production of the end products represented by the formula (I) are easily produced by the known processes or the per se known processes.

Imidazo[1,2-a]pyridine derivatives (I) and the salts thereof of the present invention can be synthesized for example, as follows:

(A) When X is S, O or $NR^3$ in the formula (I), a compound of the formula (II):

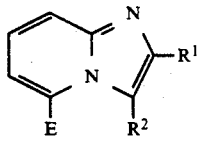

wherein E is halogen such as chloro, bromo or iodo and the other substituents are as defined above, or a salt thereof reacts with a compound of the formula (III):

H—X¹—A—B     (III)

wherein $X^1$ is S, O or $NR^3$ and the other symbols are as defined above, to give the compound (I).

(B) When X is S or O in the formula (I), a compound of the formula (IV):

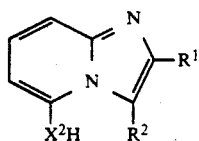

wherein $X^2$ is S or O and the other symbols are as defined above, or a salt thereof reacts with a compound of the formula:

E¹—A—B     (V)

wherein $E^1$ is a leaving group such as halogen (i.e. chloro, bromo, iodo, etc.), toluenesulfonyl group or methanesulfonyl group and the other symbols are as defined above, to give the compound (I).

(C) When B is $-NR^{10}-CO-NR^{14}R^{15}$, $-NR^{10}-CS-NR^{14}R^{15}$ or $-O-CO-NR^{14}R^{15}$ in the formula (I), a compound of the formula (VI):

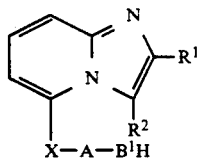

wherein $B^1$ is —O— or $-NR^{10}-$ and the other symbols are as defined above, or a salt thereof reacts with a compound of the formula:

Q¹—NR¹⁴R¹⁵     (VII)

wherein $Q^1$ is PhO—CO—, G—CO— or G—CS— (wherein Ph is a phenyl group and G is halogen such as chloro, etc.) and the other symbols are as defined above, or a salt thereof, to give the compound (I).

(D) When B is $-NR^{10}-CO-NR^{14}R^{15}$, $-NR^{10}-CS-NR^{14}R^{15}$ or $-O-CO-NR^{14}R^{15}$ in the formula (I), a compound of the formula (VIII):

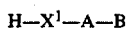

wherein $Q^2$ is OCN—, SCN—, PhO—CO—O—, G—CO—NR¹⁰— or G—CO—O— and the other symbols are as defined above, or a salt thereof reacts with a compound of the formula (IX):

HNR¹⁴R¹⁵     (IX)

wherein all the symbols are as defined above, or a salt thereof, to give the compound (I).

(E) When X is S(O) or S(O)₂ in the formula (I), a compound of the formula (Ia):

wherein all the symbols are as defined above, or a salt thereof reacts with an oxidizing agent, to give the compound (I).

(F) When $R^2$ is halogen such as chloro, bromo, iodo and the like in the formula (I), a compound of the formula (Ib):

wherein all the symbols are as defined above, or a salt thereof reacts with a halogenating agent, to give the compound (I).

(G) When $R^2$ is nitro in the formula (I), a compound of the formula (Ib), or a salt thereof is nitrated to obtain the compound (I).

(H) When $R^2$ is a nitroso group in the formula (I), a compound of the formula (Ib) or a salt thereof is nitrosated to give the compound (I).

(I) When $R^2$ is $CH_2R^{2a}$ (wherein $R^{2a}$ is a lower dialkylamino group or a cyclic amino group) in the formula (I), the compound (I) is prepared by, for example, the following reaction:

(Ib) $\xrightarrow{\text{HCHO, } R^{2a}-H}$ (I)

(J) a compound of the formula (X):

wherein all the symbols are as defined above, or a salt thereof reacts with a compound of the formula (XI):

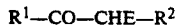 (XI)

wherein the symbols are as defined above, to give the compound (I).

(K) When R$^{11}$ is COR$^{16}$ in the formula (I), a compound of the formula (XII):

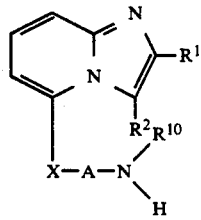 (XII)

wherein the symbols are as defined above, or a salt thereof reacts with a compound of the formula (XIII):

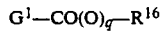 (XIII)

wherein G$^1$ is halogen such as chloro, etc. or R$^{16}$(O)-$_q$—CO—O— (wherein q is 0 or 1) and the other symbols are as defined above, to give the compound (I).

(L) The compound (XII) or a salt thereof is reacted with a compound of the formula (XIV):

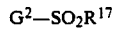 (XIV)

wherein G$^2$ is halogen such as chloro, etc. or R$^{17}$SO$_2$O— and the other symbols are as defined above, to give the compound (I).

(M) When R$^2$ is an amino group in the formula (I), reduction of a compound of the formula (I) wherein R$^2$ is nitro or nitroso, or a salt thereof gives the compound (I) wherein R$^2$ is an amino group. In the case of a protected amino group, the amino group is further acylated or tritylated.

In the above processes A to M, a compound which can forms a salt may be used in the salt form, and examples of such a salt include those as described in the above compound (I). In the following explanation of the processes A to M, a salt of each compound may be included.

The reaction of the compound (II) with the compound (III) in the process A can be conducted at −10° C. to +200° C. in a solvent in the presence of a basic compound such as sodium hydroxide, potassium hydroxide, sodium hydride, potassium carbonate or the like by using 1 equivalent to extremely excessive amount (1 to 10 equivalents) of the compound (III) per 1 equivalent of the compound (II). Examples of the solvent to be used include water; lower alcohols such as methanol, ethanol, propanol and the like; ketones such as acetone, methyl ethyl ketone and the like; ethers such as tetrahydrofuran and the like; and non-aprotic polar solvents such as N,N-dimethylformamide, diethylsulfoxide and the like. The reaction time is normally 1 hour to 2 days, preferably 1 to 8 hours.

The reaction of the compound (IV) with the compound (V) in the process B is conducted under conditions similar to those of the reaction of the compound (II) with the compound (III) in the process A.

The reaction of the compound (VI) with the compound (VII) in the process C is conducted at −10° C. to +150° C. in the absence or presence of a solvent (e.g. ether, toluene, benzene, chloroform, dichloromethane, dioxane, tetrahydrofuran, dimethylformamide, etc.). In order to promote the reaction, a tertiary amine (e.g. triethylamine, pyridine, diethylaminopyridine, N-methylpiperidine, etc.) can be added. The compound (VII) is used in an amount of 1 to 10 equivalents per 1 equivalent of the compound (VI).

The reaction of the compound (VIII) with the compound (IX) in the process D is conducted under conditions similar to those of the reaction of the compound (VI) with the compound (VIII) in the process C. Further, when Q$^2$ is —NCO—, boron trifluoride-ethyl ether (BF$_3$.Et$_2$O) can be added. The reaction time is normally 0.5 to 24 hours, preferably 0.5 to 6 hours.

The oxidation of the compound (Ia) in the process E can be conducted at −30° to +100° C. in the presence of a solvent by using 1 equivalent to extremely excess amount (1 to 10 equivalents) of an oxidizing agent per 1 equivalent of the compound (Ib). Examples of the solvent to be used include water, methanol, ethanol, dichloromethane, chloroform and the like. Examples of the oxidizing agent include m-chloroperbenzoic acid, sodium methaperiodate, hydrogen peroxide and the like. The reaction time is normally 0.5 hours to 2 days, preferably 0.5 to 12 hours.

The reaction of the compound (Ib) with a halogenating agent in the process F can be conducted at −20° to +150° C. in the absence or presence of a solvent by using 1 equivalent to extremely excess amount (1 to 10 equivalents) of the halogenating agent per 1 equivalent of the compound (Ib). Examples of the solvent to be used include halogenated hydrocarbons such as methylene chloride, chloroform, dichloroethane, carbon tetrachloride and the like; acetic acid; propionic acid; and the like. Examples of the halogenating agent include a halogen molecule such as chlorine, bromine and the like; N-halogenosuccinimide such as N-chlorosuccinimide, N-bromosuccinimide and the like. Further, a radical reaction initiator such as benzoyl peroxide or the like can be added in the above reaction. The reaction time is normally 0.5 to 2 hours, preferably 1 to 12 hours.

The nitration of the compound (Ib) in the process (G) can be conducted at −20° to +100° C. in the absence or presence of a solvent by using 1 equivalent to extremely excess amount (1 to 10 equivalents) of a nitrating agent per 1 equivalent of the compound (Ib). Examples of the solvent to be used include acetic acid, acetic anhydride, sulfuric acid and the like. Examples of the nitrating agent include fuming nitric acid, conc. nitric acid, a mixed acid (a mixture of sulfuric acid, fuming nitric acid, phosphoric acid or acetic anhydride and nitric acid) and the like. The reaction time is normally 0.5 to 24 hours, preferably 0.5 to 6 hours.

The nitrosation of the compound (Ib) in the process H can be conducted at −20° to +100° C. in the absence or presence of a solvent by using 1 equivalent to extremely excess amount (1 to 10 equivalents) of a nitrosating agent per 1 equivalent of the compound (Ib). Examples of the solvent to be used include water; lower fatty acids such as acetic acid, propionic acid and the like; ethers such as tetrahydrofuran, dioxane and the like; aprotic polar solvents such as N,N-dimethylformamide, dimethylsulfoxide and the like. Examples of the nitrosating agent include potassium nitrite, sodium nitrite and the like. The reaction is conducted in the presence of an acid such as hydrochloric acid, sulfuric acid, phosphoric acid, acetic acid or the like. The reaction time is normally 0.5 to 24 hours, preferably 0.5 to 6 hours.

Mannich reaction of the compound (Ib) with a lower dialkylamine or a cyclic amine and formalin in the process I can be conducted at −20° to +100° C. in the presence of a solvent by using 1 equivalent to extremely excess amount (1 to 10 equivalents) of a Mannich reagent per 1 equivalent of the compound (Ib). Examples of the solvent to be used include water; lower alcohols such as methanol, ethanol, propanol, isopropanol and the like; lower fatty acids such as acetic acid, propionic acid and the like. The reaction time is normally 30 minutes to 1 day, preferably 1 to 12 hours.

The reaction of the compound (X) with the compound (XI) in the process J can be conducted at 0° to +200° C. in the absence or presence of a solvent by using 1 equivalent to extremely excess amount (1 to 10 equivalents) of the compound (XI) per 1 equivalent of the compound (X). Examples of the solvent to be used include water; lower alcohols such as methanol, ethanol, propanol and the like; ethers such as tetrahydrofuran, dimethoxyethane, dioxane and the like; nitriles such as acetonitrile, propionitrile and the like; aprotic polar solvents such as N,N-dimethylformamide, dimethylsulfoxide and the like. Further, in the above reaction, an inorganic base such as potassium carbonate, sodium bicarbonate or the like, or an organic base such as triethylamine, pyridine, dimethylanilin or the like can be added as an acid-trapping agent. The reaction time is normally 10 minutes to 7 days, preferably 1 hour to 2 days.

The reaction of the compound (XII) with the compound (XIII) in the process K can be conducted at −30° to +200° C. in a solvent in the absence or presence of an inorganic base such as potassium carbonate, sodium bicarbonate or the like or an organic base such as triethylamine, pyridine, dimethylanilin, 1,4-diazabicyclo[2.2.2]octane (DABCO) or the like by using 1 equivalent to extremely excess amount (1 to 10 equivalents) of the compound (XIII) per 1 equivalent of the compound (XII). Examples of the solvent to be used include halogenated hydrocarbons such as methylene chloride, chloroform, dichloroethane and the like; ethers such as diethyl ether, tetrahydrofuran, dimethoxyethane and the like; esters such as methyl acetate, ethyl acetate and the like; aprotic polar solvents such as N,N-dimethylformamide, dimethylsulfoxide and the like. The reaction time is normally 10 minutes to 24 hours, preferably 0.5 to 6 hours.

The reaction of the compound (XII) with the compound (XIV) in the process L is conducted under conditions similar to those of the reaction of the compound (XII) with the compound (XIII) in the process K.

The reduction of the compound (I) wherein $R^2$ is nitro group or nitroso group in the process M can be conducted at −20° to +200° C. in the presence of a solvent by using 1 equivalent to extremely excess amount (1 to 10 equivalents) of a reducing agent per 1 equivalent of the compound (I). Examples of the solvent to be used include water, methanol, ethanol, propanol, isopropanol, acetic acid and the like. Examples of the reducing agent include a mixture of iron and hydrochloric acid or a mixture of zinc and acetic acid. Further, the reaction can be conducted at −20° to +20° C. in the presence of a solvent under normal hydrogen pressure by using a hydrogenating catalyst such as palladium black, palladium carbon, raney nickel or the like.

Examples of the solvent to be used include water, methanol, ethanol, propanol, isopropanol, acetic acid and the like. The reaction time is normally 10 minutes to 24 hours, preferably 0.5 to 6 hours. When the protected amino group is $-NH-CO-NR^{14}R^{15}$ or $-NH-CS-NR^{14}R^{15}$, it can be obtained by reacting the compound of the formula (I) wherein $R^2$ is an amino group with the compound (VII). This reaction is conducted under conditions similar to those of the reactin of the compound (VI) with the compound (VII) in the process C. When the protected amino group is tritylamino group, it can be obtained by reacting the compound of the formula (I) wherein $R^2$ is amino group with trityl chloride. This reaction is a known reaction and it can be conducted according to known conditions.

The compound (II) can be obtained, for example, by the following process.

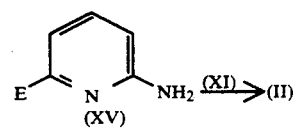

The reaction of the compound (XV) with the compound (XI) is conducted under conditions similar to those of the reaction of the compound (X) with the compound (XI).

The compound (IV) can be obtained, for example, by the following process.

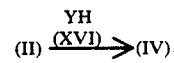

wherein Y is NaS—, KS—, NaO— or KO—.

The reaction of the compound (II) with the compound (XVI) can be conducted at 0° to +250° C. in the presence of a solvent by using 1 equivalent to extremely excess amount of the compound (XVI) per 1 equivalent of the compound (II). Examples of the solvent to be used include water; lower alcohols such as methanol, ethanol, propanol and the like; ethers such as tetrahydrofuran, dimethoxyethane, dioxane and the like; aprotic polar solvents such as N,N-dimethylformamide, dimethylsulfoxide and the like.

The compound (VI) can be obtained, for example, by the following processes.

(i) When X is S or O,

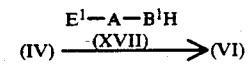

wherein the symbols are as defined above;

(ii) When X is S, O or $NR^3$,

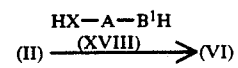

wherein the symbols are as defined above;

(iii) When X is S or O and $B^1$ is $NR^{10}$,

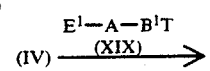

-continued

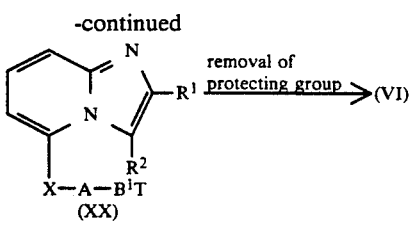

wherein T is an amino protecting group such as benzyloxycarbonyl, tert-tutoxycarbonyl, trifluoroacetyl, trityl, benzyl or the like, and $B^1T$ is phthalimide, the other symbols are as defined above;

(iv) When X s S(O) or $S(O)_2$ and $B^1$ is $NR^{10}$, the compound (XX) is treated with an oxidizing agent, and then any protective group is removed;

(v) When X is S or O and $B^1$ is $NR^{10}$,

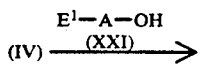

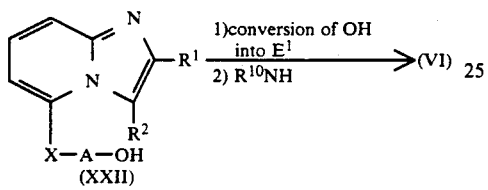

wherein the symbols are as defined above;
(vi) When X is S, O or $NR^3$ and $B^1$ is $NR^{10}$,

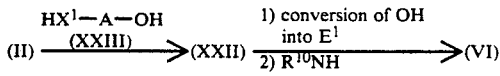

wherein the symbols are as defined above.

The reaction of the compound (IV) with the compound (XVII) in the process (i) is conducted under conditions similar to those of the reaction of the compound (IV) with the compound (V) in the process B.

The reaction of the compound (II) with the compound (XVIII) in the process (ii) is conducted under conditions similar to those of the reaction of the compound (II) with the compound (III) in the process A.

The reaction of the compound (IV) with the compound (XIX) in the process (iii) is conducted under conditions similar to those of the reaction of the compound (IV) with the compound (V) in the process B.

The reaction of the compound (XX) with the oxidizing agent in the process (iv) is conducted under conditiond similar to those of the reaction of the compound (Ia) with an oxidizing agent.

The reaction of the compound (IV) with the compound (XXI) in the process (v) is conducted under conditions similar to those of the reaction of the compound (IV) with the compound (V) in the process B.

The reaction of the compound (II) with the compound (XXIII) in the process (vi) is conducted under conditions similar to those of the reaction of the compound (II) with the compound (III) in the process A.

The conversion of the hydroxyl group of the compound (XXII) in the processes (v) and (vi) into $E^1$ is conducted by, when $E^1$ is haogen, reacting the compound (XXII) with a halogenating agent such as a phophorous halide (e.g., phosphorous trichloride, phosphorous oxychloride, phosphorous pentachloride, phosphorous tribromide, etc.), red phosphorous and halogen, or thionyl chloride and the like. When $E^1$ is toluenesulfonyl group or methanesulfonyloxy group, it can be obtained by the reaction of the compound (XXII) with toluenesulfonyl chloride or methanesulfonyl chloride. The reaction with $R^{10}NH$ which follows the above reaction is conducted at 0° to 200° C. in the absence of any solvent or in a suitable solvent.

All of those reactions are known and they can be conducted according to known conditions.

The compound (VIII) can be obtained, for example, by the following processes.
(i) When $Q^2$ is OCN—,

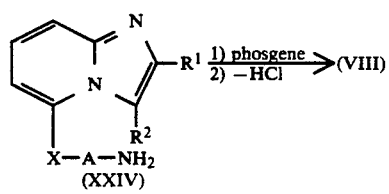

wherein the symbols are as defined above;
(ii) When $Q^2$ is OCN—,

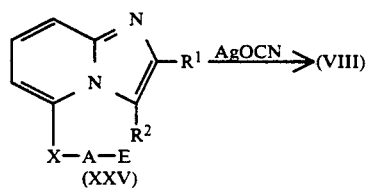

wherein the symbols are as defined above;
(iii) When $Q^2$ is SCH—,

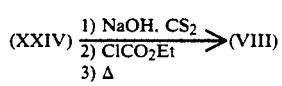

(iv) When $Q^2$ is SCN—,

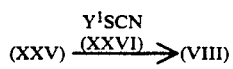

wherein $Y^1$ is Na or K;
(v) When $Q^2$ is PhO—CO—O,

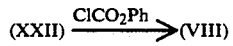

(vi) When $Q^2$ is G—CO—$NR^{10}$,

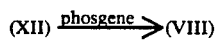

(vii) When $Q^2$ is G—CO—O,

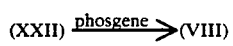

Namely, (i) the compound (XXIV) is reacted with phosgene, and then the reaction product is heated for dehydrochlorination.

(ii) The compound (XXV) is reacted with silver cyanate.

(iii) The compound (XXIV) is reacted with $CS_2$ and further with chlorocarbonate, and then the reaction product is heated.

(iv) The compound (XXV) is reacted with the compound (XXVI).

(v) The compound (XXII) is reacted with phenyl chlorocarbonate.

(vi) The compound (XII) is reacted with phosgene.

(vii) The compound (XXII) is reacted with phosgene.

All the reactions are known and they can be conducted according to known conditions.

All the reactions for removing the above protecting groups are known and they can be conducted according to known conditions.

For example, benzyloxycarbonyl group or benzyl group as the amino protecting group can be removed by a catalytic reduction (reaction temperature: room temperature to $+100°$ C.) in a solvent (e.g., alcohol, acetic acid, water, tetrahydrofuran and a mixed solvent thereof, etc.) in the presence of a catalyst (e.g., palladium on carbon, platinum oxide, etc.).

In the case of trityl group or tert-butoxycarbonyl group, it can be removed at $0°$ to $+150°$ C. in a solvent (e.g., water, alcohol, tetrahydrofuran, dioxane, etc.) in the presence of an acid (e.g., mineral acids such as hydrochloric acid, phophoric acid, sulfuric acid and the like; organic acids such as toluenesulfonic acid, methanesulfonic acid, acetic acid and the like). Trifluoroacetyl group can be readily removed by treating with an alkali (e.g., sodium hydroxide, sodium bicarbonate solution, etc.)

Phthalamide group can be removed by reacting with hydrazine hydrate in a solvent (e.g., methanol, ethanol, etc.).

The starting compounds can be removed from the desired product (I) obtained by the above processes or a salt thereof by the following conventional separation means. Or, a reaction mixture per se may be used as a starting material for the next step without purification.

The isolation and purification of the compound (I) or a salt thereof from the reaction mixture is conducted according to conventional separation means (e.g., extraction, concentration, filtration, recrystallization, column chromatography, thin layer chromatography, etc.).

The compounds (I) of the present invention or salts thereof have calmodulin inhibitory activity and are useful as safe medicines for various diseases of mammal (e.g., human, dog, cat, etc.) such as hypertension, ischemic diseases (e.g., angina, cardiac infarction, arrhythmia, renal failure, etc.), arteriosclerosis, vascular jerk after subarachnoid hemorrhage and inflammatory diseases (e.g., nephritis, asthma, hepatitis, etc.) and the like.

When the compound (I) of the present invention or a salt thereof is used as the above medicines, it can be admixed with a pharmaceutically acceptable carrier, excipient, diluent and administered orally or parenterally in a dosage form such as powder, granules, tablets, capsules, injection and the like. A dosage varies depending upon a particular administration route, conditions to be treated, age and weight of the patient and the like. For example, when it is orally administered to an adult patient, the dosage may be 0.2 to 50 mg/kg/day, preferably 0.5 to 30 mg/kg/day, more preferably 1 to 20 mg/kg/day and it can be administered once to several times in a day.

As described hereinabove, the compounds (I) of the present invention and salts thereof have excellent calmodulin inhibitory activities and are useful as hypotensors and medicines for treating ischemic diseases, antiarteriosclerotic agents, medicines for treating vascular jerk after subarachnoid hemorrhage, anti-inflammatory agents and the like in human and mammal.

The following Reference Examples, Examples, Preparations and Experiments further illustrate the present invention in detail but are not to be construed to limit the scope thereof. In Examples, room temperature means $15°$ to $30°$ C.

Reference Example 1

(1) Synthesis of 2-ethoxycarbonyl-5-chloroimidazo[1,2-a]pyridine

A solution of 2-amino-6-chloropyridine (6.43 g, 50 mmoles) and ethyl bromopyruvate (9.75 g, 50 mmoles) in ethanol (150 ml) was heated at reflux for 4 hours. After the solvent was removed, chloroform was added to the residue, which was washed in turn with saturated sodium bicarbonate and saturated saline, and then dried over anhydrous magnesium sulfate. After the solvent was concentrated, n-hexane was added to the mixture. Then, the crystals precipitated were filtered off and washed with n-hexane to obtain 7.60 g of the desired product (67.6%, pale yellow crystals).

Melting point: $143°-145°$ C.

Elemental analysis for $C_{10}H_9N_2O_2Cl$, Calcd.: C, 53.47; H, 4.04; N, 12.47. Found: C, 53.45; H, 3.99; N, 12.59.

NMR (90MHz, $CDCl_3$) $\delta$: 1.42 (3H, t, J=7Hz), 4.46 (2H, q, J=7Hz), 6.95 (1H, dd, J=7, 1Hz), 7.24 (1H, dd, J=7Hz), 7.67 (1H, d, J=9Hz), 8.36 (1H, s).

According to the same manner as that described in Reference Example 1 (1), the following compounds were obtained.

(2) 5-Chloro-2-methylimidazo[1,2-a]pyridine

NMR (90MHz, $CDCl_3$) $\delta$: 2.47 (3H, s), 6.79 (1H, d, J=7Hz), 7.08 (1H, dd, J=9, 7Hz), 7.47 (1H, d, J=9Hz), 7.51 (1H, s).

(3)
3-Ethoxycarbonyl-5-chloro-2-methylimidazo[1,2-a]pyridine

NMR (90MHz, $CDCl_3$) $\delta$: 1.40 (3H, t, J=7Hz), 2.60 (3H, s), 4.43 (2H, q, J=7Hz), 6.94 (1H, dd, J=1Hz), 7.26 (1H, dd, J=9, 7Hz), 7.54 (1H, dd, J=9, 1Hz).

(4)
2-Ethoxycarbonylmethyl-5-chloroimidazo[1,2-a]pyridine.

NMR (90MHz, $CDCl_3$) $\delta$: 1.28 (3H, t, J=7Hz), 3.87 (2H, s), 4.21 (2H, q, J=7Hz), 6.83 (1H, dd, J=7, 1Hz), 7.12 (1H, dd, J=9, 7Hz), 7.52 (1H, dd, J=9, 1Hz), 7.78 (1H, s).

Reference Example 2

(1) Synthesis of 5-[2-(amino)ethylthio]-2-methylimidazo[1,2-a]pyridine

To a suspension of cysteamine hydrochloride (2.95 g, 26 mmoles) in ethanol (100 ml) was added 60% sodium hydride (oily; 2.08 g, 26 mmoles) with stirring under ice-cooling and the mixture was stirred for 5 minutes. 5-chloro-2-methylimidazo[1,2-a]pyridine (3.33 g, 20 mmoles) was added to the mixture, followed by heating at reflux for 3 hours. After the solvent was distilled off, chloroform was added to the residue which was washed with 1N-NaOH and dried over anhydrous potassium carbonate. After the solvent was distilled off, the residue was purified by column chromatography (eluent: ethyl acetate/ethanol/triethylamine=6:2:1) to obtain 2.2 g of the desired product (53.6%, brown oily product).

NMR (90MHz, CDCl$_3$) δ: 2.25 (2H, br), 2.50 (3H, s), 2.77–3.22 (4H, m), 6.88 (1H, dd, J=7, 1Hz), 7.06 (1H, dd, J=9, 7Hz), 7.46 (1H, d, J=9Hz), 7.62 (1H, s).

According to the same manner as that described in Reference Example 2 (1), the following compounds were obtained.

(2)
5-[2-(Amino)ethylthio]-2-ethoxycarbonylimidazo[1,2-a]pyridine

Elemental analysis for $C_{12}H_{15}N_3O_2S \cdot 0.3H_2O$, Calcd.: C, 53.24; H, 5.81; N, 15.52. Found: C, 53.43; H, 5.61; N, 15.54.

NMR (90MHz, CDCl$_3$) δ: 1.44 (3H, t, J=7Hz), 1.52 (2H, br), 2.83–3.19 (4H, m), 4.46 (2H, q, J=7Hz), 7.00 (1H, dd, J=7, 1Hz), 7.20 (1H, dd, J=9, 7Hz), 7.64 (1H, d, J=9Hz), 8.49 (1H, s).

(3)
5-[2-(Amino)ethylthio]-3-ethoxycarbonyl-2-methylimidazo[1,2-a]pyridine

NMR (90MHz, CDCl$_3$) δ: 1.40 (3H, t, J=7Hz), 1.47 (2H, br), 2.61 (3H, s), 2.81 (2H, m), 3.04 (2H, m), 4.43 (2H, q, J=7Hz), 7.02 (1H, dd, J=7, 1Hz), 7.30 (1H, dd, J=9, 7Hz), 7.48 (1H, dd, J=9, 1Hz).

(4)
5-[2-(Amino)ethylthio]-2-ethoxycarbonylmethylimidazo[1,2-a]pyridine

NMR (90MHz, CDCl$_3$) δ: 1.29 (3H, t, J=7Hz), 1.60 (2H, s), 2.80–3.20 (4H, m), 3.90 (2H, s), 4.21 (2H, q, J=7Hz), 6.90 (1H, dd, J=7, 1Hz), 7.11 (1H, dd, J=9.1Hz), 7.51 (1H, d, J=9Hz), 7.89 (1H, s).

(5) 5-[(4-Piperidyl)thio]imidazo[1,2-a]pyridine

NMR (200MHz, CDCl$_3$) δ: 1.62 (2H, m), 1.93 (2H, m), 2.07 (1H, br), 2.64 (2H, m), 3.12 (2H, m), 3.33 (1H, m), 7.02 (1H, d, J=7Hz), 7.15 (1H, dd, J=9, 7Hz), 7.62 (1H, d, J=9Hz), 7.69 (1H, s), 7.96 (1H, s).

Reference Example 3

(1) Synthesis of 5-[4-(amino)butoxy]imidazo[1,2-a]pyridine

To a suspension of 60% sodium hydride (oily; 1.32 g, 33 mmloes) in DMF (60 ml) was added a solution of 5-chloroimidazo[1,2-a]pyridine (4.59 g, 30.1 mmoles) and 4-aminobutanol (2.68 g, 30.1 mmoles) in DMF (60 ml) at room temperature with stirring and the mixture was stirred at the same temperature for 5 hours. Tert-butyl dicarbonate (9.83 g, 45 mmoles) was added to the reaction solution, which was stirred at room temperature for 13 hours. After the solvent was distilled off, water was added to the residue, which was extracted with ether twice, washed with water and dried over anhydrous magnesium sulfate, and then the solvent was distilled off. The residue was dissolved in methanol (20 ml), followed by the addition of conc. hydrochloric acid (20 ml) and stirring at room temperature for 1 hour. After the solvent was distilled off, chloroform was added to the residue, which was washed with 3N NaOH. After drying over anhydrous potassium carbonate, the solvent was distilled off. The residue was purified by column chromatography (eluent: methanol/chloroform=1:5) to obtain 2.53 g of the desired product (40.9%, light brown oily product).

NMR (200MHz, CDCl$_3$) δ: 1.71 (2H, m), 1.96 (2H, br), 1.97 (2H, m), 2.83 (2H, m), 4.27 (2H, m), 6.03 (1H, d, J=7.2Hz), 7.17 (1H, dd, J=9, 7.2Hz), 7.27 (1H, d, J=9Hz), 7.59 (1H, d, J=1.4Hz), 7.66 (1H, s).

According to the same manner as that described in Reference Example 3 (1), the following compounds were obtained.

(2) 5-[5-(Amino)pentyloxy]imidazo[1,2-a]pyridine

NMR (200MHz, CDCl$_3$) δ: 1.58 (4H, m), 1.66 (2H, br), 1.96 (2H, m), 2.77 (2H, m), 4.25 (2H, t, J=6, 4Hz), 6.02 (1H, d, J=7Hz), 7.16 (1H, dd, J=9, 7Hz), 7.27 (1H, d, J=9Hz), 7.59 (1H; d, J=1.4Hz), 7.66 (1H, s).

(3) 5-[6-(Amino)hexyloxy]imidazo[1,2-a]pyridine

NMR (200MHz, CDCl$_3$) δ: 1.34–1.70 (8H, s), 1.93 (2H, m), 2.73 (2H, m), 4.23 (2H, t, J=6, 4Hz), 6.02 (1H, dd, J=7, 1Hz), 7.16 (1H, dd, J=9, 7Hz), 7.26 (1H, m), 7.59 (1H, d, J=1.2Hz), 7.65 (1H, m).

(4) 5-[2-[1-(Amino)propoxy]]imidazo[1,2-a]pyridine

NMR (200HMz, CDCl$_3$) δ: 1.44 (3H, d, J=6.2Hz), 1.75 (2H, br), 2.96–3.15 (2H, m), 4.63 (1H, m), 6.10 (1H, d, J=7Hz), 7.17 (1H, dd, J=9, 7Hz), 7.27 (1H, d, J=9Hz), 7.59 (1H, d, J=1.4Hz), 7.66 (1H, m).

(5)
5-[2-(Amino)-1-(phenyl)ethoxy]imidazo[1,2-a]pyridine

NMR (200MHz, CDCl$_3$) δ: 1.75 (2H, br), 3.19 (1H, dd, J=14, 4.2Hz). 3.35 (1H, dd, J=14, 7.4Hz), 5.38 (1H, dd, J=7.4, 4.2Hz), 5.89 (1H, d, J=7Hz), 7.01 (1H, dd, J=9, 7Hz), 7.22 (1H, d, J=9Hz), 7.37 (5H, m), 7.64 (1H, d, J=1.2Hz), 7.82 (1H, s).

(6) 5-[(4-Piperidinyl)oxy]imidazo[1,2-a]pyridine

NMR (200MHz, CDCl$_3$) δ: 1.76 (1H, br), 1.87 (2H, m), 2.12 (2H, m), 2.82 (2H, m), 3.18 (2H, m), 4.67 (1H, m), 6.06 (1H, d, J=7.2Hz), 7.17 (1H, dd, J=9, 7.2Hz), 7.27 (1H, d, J=9Hz), 7.60 (1H, d, J=1Hz), 7.69 (1H, s).

Reference Example 4

Synthesis of 5-[2-(phenoxycarbonyloxy)ethylthio]imidazo[1,2-a]pyridine

To a solution of 5-[2-(hydroxy)ethylthio]imidazo[1,2-a]pyridine (5.83 g, 30 mmoles) and pyridine (4.36 ml, 60 mmoles) in methylene chloride (120 ml) was added phenyl chloroformate (7.53 ml, 60 mmoles) with stirring under ice-cooling and the mixture was stirred under ice-cooling for 30 minutes. The reaction solution was washed in turn with an aqueous 5% sodium bicarbonate solution and saturated saline and dried over anhydrous magnesium sulfate, and then the solvent was distilled off. The residue was purified by column chromatography (eluent: ethyl acetate) to obtain 8.61 g of the desired product (91.3%, oily product).

NMR (200MHz, CDCl$_3$) δ: 3.30 (2H, t, J=6.6Hz), 4.42 (2H, t, J=6.6Hz), 7.06–7.45 (8H, m), 7.69 (1H, d, J=1.4Hz), 7.73 (1H, d, J=1.4Hz), 7.92 (1H, m).

Reference Example 5

Synthesis of
5-[2-(methylsulfonyloxy)ethylthio]imidazo[1,2-a]pyridine

To a solution of 5-[2-(hydroxy)ethylthio]imidazo[1,2-a]pyridine (9.71 g, 50 mmoles) and triethylamine (10.5 ml, 75.3 mmoles) in methylene chloride (300 ml) was added methanesulfonyl chloride (4.26 ml, 55 mmoles) with stirring under ice-cooling and the mixture was stirred under ice-cooling for 2 hours. The reaction solution was washed in turn with an aqueous saturated sodium bicarbonate solution and saturated saline and dried over anhydrous magnesium sulfate. Then, the solvent was distilled off to obtain 13.6 g of the desired product (quantitative, brown oily product).

NMR (200MHz, CDCl$_3$) δ: 2.97 (3H, s), 3.28 (2H, t, J=6.4Hz), 4.35 (2H, t, J=6.4Hz), 7.08 (1H, dd, J=7, 1.2Hz), 7.18 (1H, dd, J=8.8, 7Hz), 7.64 (1H, m), 7.73 (1H, d, J=1.4Hz), 7.91 (1H, m).

Reference Example 6

(1) Synthesis of
5-[2-(methylamino)ethylthio]imidazo[1,2-a]pyridine

A solution of 5-[2-(methylsulfonyloxy)ethylthio]imidazo[1,2-a]pyridine (2.18 g, 8 mmoles), triethylamine (2.24 ml, 16 mmoles) and a 40% methylamine-methanol solution (20 ml) in chloroform (20 ml) was heated at reflux for 3 hours. The reaction solution was washed with an aqueous 3N-sodium hydroxide solution and dried over anhydrous magnesium sulfate. After the solvent was distilled off, the residue was purified by column chromatography (eluent: methanol/chloroform=1:10) to obtain 781 mg of the desired product (47.1%, light brown oily product).

NMR (200MHz, CDCl$_3$) δ: 2.31 (1H, br), 2.88 (2H, t, J=6.4Hz), 3.16 (2H, t, J=6.4Hz), 6.94 (1H, dd, J=7, 1Hz), 7.15 (1H, dd, J=9. 7Hz), 7.58 (1H, dd, J=9, 1Hz), 7.69 (1, d, J=1.2Hz), 7.86 (1H, s).

IR (KBr) cm$^{-1}$: 3290, 3105, 2930, 2850, 2790, 1655, 1615, 1530, 1490.

According to the same manner as that described in Reference Example 6 (1), the following compounds were obtained.

(2) 5-[2-(Ethylamino)ethylthio]imidazo[1,2-a]pyridine

NMR (200MHz, CDCl$_3$) δ: 1.11 (3H, t, J=7Hz), 1.88 (1H, br), 2.70 (2H, m), 2.90 (2H, t, J=6.2Hz), 3.15 (2H, t, J=6.2Hz), 6.94 (1H, dd, J=7, 1Hz), 7.16 (1H, dd, J=9, 7Hz), 7.59 (1H, dd, J=9, 1Hz), 7.70 (1H, d, J=1.2Hz), 7.87 (1H, s).

IR (KBr) cm$^{-1}$: 3280, 3105, 2965, 2930, 2890, 2820, 1655, 1620, 1530, 1490.

Reference Example 7

(1) Synthesis of
5-[3-(amino)porpoxy]imidazo[1,2-a]pyridine

To a solution of 5-[3-(tert-butoxycarbonylamino)propoxy]imidazo[1,2-a]pyridine in methanol (10 ml) was added concentrated hydrochloric acid (5 ml) and the mixture was stirred at room temperature for 1 hour. After the solvent was distilled off, chloroform (30 ml) and 3N—NaOH (10 ml) were added to the residue which was extracted with chloroform and dried over anhydrous potassium carbonate. Then, the solvent was distilled off to obtain 687 mg of the desired product (78.7%, pale yellow oily product).

NMR (200MHz, CDCl$_3$) δ: 1.51 (2H, br), 2.07 (2H, m), 3.00 (2H, t, J=6.8Hz), 4.35 (2H, t, J=6.2Hz), 6.06 (2H, d, J=7Hz), 7.17 (1H, dd, J=9, 7Hz), 7.28 (1H, d, J=9Hz), 7.59 (1H, d, J=1.4Hz), 7.65 (1H, s).

According to the same manner as that described in Reference Example 7 (1), the following compounds were obtained.

(2) 5-[2-(Amino)ethoxy]imidazo[1,2-a]pyridine

NMR (200MHz, CDCl$_3$) δ: 1.66 (2H, br), 3.25 (2H, t, J=5.2Hz), 4.28 (2H, t, J=5.2Hz), 6.06 (2H, d, J=7Hz), 7.17 (1H, dd, J=9, 7Hz), 7.29 (1H, d, J=9Hz), 7.61 (1H, d, J=1Hz), 7.68 (1H, s).

(3) 5-[2-(Amino)ethylamino]imidazo[1,2-a]pyridine

NMR (90MHz, CDCl$_3$) δ: 1.70 (2H, br), 3.07 (2H, m), 3.29 (2H, m), 5.17 (1H, br), 5.88 (1H, dd, J=6, 2.5Hz), 7.02–7.30 (2H, m), 7.48 (1H, s), 7.61 (1H, s).

(4) 5-[3-(Amino)propylamino]imidazo[1,2-a]pyridine

NMR (90MHz, CDCl$_3$) δ: 1.57 (2H, br), 1.87 (2H, m), 3.01 (2H, m), 3.39 (2H, m), 5.78 (1H, dd, J=7, 1.5Hz), 6.78 (1H, br), 6.96–7.28 (2H, m), 7.38 (1H, s), 7.59 (1H, s).

Reference Example 8

Synthesis of
5-[3-(amino)propylamino]imidazo[1,2-a]pyridine dihydrochloride

To a suspension of 5-[3-(tert-butoxycarbonylamino)-propylamino]imidazo[1,2-a]pyridine (1.742 g, 6 mmoles) in methylene chloride (40 ml) was added hydrogen chloride-methanol (6 ml) and the mixture was stirred at room temperature for 20 hours. After the solvent was distilled off, ethanol (15 ml) and ether (30 ml) were added to the residue. Then, the crystals precipitated were filtered off and washed in turn with ether and a small amount of ethanol to obtain 1.311 g of the desired product (83.0%, pale yellow crystals).

Elemental analysis for $C_{10}H_{14}N_4O\cdot2HCl\cdot0.2H_2O$, Calcd.: C, 45.02; H, 6.20; N, 21.00. Found: C, 45.15; H, 6.25; N, 21.17.

NMR (90MHz, DMSO-d$_6$) δ: 2.02 (2H, m), 2.95 (2H, m), 3.52 (2H, m), 6.53 (1H, d, J=8Hz), 7.08 (1H, d, J=8.5Hz), 7.79 (1H, dd, J=8.5, 8Hz), 8.12 (1H, d J=2Hz), 8.27 (3H, br), 8.53 (1H, br), 8.78 (1H, d, J=2Hz).

Reference Example 9

Synthesis of
5-[3-(amino)propylthio]imidazo[1,2-a]pyridine

To a mixed solution of 10% potassium hydroxide (69.3 g, 105 mmoles) and dimethylsulfoxide (50 ml) was added S-[3-(amino)propyl]isothiourea.dihydrobromide (8.85 g, 39 mmoles) and the mixture was stirred at room temperature for 1.5 hours. To the reaction solution was added 5-chloroimidazo[1,2-a]pyridine (3.05 g, 20 mmoles), followed by stirring at room temperature for 1.5 hours and additional stirring at 65° C. for 20 hours. Water was added to the reaction solution, which was extracted with chloroform, washed several times with 1N-sodium chloride and dried over anhydrous magnesium sulfate. After the solvent was distilled off to obtain 2.66 g of the desired product (64.3%, pale yellow oily product).

NMR (200MHz, CDCl$_3$) δ: 1.29 (2H, br), 1.80 (2H, m), 2.85 (2H, t, J=6.8Hz), 3.08 (2H, t, J=7.2Hz), 6.91 (1H, dd, J=7, 1Hz), 7.16 (1H, dd, J=9, 7Hz), 7.58 (1H, d, J=9, 1Hz), 7.71 (1H, d, J=1.2Hz), 7.85 (1H, d, J=1.2Hz).

Reference Example 10

According to the same manner as that described in Reference Example 8, the following compounds were obtained.

(1)
5-[2-(Amino)ethylsulfonyl]imidazo[1,2-a]pyridine.dihydrochloride

Melting point: 210°–220° C. (dec.).
Elemental analysis for C$_9$H$_{11}$N$_3$O$_2$S.2HCl. 0.5H$_2$O, Calcd.: C, 35.19; H, 4.59; N, 13.68. Found: C, 35.18; H, 4.49; N, 13.98.

(2)
5-[2-(Amino)ethylsulfinyl]imidazo[1,2-a]pyridine.dihydrochloride

Melting point: 195°–205° C. (dec.).
Elemental analysis for C$_9$H$_{11}$N$_3$OS.2HCl.0.3H$_2$O, Calcd.: C, 37.59; H, 4.77; N, 14.61. Found: C, 37.76; H, 4.77; N, 14.60.

(3)
5-[2-(Amino)ethoxy]imidazo[1,2-a]pyridine.dihydrochloride

Melting point: 209°–220° C. (dec.).
Elemental analysis for C$_9$H$_{11}$N$_3$O.2HCl.H$_2$O, Calcd.: C, 40.31; H, 5.64; N, 15.67. Found: C, 40.20; H, 5.65; N, 15.58.

(4)
5-[4-(Piperidyl)thio]imidazo[1,2-a]pyridine.dihydrochloride

Melting point: 204°–218° C. (dec.).
Elemental analysis for C$_{12}$H$_{15}$N$_3$S.2HCl, Calcd.: C, 47.06; H, 5.59; N, 13.72. Found: C, 47.00; H, 5.63; N, 13.56.

Reference Example 11

Synthesis of
5-[2-(amino)ethylthio]imidazo[1,2-a]pyridine

After a suspension of 5-[2-(amino)ethylthio]imidazo[1,2-a]pyridine.dihydrochloride (13.31 g, 50 mmoles) in chloroform (200 ml) was washed with 3N-sodium hydroxide (50 ml), the aqueous layer was extracted with chloroform, combined the chloroform layer was dried over anhydrous magnesium sulfate. After the solvent was distilled off to obtain 9.63 g of the desired product (99.7%, pale yellow oily product).

NMR (200MHz, CDCl$_3$) δ: 1.67 (2H, br), 2.95 (2H, m), 3.08 (2H, m), 6.95 (1H, d, J=7Hz), 7.15 (1H, dd, J=9.2, 7Hz), 7.59 (1H, d, J=9.2Hz), 7.71 (1H, s), 7.88 (1H, s).

Reference Example 12

Synthesis of
5-[3-(chloro)propylthio]imidazo[1,2-a]pyridine

To a suspension of 5-mercaptoimidazo[1,2-a]pyridine (5.02 g, 33.4 mmoles) and 1-bromo-3-chloropropane (5.26 g, 33.4 mmoles) in ethanol (100 ml) was added triethylamine (4.66 ml, 33.4 mmoles) and the mixture was stirred at room temperature for 17 hours. After the solvent was distilled off, chloroform was added to the residue, which was washed with water and dried over anhydrous magnesium sulfate. After the solvent was distilled off, the residue was purified by column chromatography (eluent: ethyl acetate) to obtain 5.46 g of the desired product (72.0%, light brown oily product).

NMR (200MHz, CDCl$_3$) δ: 2.09 (2H, m), 3.17 (2H, t, J=7Hz), 3.68 (2H, t, J=6Hz), 6.94 (1H, dd, J=7.2, 1Hz), 7.16 (1H, dd, J=9.2, 7.2Hz), 7.60 (1H, m), 7.72 (1H, d, J=1.2Hz), 7.86 (1H, m).

EXAMPLE 1

Synthesis of
5-[2-(methylsulfonylamino)ethylthio]imidazo[1,2-a]pyridine (Compound 1)

To a solution of 5-[2-(amino)ethylthio]imidazo[1,2-a]pyridine (9.63 g, 49.8 mmoles) and triethylamine (7.64 ml) in methylene chloride (150 ml) was added methanesulfonyl chloride (3.85 ml, 49.7 mmoles) with stirring under ice-cooling and was stirred under ice-cooling for 1 hour. The reaction solution was poured into water and stirred. Then, the crystals precipitated were filtered off, washed with water and dried to obtain 10.53 g of the desired product (77.9%, colorless crystals).

Melting point: 130°–131° C.
Elemental analysis (%) for C$_{10}$H$_{13}$N$_3$O$_2$S$_2$, Calcd.: C, 44.26; H, 4.83; N, 15.48. Found: C, 44.05; H, 4.82; N, 15.31.

NMR (90MHz, DMSO-d$_6$) δ: 2.96 (3H, s), 3.22 (4H, s), 7.10 (1H, dd, J=7, 1.5Hz), 7.26 (1H, dd, J=9, 7Hz), 7.31 (1H, br), 7.56 (1H, d, J=9Hz), 7.68 (1H, d, J=1Hz), 7.97 (1H, s).

IR (KBr) cm$^{-1}$: 3450, 3140, 2930, 1620, 1490, 1315, 1155.

EXAMPLE 2

Synthesis of
5-[2-(methylsulfonylamino)ethylthio]imidazo[1,2-a]pyridine.hydrochloride (Compound 2)

A suspension of 5-[2-(methylsulfonylamino)ethylthio]imidazo[1,2-a]pyridine (543 g, 2 mmoles) in methanol (20 ml) was treated with hydrogen chloride-methanol. After the solvent was distilled off, the residue was crystallized from chloroform ether. Then, the crystals thus obtained were washed with ether and dried to obtain 550 mg of the desired product (89.3%, colorless crystals).

Melting point: 154°–160° C.

EXAMPLE 3

(1) Synthesis of
5-[2-(ethylsulfonylamino)ethylthio]imidazo[1,2-a]pyridine (Compound 3)

To a solution of 5-[2-(amino)ethylthio]imidazo[1,2-a]pyridine (1.93 g, 10 mmoles) and triethylamine (1.53 ml, 11 mmoles) in methylene chloride (100 ml) was added ethanesulfonyl chloride (0.95 ml, 10 mmoles) at room temperature with stirring and the mixture was stirred at room temperature for 1 hour. The reaction mixture was washed in turn with an aqueous saturated sodium bicarbonate solution and water and dried over anhydrous magnesium sulfate, and then the solvent was distilled off. The residue was purified by column chromatography (eluent: ethanol/ethyl acetate=1:5) to obtain 2.23 g of the desired product (78.2%, colorless crystals).

Elemental analysis for C$_{11}$H$_{15}$N$_3$O$_2$S$_2$.0.1H$_2$O,

Calcd.: C, 46.01; H, 5.34; N, 14.63.
Found: C, 45.74; H, 5.26; N, 14.36.

NMR (90MHz, DMSO-d$_6$) δ: 1.16 (3H, t, J=7Hz), 2.99 (2H, q, J=7Hz), 3.21 (4H, m), 7.11 (1H, dd, J=7, 1.5Hz), 7.28 (1H, dd, J=8.5, 7Hz), 7.33 (1H, br), 7.59 (1H, d, J=8.5Hz), 7.71 (1H, s), 7.99 (1H, s).

According to the same manner as that described in Example 3 (1), the following compounds were obtained.

(2)
5-[2-(Propylsulfonylamino)ethylthio]imidazo[1,2-a]pyridine (Compound 4)

Elemental analysis for C$_{12}$H$_{17}$N$_3$O$_2$S.0.2H$_2$O, Calcd.: C, 47.57; H, 5.79; N, 13.87. Found: C, 47.62; H, 5.74; N, 14.03.

NMR (200MHz, CDCl$_3$) δ: 1.04 (3H, t, J=7.4Hz), 1.83 (2H, m), 2.98 (2H, m), 3.19 (2H, m), 3.33 (2H, m), 4.93 (1H, br), 7.02 (1H, dd, J=7, 1.2Hz), 7.17 (1H, dd, J=9, 7Hz), 7.63 (1H, m), 7.70 (1H, d, J=1.4Hz), 7.85 (1H, m).

(3)
5-[2-(Isopropylsulfonylamino)ethylthio]imidazo[1,2-a]pyridine (Compound 5)

NMR (200Hz, CDCl$_3$) δ: 1.36 (6H, d, J=6.8Hz), 3.16 (1H, heptet, J=6.8Hz), 3.19 (2H, t, J=6.4Hz), 3.36 (2H, m), 4.80 (1H, br), 7.02 (1H, dd, J=7, 1.2Hz), 7.17 (1H, dd, J=9, 7Hz), 7.62 (1H, d, J=9Hz), 7.70 (1H, s), 7.86 (1H, m).

(4)
5-[2-(Butylsulfonylamino)ethylthio]imidazo[1,2-a]pyridine (Compound 6)

Elemental analysis for C$_{13}$H$_{19}$N$_3$O$_2$S$_2$, Calcd.: C, 49.82; H, 6.11; N, 13.41. Found: C, 49.76; H, 6.15; N, 13.40.

NMR (200Hz, CDCl$_3$) δ: 0.93 (3H, t, J=7.2Hz), 1.43 (2H, m), 1.76 (2H, m), 3.00 (2H, m), 3.19 (2H, m), 3.33 (2H, m), 5.06 (1H, br), 7.01 (1H, dd, J=7, 1.2Hz), 7.16 (1H, dd, J=9, 7Hz), 7.61 (1H, d, J=9Hz), 7.69 (1H, d, J=1.2Hz), 7.84 (1H, m).

(5)
5-[2-(Octylsulfonylamino)ethylthio]imidazo[1,2-a]pyridine (Compound 7)

NMR (90Hz, CDCl$_3$) δ: 0.73-2.00 (15H, m), 2.88-3.52 (6H, m), 6.24 (1H, br), 7.00 (1H, dd, J=7, 1.5Hz), 7.13 (1H, dd, J=9, 7Hz), 7.58 (1H, d, J=9Hz), 7.63 (1H, s), 7.81 (1H, s).

(6)
5-[2-[3-(Chloro)propylsulfonylamino]ethylthio]imidazo[1,2-a]pyridine (Compound 8)

Elemental analysis for C$_{12}$H$_{16}$N$_3$O$_2$S$_2$Cl Calcd.: C, 43.17; H, 4.83; N, 12.59. Found: C, 43.41; H, 4.83; N, 12.47.

NMR (90Hz, CDCl$_3$-DMSO-d$_6$) δ: 2.22 (2H, m), 2.97-3.46 (6H, m), 3.66 (2H, t, J=6.5Hz), 7.07 (1H, dd, J=7.5, 2Hz), 7.19 (1H, dd, J=9, 7.5Hz), 7.26 (1H, br), 7.59 (1H, m), 7.69 (1H, s), 7.90 (1H, s).

(7)
5-[2-(Hexadecylsulfonylamino)ethylthio]imidazo[1,2-a]pyridine (Compound 9)

NMR (200Hz, CDCl$_3$) δ: 0.88 (3H, t, J=6.8), 1.25 (26H, m), 1.78 (2H, m), 3.00 (2H, m), 3.18 (2H, m), 3.33 (2H, m), 4.73 (1H, br), 7.02 (1H, dd, J=7.1Hz), 7.17 (1H, dd, J=9, 7Hz), 7.64 (1H, d, J=9Hz), 7.72 (1H, d, J=1.2Hz), 7.87 (1H, s).

EXAMPLE 4

(1) Synthesis of 3-chloro-5-[2-(methylsulfonylamino)ethylthio]imidazo[1,2-a]pyridine (Compound 10) and 3-chloro-5-[2-(methylsulfonylamino)ethylthio]-2-succinimideimidazo[1,2-a]pyridine (Compound 11)

To a suspension of 5-[2-(methysulfonylamino)ethylthio]imidazo[1,2-a]pyridine (534 mg, 2 mmoles) in chloroform (60 ml) was added N-chlorosuccinimide (267 mg, 2 mmoles) at room temperature with stirring and the mixture was stirred at room temperature for 24 hours. The reaction mixture was washed with water and dried over anhydrous magnesium sulfate, and then the solvent was distilled off. The residue was purified by column chromatography (eluent: ethanol/ethyl acetate=1:10) to obtain 245 mg of the desired product (Compound 10, 40.0%, gray crystals) as Fraction 1.

Elemental analysis for C$_{10}$H$_{12}$N$_3$O$_2$S$_2$Cl, Calcd.: C, 39.28; H, 3.96; N, 13.74. Found: C, 39.47; H, 4.00; N, 13.61.

NMR (90MHz, DMSO-d$_6$) δ: 2.90 (3H, s), 3.22 (4H, m), 7.06 (1H, dd, J=7, 1.5Hz), 7.23 (1H, dd, J=9, 7Hz), 7.53 (1H, dd, J=9, 1.5Hz), 7.66 (1H, s).

As Fraction 2, 96 mg of the desired product (Compound 11, 11.9%, colorless crystals) was obtained.

NMR (90MHz, DMSO-d$_6$) δ: 2.94 (3H, s), 2.97 (4H, s), 3.23 (4H, m), 7.19 (1H, dd, J=7, 2Hz), 7.40 (1H, dd, J=9, 7Hz), 7.59 (1H, dd, J=9, 1.5Hz).

According to the same manner as that described in Example 4 (1), the following compounds were obtained.

(2)
3-Bromo-5-[2-(methylsulfonylamino)ethylthio]imidazo[1,2-a]pyridine (Compound 12)

Elemental analysis for C$_{10}$H$_{12}$N$_3$O$_2$S$_2$Br, Calcd.: C, 34.29; H, 3.45; N, 12.00. Found: C, 34.26; H, 3.45; N, 11.94.

NMR (90MHz, DMSO-d$_6$) δ: 2.90 (3H, s), 3.19 (4H, m), 7.07 (1H, dd, J=7, 1.5Hz), 7.23 (1H, dd, J=9, 7Hz), 7.56 (1H, dd, J=9, 1.5Hz), 7.66 (1H, s).

(3)
3-Iodo-5-[2-(methylsulfonylamino)ethythio]imidazo[1,2-a]pyridine (Compound 13)

NMR (90MHz, DMSO-d$_6$) δ: 2.98 (3H, s), 3.17 (4H, m), 7.07 (1H, dd, J=7, 1.5Hz), 7.24 (1H, dd, J=9, 7Hz), 7.60 (1H, dd, J=9, 1.5 Hz), 7.68 (1H, s).

EXAMPLE 5

Synthesis of 5-[2-(methylsulfonylamino)ethylthio]3-morpholinomethylimidazo[1,2-a]pyridine (Compound 14)

To a solution of 37% formalin (178 mg, 2.2 mmoles) in acetic acid (2 ml) was added morpholin (192 μl, 2.2 mmoles) under ice-cooling with stirring and the mixture was stirred at room temperature for 30 minutes. 5-[2-(methylsulfonylamino)ethylthio] imidazo[1,2-a]pyridine (543 mg, 2 mmoles) was added to the reaction mixture, followed by stirring at 60° C. for 2 hours. After the solvent was distilled off, the residue was dissolved in chloroform (50 ml) and washed with 1N NaOH (10 ml). Then, the aqueous layer was extracted with chloroform (30 ml×3) and the combined chloroform layer was dried over anhydrous magnesium sulfate, and then the solvent was distilled off. The residue was purified by column chromatography (eluent: ethanol/ethyl acetate=1:10→1:5) to obtain 530 mg of the desired product (71.5%, colorless solid).

NMR (90MHz, CDCl$_3$) δ: 2.94 (4H, m), 2.67 (3H, s), 3.27 (4H, m), 3.67 (4H, m), 4.08 (2H, s), 6.62 (1H, br), 6.94 (2H, m), 7.50 (1H, s), 7.57 (1H, dd, J=8.5, 2Hz).

EXAMPLE 6

According to the same manner as that described in Example 4 (1), the following compounds were obtained.

5-[2-(Methylsulfonylamino)ethylthio-3-morpholinomethylimidazo[1,2-a]pyridine dihydrochloride (Compound 15)

NMR (200MHz, DMSO-d$_6$) δ: 2.92 (3H, s), 3.15–4.20 (14H, m), 5.08 (1H, br), 7.44 (1H, m), 7.69 (1H, dd, J=7, 1.4Hz), 7.83 (1H, dd, J=8.7, 7Hz), 7.94 (1H, dd, J=8.8, 1.4Hz), 8.40 (1H, s).

EXAMPLE 7

According to the same manner as that described in Examples 2 and 5, the following compounds were obtained.

3-Dimethylaminomethyl-5-[2-(methylsulfonylamino)ethylthio]imidazo[1,2-a]pyridine.dihydrochloride (Compound 16)

Elemental analysis for C$_{13}$H$_{20}$N$_4$O$_2$S$_2$.2HCl, Calcd.: C, 38.05; H, 5.65; N, 13.65. Found: C, 38.33; H, 5.65; N, 13.61.

NMR (90MHz, DMSO-d$_6$-D$_2$O) δ: 2.95 (9H, s), 3.30 (4H, m), 5.08 (2H, s), 7.68–8.06 (3H, m), 8.43 (1H, s).

EXAMPLE 8

According to the same manner as that described in Example 3, the following compounds were obtained.

(1)
2-Methyl-5-(2-methylsulfonylamino)ethylthio]imidazo[1,2-a]pyridine (Compound 17)

Melting point: 179°–181° C.
Elemental analysis for C$_{11}$H$_{15}$N$_3$O$_2$S$_2$, Calcd.: C, 46.29; H, 5.30; N, 14.72. Found: C, 46.03; H, 5.27; N, 14.39.

(2)
2-Ethoxycarbonylmethyl-5-[2-(methylsulfonylamino)ethylthio]imidazo[1,2-a]pyridine (Compound 18)

NMR (90MHz, CDCl$_3$) δ: 1.29 (3H, t, J=7Hz), 2.95 (3H, s), 3.05–3.48 (4H, m), 3.88 (2H, s), 4.22 (2H, q, J=7Hz), 5.61 (1H, br), 6.97 (1H, dd, J=7, 1.5Hz), 7.12 (1H, dd, J=9, 7Hz), 7.53 (1H, d, J=9Hz), 7.86 (1H, s).

(3)
3-Ethoxycarbonyl-2-methyl-5-[2-(methylsulfonylamino)ethylthio]imidazo[1,2-a]pyridine (Compound 19)

NMR (90MHz, CDCl$_3$) δ; 1.40 (3H, t, J=7Hz), 2.60 (3H, s), 2.85 (3H, s), 3.21 (4H, m), 4.43 (2H, q, J=7Hz), 5.20 (1H, br), 7.07 (1H, dd, J=7, 1.5Hz), 7.33 (1H, dd, J=9, 7Hz), 7.51 (1H, dd, J=9, 1.5Hz).

(4)
2-Ethoxycarbonyl-5-[2-(methylsulfonylamino)ethylthio]imidazo[1,2-a]pyridine (Compound 20)

NMR (90MHz, DMSO-d$_6$) δ: 1.34 (3H, t, J=7Hz), 2.92 (3H, s), 3.26 (4H, m), 4.30 (2H, q, J=7Hz), 7.23 (1H, dd, J=7, 1Hz), 7.30 (1H, br), 7.39 (1H, dd, J=9, 7Hz), 7.64 (1H, d, J=9Hz), 8.43 (1H, s).

EXAMPLE 9

Synthesis of 2-carboxymethyl-5-[2-(methylsulfonylamino)ethylthio]imidazo[1,2-a]pyridine (Compound 21)

To a solution of 2-ethoxycarbonyl-5-[2-(methylsulfonylamino)ethylthio]imidazo[1,2-a]pyridine (1.65 g, 4.62 mmoles) in methanol (5 ml) was added 1N NaOH (6.93 ml, 6.93 mmoles) and the mixture was stirred at room temperature for 2.5 hours. After the reaction mixture was washed with methylene chloride, 1N HCl (17.39 ml, 17.39 mmoles) was added thereto and the solvent was distilled off. Water was added to the residue and the resulting solid was washed with water and dried to obtain 777 mg of the desired product (51.1%, colorless solid).

Elemental analysis for C$_{12}$H$_{15}$N$_3$O$_4$S$_2$ Calcd.: C, 43.76; H, 4.59; N, 12.76. Found: C, 43.68; H, 4.60; N, 12.64.

NMR (200MHz, DMSO-d$_6$) δ: 2.92 (3H, s), 3.24 (4H, s), 3.75 (2H, s), 7.09 (1H, dd, J=7.2, 1Hz), 7.27 (1H, dd, J=9, 7.2Hz), 7.36 (1H, br), 7.48 (1H, d, J=9Hz), 7.86 (1H, s).

EXAMPLE 10

According to the same manner as that described in Examples 2 and 3 (1), the following compounds were obtained.

(1)
5-[2-(N-Methyl-N-methylsulfonylamino)ethylthio]imidazo[1,2-a]pyridine (Compound 22)

NMR (200Hz, CDCl$_3$) δ: 2.82 (3H, s), 2.89 (3H, s), 3.22 (2H, m), 3.40 (2H, m), 7.03 (1H, dd, J=7, 1Hz), 7.19 (1H, dd, J=9, 7Hz), 7.62 (1H, d, J=9Hz), 7.72 (1H, d, J=1.2Hz), 7.86 (1H, s).

(2)
5-[2-(N-methyl-N-methylsulfonylamino)ethylthio]imidazo[1,2-a]pyridine.hydrochloride (Compound 23)

Melting point: 152°–154° C.

(3)
5-[2-(methylsulfonylamino)ethylsulfinyl]imidazo[1,2-a]pyridine (Compound 24)

Elemental analysis for C$_{10}$H$_{13}$N$_3$O$_3$S$_2$.2H$_2$O, Calcd.: C, 41.28; H, 4.64; N, 14.44. Found: C, 41.48; H, 4.57; N, 14.66.

NMR (200Hz, CDCl$_3$-DMSO-d$_6$) δ: 2.98 (3H, s), 3,16–3.33 (1H, m), 3.39–3.76 (3H, m), 7.33–7.47 (3H, m), 7.33–7.84 (2H, m), 8.03 (1H, m).

(4)
5-[2-(Methylsulfonylamino)ethylsulfonyl]imidazo[1,2-a]pyridine (Compound 25)

Elemental analysis for C$_{10}$H$_{13}$N$_3$O$_4$S$_2$, Calcd.: C, 39.59; H, 4.32; N, 13.85. Found: C, 39.31; H, 4.33; N, 13.78.

NMR (200Hz, CDCl$_3$-DMSO-d$_6$) δ: 2.88 (3H, s), 3.45–3.66 (4H, m), 7.40 (1H, d, J=9, 7Hz), 7.71 (1H, dd, J=7, 1.2Hz), 7.85 (1H, d, J=1.2Hz), 7.96 (1H, d, J=9Hz), 8.30 (1H, s).

(5)
5-[2-(Trifluoromethylsulfonylamino)ethylthio]imidazo[1,2-a]pyridine (Compound 26)

NMR (90Hz, DMSO-d$_6$) δ: 3.12–3.52 (4H, m), 7.13 (1H, dd, J=7, 1.5Hz), 7.28 (1H, dd, J=9, 7Hz), 7.61 (1H, d, J=9Hz), 7.71 (1H, d, J=1.5Hz), 8.02 (1H, s).

(6)
5-[3-(Methylsulfonylamino)propylthio]imidazo[1,2-a]pyridine (Compound 27)

Elemental analysis for C$_{11}$H$_{15}$N$_3$O$_2$S$_2$, Calcd.: C, 46.29; H, 5.30; N, 14.72. Found: C, 46.35; H, 5.34; N, 14.71.

NMR (90Hz, CDCl$_3$) δ: 1.90 (2H, m), 2.93 (2H, s), 3.07 (2H, m), 3.27 (2H, m), 5.54 (1H, br), 6.90 (1H, dd, J=7, 1Hz), 7.11 (1H, dd, J=9, 7Hz), 7.57 (1H, d, J=9Hz), 7.65 (1H, d, J=1.5Hz), 7.82 (1H, s).

(7)
5-[3-(Trifluoromethylsulfonylamino)propylthio]imidazo[1,2-a]pyridine (Compound 28)

Elemental analysis for C$_{11}$H$_{12}$N$_3$O$_2$S$_2$F$_3$, Calcd.: C, 38.93; H, 3.56; N, 12.38. Found: C, 38.91; H, 3.64; N, 12.27.

NMR (200Hz, CDCl$_3$-DMSO-d$_6$) δ: 1.91 (2H, m), 3.09 (2H, t, J=7.2Hz), 3.36 (2H, t, J=6.2Hz), 6.97 (1H, dd, J=7, 1Hz), 7.19 (1H, dd, J=9, 7Hz), 7.58 (1H, dd, J=9, 1Hz), 7.70 (1H, d, J=1.2Hz), 7.88 (1H, s).

(8)
5-[1-(Methylsulfonyl)-4-piperidylthio]imidazo[1,2-a]pyridine.hydrochloride (Compound 29)

Melting point: 191°–200° C.

NMR (200Hz, CDCl$_3$) of the free compound δ: 1.70–2.13 (4H, m), 2.79 (3H s), 2.90 (2H, m), 3.35 (1H, m), 3.69 (2H, m), 7.05 (1H, dd, J=7, 1.2Hz), 7.17 (1H, dd, J=8.8, 7Hz), 7.67 (1H, d, J=8.8Hz), 7.71 (1H, d, J=1.2Hz), 7.96 (1H, s).

(9)
5-[2-(Phenylsulfonylamino)ethylthio]imidazo[1,2-a]pyridine (Compound 30)

Elemental analysis for C$_{15}$H$_{15}$N$_3$O$_2$S$_2$, Calcd.: C, 54.03; H, 4.53; N, 12.60. Found: C, 53.88; H, 4.53; N, 12.43.

NMR (200Hz, CDCl$_3$) δ: 3.01–3.23 (4H, m), 5.05 (1H, br), 6.84 (1H, d, J=7Hz), 7.08 (1H, dd, J=9, 7Hz), 7.41–7.63 (4H, m), 7.68 (1H, d, J=1.4Hz), 7.75–7.83 (3H, m).

(10)
5-[2-[4-(Methyl)phenylsulfonylamino]ethylthio]imidazo[1,2-a]pyridine (Compound 31)

Elemental analysis for C$_{16}$H$_{17}$N$_3$O$_2$S$_2$.0.5H$_2$O, Calcd.: C, 53.91; H, 5.09; N, 11.79. Found: C, 54.13; H, 4.94; N, 11.57.

NMR (90Hz, CDCl$_3$-DMSO-d$_6$) δ: 2.39 (3H, s), 3.16 (4H, m), 6.90–7.33 (3H, m), 7.47–7.90 (7H, m).

(11)
5-[2-[4-(Acetamido)phenylsulfonylamino]ethylthio]imidazo[1,2-a]pyridine (Compound 32)

Elemental analysis for C$_{17}$H$_{18}$N$_4$O$_3$S$_2$.1H$_2$O, Calcd.: C, 49.98; H, 4.93; N, 13.72. Found: C, 50.16; H, 4.60; N, 13.60.

NMR (200Hz, DMSO-d$_6$) δ: 2.09 (3H, s), 2.98 (2H, m), 3.13 (2H, m), 6.99 (1H, dd, J=1Hz), 7.23 (1H, dd, J=9, 7Hz), 7.52–7.77 (6H, m), 7.83 (1H, br), 7.90 (1H, m).

(12)
5-[2-[4-(Acetamido)phenylsulfonylamino]ethylthio]imidazo[1,2-a]pyridine.hydrochloride (Compound 33)

Melting point: 126°–130° C.

(13)
5-[2-[4-(Chloro)phenylsulfonylamino]ethylthio]imidazo[1,2-a]pyridine (Compound 34)

Elemental analysis for C$_{15}$H$_{14}$N$_3$O$_2$S$_2$Cl.0.5H$_2$O, Calcd.: C, 47.80; H, 4.01; N, 11.15. Found: C, 48.03; H, 3.63; N, 11.18.

NMR (200Hz, CDCl$_3$-DMSO-d$_6$) δ: 3.68 (4H, m), 6.98 (1H, d, J=7Hz), 7.18 (1H, dd, J=9, 7Hz), 7.44 (2H, m), 7.56 (1H, d, J=9Hz), 7.67 (1H, d, 1.2Hz), 7.74 (2H, m), 7.83 (1H, s), 7.87 (1H, br).

(14)
5-[2-[4-(Fluoro)phenylsulfonylamino]ethylthio]imidazo[1,2-a]pyridine (Compound 35)

Elemental analysis for C$_{15}$H$_{14}$N$_3$O$_2$S$_2$F Calcd.: C, 51.27; H, 4.02; N, 11.96. Found: C, 51.16; H, 4.05; N, 12.05.

NMR (200Hz, CDCl$_3$-DMSO-d$_6$) δ: 3.08 (4H, m), 6.95 (1H, dd, J=7, 1Hz), 7.07–7.20 (3H, m), 7.48 (1H, br), 7.58 (1H, d, J=9Hz), 7.68 (1H, d, J=1.2Hz), 7.77–7.86 (3H, m).

(15)
5-[2-[4-(Methoxy)phenylsulfonylamino]ethylthio]imidazo[1,2-a]pyridine (Compound 36)

Elemental analysis for C$_{16}$H$_{17}$N$_3$O$_3$S$_2$.0.3H$_2$O, Calcd.: C, 52.10; H, 4.81; N, 11.39. Found: C, 52.25; H, 4.73; N, 11.47.

NMR (200Hz, CDCl$_3$-DMSO-d$_6$) δ: 3.07 (4H, m), 3.86 (3H, s), 6.86–6.97 (3H, m), 7.15 (1H, dd, J=9, 7Hz), 7.20 (1H, br), 7.57 (1H, d, J=9Hz), 7.64–7.76 (3H, m), 7.81 (1H, s).

(16)
5-[2-[2,4,5-(Trichloro)phenylsulfonylamino]ethylthio]imidazo[1,2-a]pyridine (Compound 37)

Elemental analysis for C$_{15}$H$_{12}$N$_3$O$_2$S$_2$CL$_3$.0.5H$_2$O, Calcd.: C, 40.42; H, 2.94; N, 9.43. Found: C, 40.65; H, 2.74; N, 9.50.

NMR (200Hz, CDCl$_3$-DMSO-d$_6$) δ: 3.07–3.25 (4H, m), 6.95 (1H, dd, J=7, 1Hz), 7.16 (1H, dd, J=9, 7Hz), 7.57 (1H, d, J=9Hz), 7.59 (1H, s), 8.07 (1H, s).

(17)
5-[2-[2,4,6-(Trimethyl)phenylsulfonylamino]ethylthio]imidazo[1,2-a]pyridine (Compound 38)

Elemental analysis for C$_{18}$H$_{21}$N$_3$O$_2$S$_2$, Calcd.: C, 57.57; H, 5.65; N, 11.19. Found: C, 57.32; H, 5.65; N, 11.09.

NMR (200Hz, CDCl$_3$) δ: 2.30 (3H, s), 2.58 (6H, s), 2.98–3.20 (4H, m), 5.00 (1H, br), 6.81 (1H, d, J=7Hz), 6.92 (2H, s), 7.08 (1H, dd, J=9, 7Hz), 7.60 (1H, d, J=9Hz), 7.68 (1H, s), 7.77 (1H, s).

(18)
5-[2-[2,4,6-(Triisopropyl)phenylsulfonylamino]ethylthio]imidazo[1,2-a]pyridine (Compound 39)

Elemental analysis for C$_{24}$H$_{33}$N$_3$O$_2$S$_2$, Calcd.: C, 62.71; H, 7.24; N, 9.14. Found: C, 62.65; H, 7.15; N, 9.07.

NMR (200Hz, CDCl$_3$) δ: 1.24 (12H, d, J=6.8Hz), 1.26 (6H, d, J=7Hz), 2.94 (1H, heptet, J=7Hz), 3.06–3.25 (4H, m), 4.10 (2H, heptet, J=6.8Hz), 4.90 (1H, br), 6.83 (1H, dd, J=7, 1Hz), 7.08 (1H, dd, J=9, 7Hz), 7.59 (1H, d, J=9Hz), 7.68 (1H, d, J=1.2Hz), 7.80 (1H, m).

(19)

5-[2-[(2-Thienyl)sulfonylamino]ethylthio]imidazo[1,2-a]pyridine (Compound 40)

Elemental analysis for C$_{13}$H$_{13}$N$_3$O$_2$S$_3$, Calcd.: C, 46.00; H, 3.86; N, 12.38. Found: C, 45.71; H, 3.88; N, 12.30.

NMR (200Hz, DMSO-d$_6$) δ: 3.03–3.20 (4H, m), 7.04 (1H, dd, J=7, 1Hz), 7.12 (1H, m), 7.26 (1H, dd, J=9, 7Hz), 7.50–7.61 (2H, m), 7.69 (1H, d, J=1.4Hz), 7.89 (1H, m), 7.93 (1H, m), 8.16 (1H, br).

(20)

5-[2-[(2-Thienyl)sulfonylamino]ethylthio]imidazo[1,2-a]pyridine hydrochloride (Compound 41)

Melting point: 140°–143° C.

Elemental analysis for C$_{13}$H$_{13}$N$_3$O$_2$S$_3$.HCl, Calcd.: C, 41.54; H, 3.75; N, 11.18. Found: C, 41.25; H, 3.80; N, 11.05.

(21)

5-[2-[(1-Naphthyl)sulfonylamino]ethylthio]imidazo[1,2-a]pyridine (Compound 42)

Elemental analysis for C$_{19}$H$_{17}$N$_3$O$_2$S$_2$, Calcd.: C, 59.51; H, 4.47; N, 10.96. Found: C, 59.73; H, 4.61; N, 10.77.

NMR (200Hz, CDCl$_3$) δ: 2.97 (2H, m), 3.07 (2H, m), 5.55 (1H, br), 6.56 (1H, dd, J=7, 1Hz), 6.92 (1H, dd, J=9, 7Hz), 7.44–7.72 (6H, m), 7.96 (1H, m), 8.06 (1H, d, J=8.2Hz), 8.20 (1H, dd, J=7.4, 1.2Hz), 8.64 (1H, m).

(22)

5-[2-[(1-Naphthyl)sulfonylamino]ethylthio]imidazo[1,2-a]pyridine hydrochloride (Compound 43)

Melting point: 179°–185° C.

(23)

5-[2-[(2-Naphthyl)sulfonylamino]ethylthio]imidazo[1,2-a]pyridine (Compound 44)

Melting point: 179°–185° C.

Elemental analysis for C$_{19}$H$_{17}$N$_3$O$_2$S$_2$.0.2H$_2$O, Calcd.: C, 58.95; H, 4.53; N, 10.86. Found: C, 59.15; H, 4.78; N, 10.55.

NMR (200Hz, CDCl$_3$) δ: 3.07 (2H, m), 3.20 (2H, m), 5.31 (1H, br), 6.74 (1H, dd, J=7, 1Hz), 6.89 (1H, dd, J=9, 7Hz), 7.51 (1H, d, J=9Hz), 7.58–7.85 (5H, m), 7.88–7.97 (3H, m), 8.39 (1H, d, J=1.6Hz).

(24)

5-[2-[(2-Naphthyl)sulfonylamino]ethylthio]imidazo[1,2-a]pyridine.hydrochloride (Compound 45)

Melting point: 170°–175° C.

(25)

5-[2-[(8-Quinolyl)sulfonylamino]ethylthio]imidazo[1,2-a]pyridine (Compound 46)

Elemental analysis for C$_{18}$H$_{16}$N$_4$O$_2$S$_2$ Calcd.: C, 56.23; H, 4.19; N, 14.57. Found: C, 56.39; H, 4.23; N, 14.69.

NMR (200Hz, CDCl$_3$) δ: 3.00–3.22 (4H, m), 6.65 (1H, dd, J=7, 1Hz), 6.81 (1H, br), 6.97 (1H, dd, J=9, 7Hz), 7.47–7.74 (5H, m), 8.06 (1H, dd, J=8.4, 1.4Hz), 8.26 (1H, dd, J=8.4, 1.8Hz), 8.40 (1H, dd, J=7.2, 1.4Hz), 8.95 (1H, dd, J=4.2, 1.8Hz).

(26)

5-[2-[8-(Quinolyl)sulfonylamino]ethylthioimidazo[1,2-a]pyridine.hydrochloride (Compound 47)

Melting point: 190°–196° C.

(27)

5-[2-[5-(Dimethylamino)-(1-naphthylsulfonylamino)]ethylthio]imidazo[1,2-a]pyridine (Compound 48)

NMR (200Hz, CDCl$_3$) δ: 2.90 (6H, s), 2.93–3.12 (4H, m), 5.46 (1H, br), 6.56 (1H, dd, J=7, 1Hz), 6.92 (1H, dd, J=9, 7Hz), 7.19 (1H, d, J=7.6Hz), 7.43–7.63 (4H, m), 7.67 (1H, s), 8.18 (1H, dd, J=7.4, 1.2Hz), 8.27 (1H, d, J=8.6Hz), 8.53 (1H, d, J=8.6Hz).

(28)

5-[2-[(E)-Styrylsulfonylamino]ethylthio]imidazo[1,2-a]pyridine (Compound 49)

Elemental analysis for C$_{17}$H$_{17}$N$_3$O$_2$S$_2$, Calcd.: C, 56.80; H, 4.77; N, 11.69. Found: C, 56.95; H, 4.84; N, 11.62.

NMR (200Hz, CDCl$_3$) δ: 3.14–3.34 (4H, m), 4.95 (1H, br), 6.70 (1H, d, J=15.4Hz), 6.98 (1H, dd, J=7, 1Hz), 7.09 (1H, dd, J=9, 7Hz), 7.43 (5H, m), 7.46 (1H, d, J=15.4Hz), 7.59 (1H, d, J=9Hz), 7.68 (1H, d, J=1.4Hz), 7.84 (1H, s).

(29)

5-[2-[N,N-di-(E)-Styrylsulfonylamino]ethylthio]imidazo[1,2-a]pyridine (Compound 50)

Elemental analysis for C$_{25}$H$_{23}$N$_3$O$_4$S$_3$, Calcd.: C, 57.12; H, 4.41; N, 7.99. Found: C, 57.07; H, 4.48; N, 7.81.

NMR (200Hz, CDCl$_3$) δ: 3.33 (2H, m), 3.91 (2H, m), 7.05 (1H, dd, J=7, 1Hz), 7.12 (2H, d, J=15.4Hz), 7.18 (1H, dd, J=8.8, 7Hz), 7.38–7.56 (12H, m), 7.61 (1H, d, J=8.8Hz), 7.66 (1H, d, J=1.2Hz), 7.77 (1H, s).

(30)

5-[2-[2-(Acetylamino)-4-(methyl)-(5-thiazolyl)sulfonylamino]ethylthio]imidazo[1,2-a]pyridine (Compound 51)

NMR (200Hz, DMSO-d$_6$) δ: 2.17 (3H, s), 2.38 (3H, s), 3.07–3.49 (4H, m), 7.02 (1H, d, J=7.2Hz), 7.23 (1H, dd, J=8.8, 7.2Hz), 7.54 (1H, d, J=8.8Hz), 7.67 (1H, s,), 7.90 (1H, s), 8.20 (1H, br).

(31)

5-[3-(1-Naphthylsulfonylamino)propylthio]imidazo[1,2-a]pyridine (Compound 52)

Melting point: 140°–141° C.

Elemental analysis for C$_{20}$H$_{19}$N$_3$O$_2$S$_2$, Calcd.: C, 60.43; H, 4.82; N, 10.57. Found: C, 60.58; H, 4.85; N, 10.60.

(32)

5-[2-[N-Methyl-N-(1-naphthylsulfonylamino)]ethylthio]imidazo[1,2-a]pyridine hydrochloride (Compound 53)

Melting point: 161°–164° C.

Elemental analysis for C$_{20}$H$_{19}$N$_3$O$_2$S$_2$.HCl, Calcd.: C, 55.35; H, 4.65; N, 9.68. Found: C, 55.31; H, 4.69; N, 9.55.

NMR (200Hz, CDCl$_3$) of the free compound: δ: 2.90 (3H, s), 3.12 (2H, m), 3.42 (2H, m), 6.92 (1H, dd, J=7, 1Hz), 7.14 (1H, dd, J=9, 7Hz), 7.45 (1H, dd, J=8.4, 7.4Hz), 7.53–7.71 (5H, m), 7.90 (1H, m), 8.02 (1H, d, J=8.4Hz), 8.09 (1H, dd, J=7.4, 1.2Hz), 8.60 (1H, m).

(33)
5-[2-[N-Ethyl-N-(1-naphthylsulfonylamino)]ethylthio]imidazo[1,2-a]pyridine hydrochloride (Compound 54)

Melting point: 178°–185° C.
Elemental analysis for $C_{21}H_{21}N_3O_2S_2 \cdot HCl$, Calcd.: C, 56.30; H, 4.95; N, 9.38. Found: C, 56.27; H, 4.97; N, 9.29.
NMR (200Hz, CDCl$_3$) of the free compound δ: 1.06 (3H, t, J=7.2Hz), 3.06 (2H, m), 3.30–3.50 (4H, m), 6.90 (1H, d, J=7.2Hz), 7.15 (1H, dd, J=9, 7.2Hz), 7.41 (1H, m), 7.53–7.71 (5H, m), 7.86–8.10 (3H, m), 8.54 (1H, m).

(34)
5-[2-[N-(2-Hydroxyethyl)-N-(1-naphthylsulfonylamino)]ethylthio]imidazo[1,2-a]pyridine hydrochloride (Compound 55)

Melting point: 172°–176° C.
Elemental analysis for $C_{21}H_{21}N_3O_3S_2 \cdot HCl$, Calcd.: C, 54.36; H, 4.78; N, 9.06. Found: C, 54.74; H, 4.85; N, 8.88.
NMR (200Hz, CDCl$_3$) of the free compound δ: 2.10 (1H, br), 3.18 (2H, m), 3.41–3.62 (4H, m), 3.74 (2H, t, J=5.2Hz), 6.90 (1H, dd, J=7, 1Hz), 7.12 (1H, dd, J=9, 7Hz), 7.42 (1H, m), 7.85–8.10 (3H, m), 7.85–8.10 (3H, m), 8.56 (1H, m).

(35)
2-Methyl-5-[2-(1-naphthylsulfonylamino)ethylthio]imidazo[1,2-a]pyridine (Compound 56)

Elemental analysis for $C_{20}H_{19}N_3O_2S_2$, Calcd.: C, 60.43; H, 4.82; N, 10.57. Found: C, 60.24; H, 4.84; N, 10.52.
NMR (200Hz, CDCl$_3$) δ: 2.44 (3H, s), 2.89–3.11 (4H, m), 5.30 (1H, br), 6.47 (1H, dd, J=7, 1.2Hz), 6.85 (1H, dd, J=9, 7Hz), 7.36–7.53 (3H, m), 7.96 (1H, dd, J=6.8, 1.8Hz), 8.06 (1H, d, J=8.2Hz), 8.19 (1H, dd, J=7.4, 1.2Hz), 8.63 (1H, dd, J=8.4Hz).

(36)
3-Ethoxycarbonyl-2-methyl-5-[2-[1-(naphthyl)sulfonylamino]ethylthio]imidazo[1,2-a]pyridine (Compound 57)

Elemental analysis for $C_{23}H_{23}N_3O_4S_2 \cdot 0.5H_2O$, Calcd.: C, 57.72; H, 5.05; N, 8.78. Found: C, 57.85; H, 5.02; N, 8.63.
NMR (200Hz, CDCl$_3$) δ: 1.41 (3H, t, J=7.2Hz), 2.61 (3H, s), 2.95–3.05 (4H, m), 4.42 (2H, q, J=7.2Hz), 5.29 (1H, br), 6.82 (1H, dd, J=7.2, 1Hz), 7.22 (1H, dd, J=9, 7.2Hz), 7.42–7.66 (4H, m), 7.91 (1H, m), 8.04 (1H, d, J=8Hz), 8.16 (1H, dd, J=7.4, 1.4Hz), 8.54 (1H, m).

(37)
2-Ethoxycarbonyl-5-[2-(1-naphthylsulfonylamino)ethylthio]imidazo[1,2-a]pyridine (Compound 58)

Elemental analysis for $C_{22}H_{21}N_3O_4S_2$, Calcd.: C, 58.00; H, 4.65; N, 9.22. Found: C, 57.79; H, 4.63; N, 9.24.
NMR (200Hz, CDCl$_3$) δ: 1.45 (3H, t, J=7.2Hz), 2.98 (2H, m), 3.12 (2H, m), 4.47 (2H, q, J=7.2Hz), 5.26 (1H, br), 6.65 (1H, dd, J=7, 1Hz), 7.03 (1H, dd, J=9, 7Hz), 7.44–7.73 (4H, m), 7.95 (1H, dd, J=7.8, 1.6Hz), 8.05 (1H, d, J=8.2Hz), 8.19 (1H, dd, J=7.2, 1.2Hz), 8.24 (1H, s), 8.62 (1H, m).

EXAMPLE 11

According to the same manner as that described in Example 4 (1), the following compound was obtained.

3-Bromo-5-[2-(1-(naphthyl)sulfonylamino)ethylthio]imidazo[1,2-a]pyridine (Compound 59)

Elemental analysis for $C_{19}H_{16}N_3O_2S_2Br$, Calcd.: C, 49.35; H, 3.49; N, 9.09. Found: C, 49.39; H, 3.47; N, 8.98.
NMR (200Hz, CDCl$_3$) δ: 2.91 (2H, m), 3.10 (2H, m), 5.32 (1H, br), 6.51 (1H, dd, J=7, 1Hz), 6.83 (1H, dd, J=9, 7Hz), 7.43–7.73 (5H, m), 7.94 (1H, dd, J=7.8, 1.6Hz), 8.04 (1H, d, J=8.2Hz), 8.19 (1H, dd, J=7.4, 1.2Hz), 8.64 (1H, d, J=8.2Hz).

EXAMPLE 12

According to the same manner as that described in Example 3 (1), the following compounds were obtained.

(1)
5-[2-(Methylsulfonylamino)ethylamino]imidazo[1,2-a]pyridine (Compound 60)

NMR (90Hz, CDCl$_3$-DMSO-d$_6$) δ: 2.90 (3H, s), 3.44 (4H, m), 6.16 (1H, d, J=7.5Hz), 6.99 (1H, d, J=9Hz), 7.28 (2H, br), 7.43 (1H, dd, J=9, 7.5Hz), 7.66 (1H, d, J=1.5Hz), 8.23 (1H, s).

(2)
5-[3-(Methylsulfonylamino)propylamino]imidazo[1,2-a]pyridine (Compound 61)

NMR (90Hz, CDCl$_3$-DMSO-d$_6$) δ: 1.97 (2H, m), 2.90 (3H, s), 3.17 (2H, m), 3.46 (2H, m), 6.19 (1H, d, J=8Hz), 6.91–7.20 (2H, m), 7.37–7.63 (2H, m), 7.71 (1H, d, J=2Hz), 8.36 (1H, d, J=2Hz).

(3)
5-[2-(Methylsulfonylamino)ethyloxy]imidazo[1,2-a]pyridine (Compound 62)

Elemental analysis for $C_{10}H_{13}N_3O_3S$, Calcd.: C, 47.05; H, 5.13; N, 16.46. Found: C, 46.95; H, 5.17; N, 16.38.
NMR (200MHz, DMSO-d$_6$) δ: 2.98 (3H, s), 3.49 (2H, m), 4.35 (2H, t, J=5.2Hz), 6.34 (1H, dd, J=6, 1.6Hz), 7.16–7.32 (2H, m), 7.50 (1H, br), 7.57 (1H, d, J=1.2Hz), 7.91 (1H, s).

(4)
5-[2-(Trifluoromethylsulfonylamino)ethyloxy]imidazo[1,2-a]pyridine (Compound 63)

NMR (200MHz, DMSO-d$_6$) δ: 3.71 (2H, m), 4.38 (2H, t, J=5Hz), 6.38 (1H, dd, J=6.6, 1.6Hz), 7.19–7.34 (2H, m), 7.60 (1H, s), 7.87 (1H, s).

(5)
5-[3-(methylsulfonylamino)propyloxy]imidazo[1,2-a]pyridine (Compound 64)

NMR (200Hz, CDCl$_3$-DMSO-d$_6$) δ: 2.20 (2H, m), 2.93 (3H, s), 3.35 (2H, m), 4.39 (2H, t, J=6.2Hz), 6.11 (1H, dd, J=6.8, 1.6Hz), 6.91 (1H, br), 7.14–7.29 (2H, m), 7.57 (1H, d, J=1.4Hz), 7.67 (1H, m).

(6)
5-[3-(Trifluoromethylsulfonylamino)propyloxy]imidazo[1,2-a]pyridine (Compound 65)

NMR (200Hz, DMSO-d$_6$) δ: 2.05 (2H, m), 2.91 (3H, s), 3.21 (2H, m), 4.38 (2H, t, J=6Hz), 6.35 (1H, dd, J=7, 1.2Hz), 7.10–7.32 (3H, m), 7.56 (1H, d, J=1.4Hz), 7.78 (1H, s).

(7)
5-[4-(methylsulfonylamino)butyloxy]imidazo[1,2-a]pyridine (Compound 66)

Elemental analysis for $C_{12}H_{17}N_3O_3S$, Calcd.: C, 50.87; H, 6.05; N, 14.83. Found: C, 50.60; H, 6.11; N, 14.78.

NMR (200Hz, $CDCl_3$) δ: 1.87 (2H, m), 2.04 (2H, m), 2.99 (3H, s), 3.28 (2H, m), 4.29 (2H, t, J=6.2Hz), 4.58 (1H, br), 6.04 (1H, d, J=7.2Hz), 7.17 (1H, dd, J=9, 7.2Hz), 7.29 (1H, d, J=9Hz), 7.59 (1H, d, J=1.4Hz), 7.63 (1H, m).

(8)
5-[4-(Trifluoromethylsulfonylamino)butyloxy]imidazo[1,2-a]pyridine (Compound 67)

Elemental analysis for $C_{12}H_{14}N_3O_3SF_3$ Calcd.: C, 42.73; H, 4.18; N, 12.56. Found: C, 42.53; H, 4.27; N, 12.25.

NMR (200Hz, $CDCl_3$-DMSO-$d_6$) δ: 1.87 (2H, m), 2.03 (2H, m), 3.30 (2H, m), 4.30 (2H, t, J=6Hz), 6.08 (1H, dd, J=6.4, 1.4Hz), 7.14–7.28 (2H, m), 7.57 (1H, s), 7.68 (1H, s).

(9)
5-[5-(Methylsulfonylamino)pentyloxy]imidazo[1,2-a]pyridine (Compound 68)

Elemental analysis for $C_{13}H_{19}N_3O_3S$ Calcd.: C, 52.51; H, 6.44; N, 14.13. Found: C, 52.22; H, 6.53; N, 13.83.

NMR (200Hz, $CDCl_3$) δ: 1.54–1.80 (4H, m), 1.97 (2H, m), 3.20 (2H, m), 4.25 (2H, t, J=6.2Hz), 4.59 (1H, br), 6.02 (1H, dd, J=7.2, 1Hz), 7.17 (1H, dd, J=9, 7Hz), 7.28 (1H, d, J=9Hz), 7.59(1H, d, J=1.4Hz), 7.63 (1H, m).

(10)
5-[5-(Trifluoromethylsulfonylamino)pentyloxy]imidazo[1,2-a]pyridine (Compound 69)

Elemental analysis for $C_{13}H_{16}N_3O_3SF_3$, Calcd.: C, 44.44; H, 4.59; N, 11.96. Found: C, 44.47; H, 4.63; N, 11.71.

NMR (200Hz, $CDCl_3$) δ: 1.63–2.02 (6H, m), 3.42 (2H, m), 4.18 (2H, t, J=6Hz), 5.94 (1H, d, J=7Hz), 7.12 (1H, dd, J=9, 7Hz), 7.23 (1H, d, J=9Hz), 7.30 (1H, d, J=1Hz), 7.41 (1H, d, J=1Hz).

(11)
5-[6-(Methylsulfonylamino)hexyloxy]imidazo[1,2-a]pyridine (Compound 70)

Elemental analysis for $C_{14}H_{21}N_3O_3S \cdot 0.2H_2O$, Calcd.: C, 53.38; H, 6.85; N, 13.34. Found: C, 53.67; H, 7.04; N, 13.28.

NMR (200Hz, $CDCl_3$) δ: 1.40–1.73 (6H, m), 1.91 (2H, m), 3.17 (2H, m), 4.24 (2H, t, J=6.2Hz), 4.61 (1H, br), 6.02 (1H, dd, J=7, 1Hz), 7.17 (1H, dd, J=9, 7Hz), 7.28 (1H, d, J=9Hz), 7.59 (1H, d, J=1.4Hz), 7.65 (1H, m).

(12)
5-[6-(Trifluoromethylsulfonylamino)hexyloxy]imidazo[1,2-a]pyridine (Compound 71)

NMR (200Hz, $CDCl_3$) δ: 1.32–2.03 (8H, m), 3.37 (2H, t, 6.6Hz), 4.17 (2H, t, J=6.2Hz), 5.97 (1H, d, J=7Hz), 7.16 (1H, dd, J=9, 7Hz), 7.21 (1H, br), 7.25 (1H, d, J=9Hz), 7.51 (1H, d, J=1.1Hz), 7.54 (1H, s).

(13)
5-[2-(Methylsulfonylamino)propyloxy]imidazo[1,2-a]pyridine (Compound 72)

Melting point: 171°–172° C.

(14)
5-[1-(Methylsulfonylamino)-(2-propyloxy)]imidazo[1,2-a]pyridine (Compound 73)

Elemental analysis for $C_{11}H_{15}N_3O_3S$, Calcd.: C, 49.06; H, 5.61; N, 15.60. Found: C, 48.81; H, 5.63; N, 15.59.

NMR (200Hz, $CDCl_3$) δ: 1.47 (3H, d, J=6.2 Hz), 3.01 (3H, s), 3.50 (2H, m), 4.84 (1H, m), 6.10 (1H, d, J=7.4Hz), 6.38 (1H, br), 7.09 (1H, dd, J=9, 7.4Hz), 7.21 (1H, d, J=9Hz), 7.41 (1H, d, J=1.4Hz).

(15)
5-[2-(Methylsulfonylamino)-1-(phenyl)ethyloxy]imidazo[1,2-a]pyridine (Compound 74)

NMR (200Hz, $CDCl_3$) δ: 2.94 (3H, s), 3.61–3.83 (2H, m), 5.33 (1H, br), 5.58 (1H, dd, J=7, 4.6Hz), 5.91 (1H, d, J=7.4Hz), 7.00 (1H, dd, J=9, 7.4Hz), 7.24 (1H, d, J=9Hz), 7.40 (5H, m), 7.60 (1H, d, J=1.4Hz), 7.73 (1H, s).

(16)
5-[[1-(Phenyl)-2-(trifluoromethylsulfonylamino)]ethyloxy]imidazo[1,2-a]pyridine (Compound 75)

NMR (200Hz, $CDCl_3$-DMSO-$d_6$) δ: 3.49 (2H, m), 5.06 (1H, dd, J=8, 4Hz), 5.98 (1H, d, J=8.8Hz), 5.98 (1H, br), 7.04 (1H, d, J=8.8Hz), 7.20–7.52 (6H, m), 7.60 (1H, s), 7.81 (1H, s).

(17)
5-[1-(Methylsulfonyl)-4-piperidyloxy]imidazo[1,2-a]pyridine (Compound 76)

NMR (200Hz, $CDCl_3$) δ: 2.19 (4H, m), 2.86 (3H, s), 3.44 (4H, m), 4.84 (1H, quint, J=4.4Hz), 6,08 (1H, d, J=7Hz), 7.18 (1H, dd, J=9, 7Hz), 7.31 (1H, d, J=9Hz), 7.63 (1H, d, J=1.4Hz), 7.65 (1H, s).

(18)
5-[1-(Trifuloromethylsulfonyl)-4-piperidyloxy]imidazo[1,2-a]pyridine (Compound 77)

NMR (200Hz, $CDCl_3$) δ: 2.18 (4H, m), 3.71 (4H, s), 4.99 (1H, m), 6,08 (1H, d, J=7Hz), 7.19 (1H, dd, J=9, 7Hz), 7.33 (1H, d, J=9Hz), 7.64 (1H, s), 7.65 (1H, s).

(19)
5-[2-(1-(Naphthyl)sulfonylamino)ethyloxy]imidazo[1,2-a]pyridine (Compound 78)

Elemental analysis for $C_{19}H_{17}N_3O_3S$, Calcd.: C, 62.11: H, 4.66; N, 11.44. Found: C, 62.04; H, 4.57; N, 11.41.

NMR (200Hz, DMSO-$d_6$) δ: 3.38 (2H, m), 4.11 (2H, t, J=5.2Hz), 6.06 (1H, m), 7.08–7.20 (2H, m), 7.46–7.65 (5H, m), 8.00 (1H, m), 8.16 (1H, s), 8.20 (1H, s). 8.47 (1H, br), 8.64 (1H, m).

(20)
5-[3-(1-(Naphthyl)sulfonylamino)propyloxy]imidazo[1,2-a]pyridine (Compound 79)

Elemental analysis for $C_{20}H_{19}N_3O_3S$, Calcd.: C, 62.97; H, 5.02; N, 11.02. Found: C, 62.82; H, 4.98; N, 11.14.

NMR (200Hz, $CDCl_3$-DMSO-$d_6$) δ: 1.98 (2H, m), 3.19 (2H, m), 3.98 (2H, t, J=6Hz), 5.59 (1H, d,

J=7.2Hz), 6.99-7.35 (4H, m), 7.43-7.63 (3H, m), 7.67-7.80 (3H, m), 8.14 (1H, d, J=7.4Hz), 8.68 (1H, d, J=8.2Hz).

(21)
5-[6-(1-(Naphthyl)sulfonylamino)hexyloxy]imidazo[1,2-a]pyridine (Compound 80)

Elemental analysis for $C_{23}H_{25}N_3O_3S \cdot 0.3H_2O$, Calcd.: C, 64.40; H, 6.02; N, 9.80. Found: C, 64.66; H, 6.07; N, 9.68.

NMR (200Hz, CDCl$_3$) δ: 1.10-1.83 (8H, m), 2.94 (2H, m), 4.12 (2H, t, J=6.4Hz), 4.76 (1H, t, J=6.6Hz), 5.98 (1H, d, J=7Hz), 7.16 (1H, dd, J=9, 7Hz), 7.28 (1H, d, J=9Hz), 7.50-7.72 (5H, m), 7.94 (1H, d, J=7.6Hz), 8.07 (1H, d, J=8.4Hz), 8.28 (1H, dd, J=7.4, 1.2Hz), 8.66 (1H, d, J=8.8Hz).

(22)
5-[2-(1-(Naphthyl)sulfonylamino)propyloxy]imidazo[1,2-a]pyridine (Compound 81)

Melting point: 188°-190° C.

(23)
5-(1-(1-Naphthylsulfonyl))-(4-piperidyl)oxy]imidazo[1,2-a]pyridine (Compound 82)

NMR (200Hz, CDCl$_3$) δ: 1.94-2.23 (4H, m), 3.29-3.53 (4H, m), 4.70 (1H, m), 5.98 (1H, d, J=7Hz), 7.12 (1H, dd, J=9, 7Hz), 7.25 (1H, d, J=9Hz), 7.39 (1H, s), 7.53 (1H, s), 7.53-7.73 (3H, m), 7.98 (1H, dd, J=7.2, 2.2Hz), 8.13 (1H, d, J=8.4Hz), 8.27 (1H, dd, J=7.4, 1.2Hz), 8.75 (1H, dd, J=7.8, 2.2Hz).

EXAMPLE 13

(1) Synthesis of 5-[2-(acetylamino)ethylthio]imidazo[1,2-a]pyridine (Compound 83)

To a solution of 5-[2-(amino)ethylthio]imidazo[1,2-a]pyridine dihydrochloride (2.66 g, 10 mmoles) and triethylamine (4.32 ml, 31 mmoles) in N,N-dimethylformamide (24 ml) was added acetyl chloride (0.71 ml, 10 mmoles) under ice-cooling with stirring and the mixture was stirred at room temperature for 4 hours. The reaction mixture was poured into water and extracted with chloroform. The chloroform layer was washed with saturated saline and dried over anhydrous magnesium sulfate. After the solvent was distilled off, the residue was purified by column chromatography (eluent: ethanol/ethyl acetate=1:3) to obtain 1.57 g of the desired product (66.8%, colorless crystals).

Elemental analysis for $C_{11}H_{13}N_8OS \cdot 0.3H_2O$, Calcd.: C, 54.89; H, 5.69; N, 17.46. Found: C, 55.29; H, 5.52; N, 17.42.

NMR (90MHz, CDCl$_3$) δ: 1.93 (3H, s), 3.13 (2H, m), 3.46 (2H, m), 6.98 (1H, dd, J=7, 1.5Hz), 7.07 (1H, br), 7.13 (1H, dd, J=8.5, 7Hz), 7.51 (1H, d, J=8.5Hz), 7.65 (1H, s), 7.81 (1H, s).

According to the same manner as that described in Examples 2 and 13 (1), the following compounds were obtained.

(2)
5-[2-(Trifluoroacetylamino)ethylthio]imidazo[1,2-a]pyridine (Compound 84)

NMR (90MHz, DMSO-d$_6$) δ: 3.17-3.60 (4H, m), 7.12 (1H, dd, J=7, 1.5Hz), 7.27 (1H, dd, J=9, 7Hz), 7.58 (1H, d, J=9Hz), 7.67 (1H, d, J=1.5Hz), 7.96 (1H, s), 9.60 (1H, br).

(3)
5-[2-(Decanoylamino)ethylthio]imidazo[1,2-a]pyridine (Compound 85)

NMR (90MHz, CDCl$_3$) δ: 1.70-1.78 (17H, m), 2.15 (2H, m), 3.15 (2H, m), 3.49 (2H, m), 6.53 (1H, br), 7.00 (dd, J=7, 1.5Hz), 7.15 (1H, d, J=9, 7Hz), 7.23 (1H, d, J=9Hz), 7.67 (1H, s), 7.84 (1H, s).

(4)
5-[2-(Aminoacetylamino)ethylthio]imidazo[1,2-a]pyridine dihydrochloride (compound 86)

NMR (200MHz, DMSO-d$_6$) δ: 3.32-3.53 (4H, m), 3.55 (2H, s), 7.69 (1H, dd, J=6, 2.6Hz), 7.86 7.99 (2H, m), 8.22 (1H, d, J=2.2Hz), 8.26 (1H, d, J=2.2Hz), 8.79 (1H, br).

(5)
5-[2-(Benzoylamino)ethylthio]imidazo[1,2-a]pyridine (Compound 87)

NMR (90MHz, CDCl$_3$) δ: 3.27 (2H, m), 3.70 (2H, m), 6.74 (1H, br), 6.97-7.23 (2H, m), 7.30-7.95 (8H, m).

(6)
5-[2-[3(2H)-Pyridazinone-6-carbonylamino]ethylthio]imidazo[1,2-a]pyridine (Compound 88)

NMR (90MHz, DMSO-d$_6$) δ: 3.15-3.67 (4H, m), 6.93 (1H, d, J=10Hz), 7.10-7.62 (3H, m), 7.66 (1H, s), 7.80 (1H, d, J=10Hz), 7.92 (1H, s), 8.64 (1H, br).

(7)
5-[2-[(2-Thenoylamino)]ethylthio]imidazo[1,2-a]pyridine (Compound 89)

NMR (200MHz, CDCl$_3$) δ: 3.27 (2H, t, J=6.4Hz), 3.68 (2H, m), 6.57 (1H, br), 7.02-7.20 (3H, m), 7.41-7.69 (3H, m), 7.69 (1h, d, J=1.2Hz), 7.85 (1H, s).

(8)
5-[2-(1-Naphthoyl)aminoethylthio]imidazo[1,2-a]pyridine hydrochloride (Compound 90)

NMR (200MHz, DMSO-d$_6$) δ: 3.50-3.75 (4H, m), 7.51-7.67 (4H, m), 7.75-8.07 (5H, m), 8.22 (1H, m), 8.32 (1H, d, J=2.2Hz), 8.41 (1H, d, J=2.2Hz), 8.85 (1H, br).

NMR (200MHz, CDCl$_3$) of the free amine δ: 3.30 (2H, t, J=6.4Hz), 3.74 (2H, m), 6.68 (1H, br), 7.01-7.16 (2H, m), 7.36-7.58 (5H, m), 7.64 (1H, d, J=1.2Hz), 7.80-7.94 (3H, m), 8.29 (1H, m).

(9)
5-[2-(2-Naphthoylamino)ethylthio]imidazo[1,2-a]pyridine (Compound 91)

NMR (200MHz, CDCl$_3$) δ: 3.34 (2H, t, J=6.4Hz), 3.78 (2H, m), 6.72 (1H, br), 7.06-7.20 (2H, m), 7.51-7.94 (9H, m), 8.20 (1H, s).

(10)
5-[2-(Nicotinoylamino)ethylthio]imidazo[1,2-a]pyridine (Compound 92)

NMR (200MHz, CDCl$_3$) δ: 3.30 (2H, t, J=6.4Hz), 3.74 (2H, m), 6.85 (1H, br), 7.05 (1H, dd, J=7, 1.2Hz), 7.16 (1H, dd, J=9, 7Hz), 7.39 (1H, m), 7.55 (1H, d, J=9Hz), 7.68 (1H, d, J=1.4Hz), 7.85 (1H, s), 8.05 (1H, m), 8.74 (1H, dd, J=4.8, 1.8Hz), 8.95 (1H, d, J=7.2Hz).

(11)
5-[2-(Isonictotinoylamino)ethylthio]imidazo[1,2-a]pyridine (Compound 93)

NMR (200MHz, CDCl$_3$-DMSO-d$_6$) δ: 3.29 (2H, m), 3.68 (2H, m), 7.11 (1H, dd, J=7, 1.4Hz), 7.19 (1H, dd, J=8.8, 7.2Hz), 7.57 (1H, d, J=8.8Hz), 7.68 (2H, m), 7.88 (1H, m), 8.23 (1H, br), 8.72 (2H, m).

(12)
5-[2-[3,4-(Dimethoxy)phenylacetylamino]ethylthio]imidazo[1,2-a]pyridine.hydrochloride (Compound 94)

Melting point 150°-165° C.

NMR (200MHz, CDCl$_3$) of the free amine δ: 3.11 (2H, t, J=6.6Hz), 3.43 (2H, m), 3.49 (2H, s), 3.85 (3H, s), 3.87 (3H, s), 6.02 (1H, br), 6.69-6.95 (4H, m), 7.12 (1H, dd, J=9, 7Hz), 7.56 (1H, d, J=9Hz), 7.66 (1H, s), 7.74 (1H, s).

(13)
5-[2-[3-(3-Pyridyl)acryloylamino]ethylthio]imidazo[1,2-a]pyridine.dihydrochloride (Compound 95)

NMR (200MHz, D$_2$O) δ: 3.41 (2H, m), 3.61 (2H, m), 6.60 (1H, d, J=16Hz), 7.36 (1H, d, J=16Hz), 7.58-8.05 (5H, m), 8.22 (1H, d, J=2.6Hz), 8.59-8.72 (2H, m), 8.66 (1H, m).

(14)
5-[3-(Benzoylamino)propylamino]imidazo[1,2-a]pyridine (Compound 96)

NMR (90MHz, CDCl$_3$-DMSO-d$_6$) δ: 1.99 (2H, m), 3.27-3.70 (4H, m), 5.86 (1H, d, J=7Hz), 6.25 (1H, br), 6.98 (1H, d, J=9Hz), 7.17 (1H, dd, J=9, 7Hz), 7.33-8.17 (8H, m).

(15)
5-[3-(Decanoylamino)propylamino]imidazo[1,2-a]pyridine (Compound 97)

NMR (90MHz, CDCl$_3$) δ: 0.73-2.00 (19H, m), 2.22 (2H, m), 3.22-3.53 (4H, m), 5.77-6.03 (2H, m), 6.21 (1H, br), 6.95-7.22 (2H, m), 7.62 (1H, s), 7.71 (1H, s).

EXAMPLE 14

(1) Synthesis of 5-[2-[2-(carboxy)benzoylamino]ethylthio]imidazo[1,2-a]pyridine (Compound 98)

To a solution of 5-[2-(amino)ethylthio]imidazo[1,2-a]pyridine (1.12 g, 5.8 mmoles) in chloroform (58 ml) was added phthalic anhydride (1.12 g, 7.56 mmoles) and the mixture was stirred at room temperature for 14 hours and then heated at reflux for 5 hours. The reaction mixture was cooled by standing. The crystals precipitated were filtered off, washed with chloroform and dried to obtain 1.68 g of the desired product (84.8%, colorless crystals).

NMR (90MHz, DMSO-d$_6$) δ: 3.17-3.63 (4H, m), 7.15-7.91 (8H, m), 7.98 (1H, s), 8.21 (1H, br).

EXAMPLE 15

(1) Synthesis of 5-[2-(phthalimide)ethylthio]imidazo[1,2-a]pyridine (Compound 99)

To 5-[2-[2-(carboxy)benzoylamino]ethylthio]imidazo[1,2-a]pyridine dihydrochloride (638 mg, 2 mmoles) was added hydrogen chloride-methanol solution (40 ml) and the mixture was heated at reflux for 24 hours. After the solvent was distilled off, the residue was dissolved in chloroform, washed with an aqueous saturated sodium bicarbonate solution and dried over anhydrous magnesium sulfate. After the solvent was distilled off, the residue was purified by column chromatography (eluent: ethyl acetate) to obtain 530 mg of the desired product (81.9%, yellow crystals).

NMR (90MHz, CDCl$_3$) δ: 3.31 (2H, t, J=7Hz), 3.95 (2H, t, J=7Hz), 7.05-7.19 (2H, m), 7.42-7.92 (7H, m).

EXAMPLE 16

(1) Synthesis of 5-[2-(methylcarbamoylamino)ethylthio]imidazo[1,2-a]pyridine (Compound 100)

To a solution of 5-[2-(amino)ethylthio]imidazo[1,2-a]pyridine (1.93 g, 10 mmoles) in methylene chloride (30 ml) was added methyl isocyanate (0.59 ml, 10 mmoles) under ice-cooling with stirring and the mixture was stirred under ice-cooling for 1 hour. After the solvent was distilled off, the residue was purified by column chromatography (eluent: ethanol/ethyl acetate=1:5) to obtain 2.15 g of the desired product (86.0%, pale yellow crystals).

NMR (90MHz, CDCl$_3$) δ: 2.74 (3H, d, J=5.5Hz), 3.14 (2H, m), 3.43 (2H, m), 5.28 (1H, br), 5.76 (1H, br), 6.96 (1H, dd, J=7, 1Hz), 7.12 (1H, dd, J=9, 7Hz), 7.51 (1H, d, J=9Hz), 7.65 (1H, s), 7.79 (1H, s).

According to the same manner as that described in Example 16 (1), the following compounds were obtained.

(2)
5-[2-(Ethylcarbamoylamino)ethylthio]imidazo[1,2-a]pyridine (Compound 101)

NMR (200MHz, CDCl$_3$) δ: 1.11 (3H, t, J=7.2Hz), 3.16 (4H, m), 3.44 (2H, m), 4.72 (1H, br), 5.16 (1H, br), 6.97 (1H, dd, J=7, 1Hz), 7.14 (1H, dd, J=9, 7Hz). 7.53 (1H, d, J=9Hz), 7.66 (1H, d, J=1.2Hz), 7.78 (1H, s).

(3)
5-[2-(Propylcarbamoylamino)ethylthio]imidazo[1,2-a]pyridine (Compound 102)

NMR (200MHz, CDCl$_3$) δ: 0.90 (3H, t, J=7.4Hz), 1.49 (2H, m), 3.03-3.22 (4H, m), 3.45 (2H, m), 4.68 (1H, br), 5.07 (1H, br), 6.98 (1H, dd, J=7, 1Hz). 7.15 (1H, d, J=9, 7Hz), 7.54 (1H, d, J=9Hz), 7.67 (1H, d, J=1.2Hz), 7.80 (1H, s).

(4)
5-[2-(Isopropylcarbamoylamino)ethylthio]imidazo[1,2-a]pyridine (Compound 103)

NMR (200MHz, CDCl$_3$) δ: 1.22 (6H, t, J=6.6Hz), 3.17 (2H, t, J=6.4Hz), 3.44 (2H, m), 3.84 (1H, heptet, J=6.4Hz), 4.44 (1H, br), 4.96 (1H, br), 6.98 (1H, d, J=7Hz). 7.15 (1H, dd, J=9, 7Hz), 7.55 (1H, d, J=9Hz), 7.68 (1H, d, J=1.2Hz), 7.80 (1H, s).

(5)
5-[2-(Butylcarbamoylamino)ethylthio]imidazo[1,2-a]pyridine (Compound 104)

NMR (200MHz, CDCl$_3$) δ: 0.89 (3H, t, J=7Hz), 1.20-1.52 (4H, m), 3.07-3.20 (4H, m), 3.43 (2H, m), 5.23 (1H, br), 5.68 (1H, br), 6.95 (1H, dd, J=7, 1Hz). 7.12 (1H, dd, J=9, 7Hz), 7.49 (1H, d, J=9Hz), 7.63 (1H, d, J=1.2Hz), 7.75 (1H, s).

(6)
5-[2-(Cyclohexylcarbamoylamino)ethylthio]imidazo[1,2-a]pyridine (Compound 105)

NMR (200MHz, CDCl$_3$) δ: 0.95–1.97 (10H, m), 3.17 (2H, t, J=6.4Hz), 3.35–3.55 (3H, m), 4.48 (1H, br), 4.93 (1H, br), 6.99 (1H, d, J=7.2Hz), 7.16 (1H, dd, J=9, 7.2Hz). 7.55 (1H, d, J=9Hz), 7.68 (1H, s), 7.80 (1H, s).

(7)
5-[2-(Phenylcarbamoylamino)ethylthio]imidazo[1,2-a]pyridine (Compound 106)

NMR (200MHz, CDCl$_3$-DMSO-d$_6$) δ: 3.19 (2H, m), 3.46 (2H, m), 6.25 (1H, br), 6.83–7.63 (8H, m), 7.69 (1H, s), 7.88 (1H, s), 8.14 (1H, br).

EXAMPLE 17

(1) Synthesis of 5-[2-(methylthiocarbamoylamino)ethylthio]imidazo[1,2-a]pyridine (Compound 107)

To a solution of 5-[2-(amino)ethylthio]imidazo[1,2-a]pyridine (2.96 g, 15.3 mmoles) in methylene chloride (50 ml) was added methyl isocyanate (1.12 ml, 15.3 mmoles) under ice-cooling with stirring and the mixture was stirred at room temperature for 3 hours. After the solvent was concentrated, ether was added. Then, the crystals precipitated were filtered off and washed with ether to obtain 2.76 g of the desired product (67.6%, colorless crystals).

Elemental analysis for C$_{11}$H$_{14}$N$_4$S$_2$, Calcd.: C, 49.60; H, 5.30; N, 21.03. Found: C, 49.63; H, 5.34; N, 21.03.

NMR (200MHz, CDCl$_3$-DMSO-d$_6$) δ: 2.95 (3H, d, J=5Hz), 3.30 (2H, m), 3.80 (2H, m), 7.00–7.65 (5H, m), 7.67 (1H, d, J=1Hz), 7.87 (1H, s).

According to the same manner as that described in Example 17 (1), the following compounds were obtained.

(2)
5-[2-(Phenylthiocarbamoylamino)ethylthio]imidazo[1,2-a]pyridine (Compound 108)

NMR (200MHz, CDCl$_3$) δ: 3.31 (2H, m), 3.86 (2H, m), 6.44 (1H, br), 6.96 (1H, dd, J=7, 1.5Hz), 7.03–7.64 (7H, m), 7.67 (1H, dd, J=7, 1.5Hz), 7.77 (1H, s), 8.05 (1H, br).

(3)
5-[2-[4-(Methoxy)phenylthiocarbamoylamino]ethylthio]imidazo[1,2-a]pyridine (Compound 109)

NMR (200MHz, CDCl$_3$-DMSO-d$_6$) δ: 3.32 (2H, m), 3.79 (2H, m), 3.82 (2H, m), 6.78–7.58 (1H, d, J=7, 2Hz), 7.64 (1H, d, J=2Hz), 7.85 (1H, d, J=2Hz), 9.21 (1H, br).

(4)
5-[2-[4-(Methyl)phenylthiocarbamoylamino]ethylthio]imidazo[1,2-a]pyridine (Compound 110)

NMR (200MHz, CDCl$_3$-DMSO-d$_6$) δ: 2.34 (3H, s), 3.32 (2H, m), 3.86 (2H, m), 7.05–7.33 (7H, m), 7.55 (1H, d, J=9Hz), 7.68 (1H, s), 7.85 (1H, s), 8.98 (1H, br).

(5)
5-[2-[4-(Chloro)phenylthiocarbamoylamino]ethylthio]imidazo[1,2-a]pyridine (Compound 111)

NMR (200MHz, CDCl$_3$-DMSO-d$_6$) δ: 3.34 (2H, m), 3.86 (2H, m), 7.05–7.75 (9H, m), 7.88 (1H, s), 9.36 (1H, br).

(6)
5-[2-[(1-Naphthyl)thiocarbamoylamino]ethylthio]imidazo[1,2-a]pyridine (Compound 112)

NMR (200MHz, CDCl$_3$-DMSO-d$_6$) δ: 3.32 (2H, m), 3.80 (2H, m), 7.07–7.23 (2H, m), 7.37–8.08 (11H, m), 9.65 (1H, br).

(7)
2-Ethoxycarbonylmethyl-5-[2-(phenylthiocarbamoylamino)ethylthio]imidazo[1,2-a]pyridine (Compound 113)

NMR (200MHz, CDCl$_3$) δ: 1.30 (3H, t, J=7Hz), 3.23 (2H, t, J=6.4Hz), 3.85 (2H, m), 3.88 (2H, s), 4.22 (2H, q, J=7Hz), 6.31 (1H, br), 6.94 (1H, dd, J=7, 1Hz). 7.11 (1H, dd, J=9, 7Hz), 7.13–7.53 (6H, m), 7.69 (1H, br), 7.79 (1H, s).

(8)
2-Ethoxycarbonyl-5-[2-(phenylthiocarbamoylamino)ethylthio]imidazo[1,2-a]pyridine (Compound 114)

NMR (200MHz, CDCl$_3$) δ: 1.46 (3H, t, J=7.2Hz), 3.38 (2H, t, J=6.6Hz), 3.94 (2H, m), 4.71 (2H, q, J=7.2Hz), 6.62 (1H, br), 7.07 (1H, dd, J=7, 1.2Hz), 7.16–7.54 (7H, m), 7.91 (1H, br), 8.83 (1H, s).

(9)
2-Methyl-5-[2-(phenylthiocarbamoylamino)ethylthio]imidazo[1,2-a]pyridine (Compound 1115

NMR (200MHz, CDCl$_3$) δ: 2.47 (3H, s), 3.31 (2H, t, J=6.4Hz), 3.85 (2H, m), 6.38 (1H, br), 6.88 (1H, dd, J=7, 1Hz), 7.07 (1H, dd, J=9, 7Hz). 7.15–7.52 (7H, m), 7.82 (1H, br).

(10)
3-Ethoxycarbonyl-2-methyl-5-[2-(phenylthiocarbamoylamino)ethylthio]imidazo[1,2-a]pyridine (Compound 116)

NMR (200MHz, CDCl$_3$) δ: 1.37 (3H, t, J=7Hz), 2.58 (3H, s), 3.33 (2H, t, J=6Hz), 3.76 (2H, m), 4.35 (2H, q, J=7Hz), 3.76 (2H, m), 4.35 (2H, q, J=7Hz), 6.47 (1H, br), 6.99–7.57 (8H, m), 7.76 (1H, br).

(11)
5-[3-(Phenylthiocarbamoylamino)propylthio]imidazo[1,2-a]pyridine (Compound 117)

NMR (200MHz, CDCl$_3$) δ: 1.96 (2H, m), 3.01 (2H, t, J=7Hz), 3.79 (2H, m), 6.13 (1H, br), 6.87 (1H, d, J=7Hz), 7.00–7.70 (8H, m), 7.88 (1H, s), 7.85 (1H, br).

EXAMPLE 18

(1) Synthesis of 5-[2-(methylcarbamoyloxy)ethylthio]imidazo[1,2-a]pyridine (Compound 118)

To a solution of 5-[2-(hydroxy)ethylthio]imidazo[1,2-a]pyridine (971 mg, 5 mmoles) and trietylamine (0.91 ml, 6.53 mmoles) in methylene chloride (40 ml) was added methyl isocyanate (0.65 ml, 11 mmoles) under ice-cooling with stirring and the mixture was stirred at room temperature for 12 hours. The reaction mixture was washed with saturated saline and dried over anhydrous magnesium sulfater. After the solvent was distilled off, the residue was purified by column chromatography (eluent: methanol/chloroform=1:20) to obtain 1.07 g of the desired product (85.2%, colorless crystals).

NMR (200MHz, CDCl$_3$) δ: 2.74 (3H, d, J=4.8Hz), 3.21 (2H, t, J=6.2Hz), 4.27 (2H, t, J=6.2Hz), 4.56 (1H, br), 7.05 (1H, dd, J=9, 7Hz), 7.21 (1H, dd, J=9, 7Hz), 7.61 (1H, d, J=9Hz), 7.71 (1H, s), 7.89 (1H, s).

According to the same manner as that described in Example 18 (1), the following compounds were obtained.

(2)

5-[2-(Butylcarbamoyloxy)ethylthio]imidazo[1,2-a]pyridine (Compound 119)

NMR (200MHz, CDCl$_3$) δ: 0.92 (3H, t, J=7Hz), 1.21-1.55 (4H, m), 3.03-3.30 (4H, m), 4.26 (2H, t, J=6.4Hz), 4.55 (1H, br), 7.05 (1H, d, J=7Hz), 7.17 (1H, dd, J=9, 7Hz). 7.62 (1H, d, J=9Hz), 7.72 (1H, s), 7.89 (1H, s).

(3)

5-[2-(Phenylcarbamoyloxy)ethylthio]imidazo[1,2-a]pyridine (Compound 120)

NMR (200MHz, DMSO-d$_6$) δ: 3.45 (2H, t, J=6.2Hz), 4.32 (2H, t, J=6.2Hz), 7.00 (1H, m), 7.16 (1H, dd, J=7, 1Hz), 7.22-7.34 (3H, m), 7.42-7.50 (2H, m), 7.57 (1H, d, J=9Hz), 7.70 (1H, d, J=9Hz), 7.70 (1H, d, J=1.2Hz), 7.99 (1H, s), 9.74 (1H, br).

(4)

5-[2-[(1-Naphthyl)carbamoyloxy]ethylthio]imidazo[1,2-a]pyridine (Compound 121)

NMR (200MHz, CDCl$_3$-DMSO-d$_6$) δ: 3.30 (2H, t, J=6.4Hz), 4.41 (2H, t, J=6.4Hz), 7.05-7.21 (2H, m), 7.41-7.75 (7H, m), 7.82-8.02 (3H, m), 8.11 (1H, br).

(5)

5-[2-(Benzylcarbamoyloxy)ethylthio]imidazo[1,2-a]pyridine (Compound 122)

NMR (200MHz, CDCl$_3$) δ: 3.21 (2H, t, J=6.4Hz), 4.24-4.37 (4H, m), 4.99 (1H, br), 7.24 (1H, d, J=7Hz), 7.13 (1H, dd, J=9, 7Hz), 7.24 (1H, d, J=7Hz). 7.20-7.39 (5H, m), 7.58 (1H, dd, J=9, 0.8Hz), 7.68 (1H, d, J=1.2Hz), 7.87 (1H, s).

EXAMPLE 19

(1) Synthesis of
5-[2-[3-(hydroxy)propylcarbamoyloxy]ethylthio]imidazo[1,2-a]pyridine (Compound 123)

To 5-[2-(phenoxycarbonyloxy)ethylthio]imidazo[1,2-a]pyridine (1.10 g, 3.50 mmoles) was added 3-aminopropanol (0.27 ml, 3.52 mmoles) and the mixture was stirred at 120° C. for 1.5 hours. The reaction mixture was cooled by standing and chloroform was added thereto, which was washed with water and dried over anhydrous magnesium sulfate, and then the solvent was distilled off. Then, the residue was purified by column chromatography (eluent: methanol/chloroform=1:20) to obtain 575 mg of the desired product (55.6%, colorless crystals).

Elemental analysis for C$_{13}$H$_{17}$N$_3$O$_3$S.0.2H$_2$O, Calcd.: C, 52.23; H, 5.87; N, 14.06. Found: C, 52.46; H, 5.78; N, 14.26.

NMR (200MHz, CDCl$_3$) δ: 1.66 (2H, m), 2.82 (1H, br), 3.15-3.32 (4H, m), 3.66 (2H, t, J=5.6Hz), 4.27 (2H, t, J=6.2Hz), 4.81 (1H, br], 7.07 (1H, dd, J=7, 1.2Hz), 7.18 (1H, dd, J=9, 7Hz), 7.61 (1H, d, J=9Hz), 7.70 (1H, d, J=1.4Hz), 7.90 (1H, s).

According to the same manner as that described in Example 19 (1), the following compounds were obtained.

(2)

5-[2-[6-Hydroxy)hexylcarbamoyloxy]ethylthio]imidazo[1,2-a]pyridine (Compound 124)

Elemental analysis for C$_{16}$H$_{23}$N$_3$O$_3$S.0.2H$_2$O, Calcd.: C, 56.35; H, 6.92; N, 12.32. Found: C, 56.63; H, 6.89; N, 12.43.

NMR (200MHz, CDCl$_3$) δ: 1.22-1.65 (8H, m), 2.16 (1H, br), 3.10 (2H, m), 3.21 (2H, t, J=6.2Hz), 3.64 (2H, t, J=6.2Hz), 4.26 (2H, t, J=6.2Hz). 4.48 (1H, br), 7.05 (1H, dd, J=7, 1.2Hz), 7.17 (1H, dd, J=8.8, 7Hz), 7.60 (1H, m), 7.70 (1H, d, J=1.4Hz), 7.89 (1H, m).

(3)

5-[2-[3-Morphlino)propylcarbamoyloxy]ethylthio]imidazo[1,2-a]pyridine (Compound 125)

NMR (200MHz, (CDCl$_3$) δ: 1.66 (2H, m), 2.35-2.48 (6H, m), 3.16-3.30 (4H, m), 3.65-3.75 (4H, m), 4.26 (2H, t, J=6.4Hz), 5.77 (1H, br), 7.05 (1H, dd, J=7, 1Hz). 7.17 (1H, dd, J=9, 7Hz), 7.61 (1H, d, J=9Hz), 7.72 (1H, d, J=1.2Hz), 7.89 (1H, s).

(4)

5-[2-[3-(1-Imidazolyl)propylcarbamoyloxy]ethylthio]imidazo[1,2-a]pyridine (Compound 126)

NMR (200MHz, (CDCl$_3$) δ: 1.96 (2H, q, J=6.8Hz), 3.06-3.27 (4H, m), 3.97 (2H, t, J=6.8Hz), 4.27 (2H, t, J=6.2Hz), 5.06 (1H, br), 6.93 (1H, s), 7.05 (1H, d, J=7Hz), 7.07 (1H, s), 7.17 (1H, m), 7.48 (1H, s), 7.61 (1H, dd, J=9, 0.8Hz), 7.71 (1H, s), 7.89 (1H, s).

(5)

5-[2-[4-(Pyridyl)methylcarbamoyloxy]ethylthio]imidazo[1,2-a]pyridine (Compound 127)

NMR (200MHz, CDCl$_3$) δ: 3.23 (2H, t, J=6.2Hz), 4.25-4.40 (4H, m), 5.36 (1H, br), 7.05 (1H, d, J=7Hz), 7.10-7.20 (2H, m), 7.60 (1H, d, J=9Hz), 7.70 (1H, d, J=1Hz). 7.90 (1H, s), 7.90 (1H, s), 8.56 (2H, m).

EXAMPLE 20

(1) Synthesis of
5-[2-(methoxycarbonylamino)ethylthio]imidazo[1,2-a]pyridine (Compound 128)

To a solution of 5-[2-(amino)ethylthio]imidazo[1,2-a]pyridine (1.93 g, 10 mmoles) and triethylamine (1.53 ml, 11 mmoles) in methylene chloride (30 ml) was added methyl chloroformate (0.77 ml, 10 mmoles) under ice-cooling with stirring and the mixture was stirred at room temperature for 20 minutes. The reaction mixture was washed in turn with an aqueous sodium bicarbonate solution and water, dried over anhydrous magnesium sulfate, and then the solvent was distilled off. The residue was purified by column chromatography (eluent: ethanol/ethyl acetate=1:10) to obtain 1.68 g of the desired product (66.9%, colorless crystals).

Melting point: 198.0°-200.0° C.

Elemental analysis for C$_{11}$H$_{13}$N$_3$O$_2$S, Calcd.: C, 52.57; H, 5.21; N, 16.72. Found: C, 52.68; H, 5.22; N, 16.60.

NMR (200MHz, CDCl$_3$) δ: 3.12 (2H, m), 3.40 (2H, m), 3.68 (3H, s), 5.10 (1H, br), 7.00 (1H, d, J=7Hz), 7.16 (1H, dd, J=9, 7Hz). 7.61 (1(, d, J=9Hz), 7.72 (1H, s), 7.87 (1H, s).

According to the same manner as that described in Examples 2 and 20 (1), the following compounds were obtained.

(2)
5-[2-(Ethoxycarbonylamino)ethylthio]imidazo[1,2-a]pyridine (Compound 129)

Melting point: 68°-70° C.
Elemental analysis for $C_{12}H_{15}N_3O_2S$, Calcd.: C, 54.32; H, 5.70; N, 15.84. Found: C, 54.43; H, 5.75; N, 15.83.

(3)
5-[2-(Propyloxycarbonylamino)ethylthio]imidazo[1,2-a]pyridine (Compound 130)

Melting point: 62°-64° C.
Elemental analysis for $C_{13}H_{17}N_3O_2S$, Calcd.: C, 55.89; H, 6.13; N, 15.04. Found: C, 55.87; H, 6.09; N, 14.96.

NMR (200MHz, (CDCl$_3$) δ: 0.92 (3H, t, J=7.4Hz), 1.62 (2H, m), 3.14 (2H, t, J=6.6Hz), 3.42 (1H, m), 4.01 (1H, t, J=6.6Hz), 5.07 (1H, br), 7.02 (1H, d, J=7Hz), 7.17 (1H, dd, J=9, 7Hz), 7.60 (1H, d, J=9Hz), 7.71 (1H, d, J=1.2Hz), 7.86 (1H, s).

IR (KBr) cm$^{-1}$: 3210, 3025, 2965, 1695, 1620, 1545, 1490, 1275.

(4)
5-[2-(Butyloxycarbonylamino)ethylthio]imidazo[1,2-a]pyridine (Compound 131)

Melting point: 75°-76° C.
Elemental analysis for $C_{14}H_{19}N_3O_2S$, Calcd.: C, 57.31; H, 6.53; N, 14.32. Found: C, 57.32; H, 6.55; N, 14.23.

NMR (200MHz, CDCl$_3$) δ: 0.93 (3H, t, J=7Hz), 1.35 (2H, m), 1.58 (2H, m), 3.14 (2H, t, J=6.4Hz), 3.41 (2H, m), 4.05 (2H, t, J=6.6Hz), 5.04 (1H, br), 7.16 (1H, dd, J=9, 7Hz), 7.60 (1H, d, J=9Hz), 7.71 (1H, d, J=1.2Hz), 7.85 (1H, s).

IR (KBr) cm$^{-1}$: 3490, 3210, 2970, 1695, 1615, 1500, 1285.

(5)
5-[2-(Isopropyloxycarbonylamino)ethylthio]imidazo[1,2-a]pyridine (Compound 132)

Melting point: 80.0°-81.0° C.
Elemental analysis for $C_{13}H_{17}N_3O_2S$, Calcd.: C, 55.89; H, 6.13; N, 15.04. Found: C, 55.85; H, 6.14; N, 14.96.

NMR (200MHz, CDCl$_3$) δ: 1.22 (6H, t, J=6.2Hz), 3.14 (2H, t, J=6.4Hz), 3.41 (2H, m), 4.94 (1H, br), 7.02 (1H, d, J=7Hz), 7.17 (1H, dd, J=9, 7Hz), 7.61 (1H, d, J=9Hz), 7.71 (1H, d, J=1.4Hz), 7.86 (1H, s).

IR (KBr) cm$^{-1}$: 3220, 3025, 2970, 1705, 1630, 1545, 1300, 1240.

(6)
5-[2-(Isopropyloxycarbonyl)ethylthio]imidazo[1,2-a]pyridine.hydrochloride (Compound 133)

Melting point: 145°-150° C.

(7)
5-[2-(Isobutyloxycarbonylamino)ethylthio]imidazo[1,2-a]pyridine (Compound 134)

Melting point: 75°-76° C.
Elemental analysis for $C_{14}H_{19}N_3O_2S$, Calcd.: C, 57.31; H, 6.53; N, 14.32. Found: C, 57.29; H, 6.53; N, 14.41.

NMR (200MHz, CDCl$_3$) δ: 0.91 (6H, d, J=6.8Hz), 1.89 (1H, m), 3.14 (2H, t, J=6.4Hz), 3.42 (2H, m), 3.84 (2H, d, J=6.6Hz), 5.15 (1H, br), 7.01 (1H, d, J=7Hz), 7.16 (1H, dd, J=9, 7Hz), 7.59 (1H, d, J=9Hz), 7.70 (1H, d, J=1.2Hz), 7.85 (1H, s).

(8)
5-[2-(Allyloxycarbonylamino)ethylthio]imidazo[1,2-a]pyridine (Compound 135)

Melting point: 72.5°-73.5° C.
Elemental analysis for $C_{13}H_{15}N_3O_2S$, Calcd.: C, 56.30; H, 5.45; N, 15.15. Found: C, 56.34; H, 5.44; N, 15.04.

NMR (200MHz, CDCl$_3$) δ: 3.15 (2H, t, J=6.4Hz), 3.43 (2H, m), 4.56 (2H, m), 5.07 (1H, br), 5.18-5.36 (2H, m), 5.90 (1H, m), 7.02 (1H, d, J=7Hz), 7.17 (1H, dd, J=9, 7Hz), 7.61 (1H, d, J=9Hz), 7.72 (1H, d, J=1.4Hz), 7.86 (1H, m).

IR (KBr) cm$^{-1}$: 3205, 3020, 1700, 1625, 1570, 1490, 1270.

(9)
5-[2-[2,2,2-(Trichloro)ethoxycarbonylamino]ethylthio]imidazo[1,2-a]pyridine (Compound 136)

Melting point: 113°-114.0° C.
Elemental analysis for $C_{12}H_{12}N_3O_2SCl_3$, Calcd.: C, 39.10; H, 3.28; N, 11.40. Found: C, 39.23; H, 3.27; N, 11.25.

NMR (200MHz, CDCl$_3$) δ: 3.17 (2H, t, J=6.4Hz), 3.48 (2H, m), 4.73 (2H, s), 5.52 (1H, br), 7.03 (1H, d, J=7Hz), 7.17 (1H, dd, J=9, 7Hz), 7.62 (1H, d, J=9Hz), 7.71 (1H, d, J=1.2Hz), 7.87 (1H, m).

IR (KBr) cm$^{-1}$: 3195, 2975, 1725, 1615, 1545, 1485, 1260, 1210.

(10) 5-[2-(Benzyloxycarbonylamino)ethylthio]imidazo[1,2-a]pyridine (Compound 137)

Melting point: 52°-53° C.
Elemental analysis for $C_{17}H_{17}N_3O_2S$, Calcd.: C, 62.36; H, 5.23; N, 12.83. Found: C, 62.34; H, 5.22; N, 12.75.

NMR (200MHz, CDCl$_3$) δ: 3.14 (2H, t, J=6.4Hz), 3.43 (2H, m), 5.09 (2H, s), 5.17 (1H, br), 6.99 (1H, d, J=6.8Hz), 7.13 (1H, dd, J=9.2, 6.8Hz), 7.35 (5H, s), 7.59 (1H, d, J=9.2Hz), 7.69 (1H, s), 7.84 (1H, s).

(11)
5-[2-[(9-Fluorenyl)methyloxycarbonylamino]ethylthio]imidazo[1,2-a]pyridine (Compound 138)

Melting point: 105.0°-108.0° C.
Elemental analysis for $C_{25}H_{21}N_3O_2S.0.4H_2O$, Calcd.: C, 69.07; H, 5.05; N, 9.67. Found: C, 69.14; H, 5.23; N, 9.96.

NMR (200MHz, CDCl$_3$) δ: 3.13 (2H, t, J=6Hz), 3.42 (2H, m), 4.21 (1H, t, J=6.6Hz), 4.43 (2H, d, J=6.6Hz), 5.17 (1H, br), 7.01 (1H, d, J=7.4Hz), 7.15 (1H, dd, J=8.6, 7.4Hz), 7.29-7.46 (4H, m), 7.53-7.65 (3H, m), 7.60-7.87 (4H, m).

IR (KBr) cm$^{-1}$: 3205, 3020, 1710, 1625, 1550, 1485, 1450, 1270.

(12)
5-[2-(Phenoxycarbonylamino)ethylthio]imidazo[1,2-a pyridine (Compound 139)

Melting point: 96.0°-97.0° C.
Elemental for $C_{16}H_{15}N_3O_2S$, Calcd.: C, 61.32; H, 4.82; N, 13.41. Found: C, 61.35; H, 4.86; N, 13.30.

IR (KBr) cm$^{-1}$: 3200, 3005, 1725, 1615, 1555, 1485, 1270, 1210.

(13) 5-[2-(N-Methyl-N-isopropyloxycarbonylamino)ethylthio]imidazo[1,2-a]pyridine (Compound 140)

NMR (200MHz, CDCl$_3$) δ: 1.02-1.35 (6H, m), 2.91 (3H, s), 3.05-3.26 (2H, m), 3.38-3.60 (2H, m), 4.89 (1H, m), 7.01 (1H, br), 7.18 (1H, dd, J=9, 7Hz), 7.60 (1H, d, J=9Hz), 7.71 (1H, s), 7.84 (1H, s).

IR (KBr) cm$^{-1}$: 3220, 3025, 2970, 1705, 1630, 1545

(14) 5-[2-(N-Ethyl-N-isopropyloxycarbonylamino)ethylthio]imidazo[1,2-a]pyridine (Compound 141)

NMR (200MHz, (CDCl$_3$) δ: 0.95-1.35 (9H, m), 3.02-3.68 (6H, m), 4.90 (1H, m), 7.04 (1H, m), 7.19 (1H, dd, J=9, 7Hz), 7.60 (1H, d, J=9Hz), 7.72 (1H, s), 7.83 (1H, s).

IR (KBr) cm$^{-1}$: 3220, 3025, 2970, 1705, 1630, 1545.

EXAMPLE 21

(1) According to the same manner as that described in Example 4 (1), the following compounds were obtained.

3-Bromo-5-[2-(isopropyloxycarbonylamino)ethylthio]imidazo[1,2-a]pyridine (Compound 142)

Melting point: 103.0°-104.0° C.
Elemental analysis for C$_{13}$H$_{16}$N$_3$O$_2$SBr, Calcd.: C, 43.58; H, 4.50; N, 11.73. Found: C, 43.60; H, 4.53; N, 11.74.

NMR (200MHz, CDCl$_3$) δ: 1.22 (6H, d, J=6.2Hz), 3.11 (2H, t, J=6.6Hz), 3.42 (2H, m), 4.90 (1H, heptet, J=6.2Hz), 4.96 (1H, br), 7.00 (1(, dd, J=7, 1.2Hz), 7.14 (1H, dd, J=8.8, 7Hz), 7.57 (1H, dd, J=8.8, 1.2Hz), 7.59 (1H, s).

(2) 3-Chloro-5-[2-(isopropyloxycarbonylamino)ethylthio]imidazo[1,2-a]pyridine (Compound 143)

Melting point: 113.0°-114.0° C.
Elemental for C$_{13}$H$_{16}$N$_3$O$_2$SCl.0.2H$_2$O, Calcd.: C, 49.19; H, 5.21; N, 13.24. Found: C, 49.38; H, 5.26; N, 13.22.

NMR (200MHz, CDCl$_3$) δ: 1.22 (6H, d, J=6.4Hz), 3.12 (2H, t, J=6.4Hz), 3.43 (2H, m), 4.90 (1H, heptet, J=6.4Hz), 4.96 (1H, br), 6.99 (1H, dd, J=7.2, 1.2Hz), 7.10 (1H, dd, J=8.8, 7.2Hz), 7.53 (1H, dd, J=8.8, 1.2Hz), 7.54 (1H, s).

EXAMPLE 22

According to the same manner as that described in Example 5, the following compound was obtained.

5-[2-(Isopropyloxycarbonylamino)ethylthio]-3-(morpholinomethyl)imidazo[1,2-a]pyridine (Compound 144)

NMR (200MHz, CDCl$_3$) δ: 0.96 (6H, d, J=6.2Hz), 2.56 (4H, m), 3.26 (2H, m), 3.36 (2H, m), 3.65 (4H, m), 4.10 (2H, s), 4.59 (1H, heptet, J=6.2Hz), 6.85 (1H, br), 7.01 (1H, d, J=5Hz), 7.13 (1H, dd, J=8.6, 6.6Hz), 7.51 (1H, s), 7.53 (1H, d, J=8.6Hz).

EXAMPLE 23

(1) According to the same manner as that described in Example 20 (1), the following compounds were obtained.

5-[3-(Methoxycarbonylamino)propylthio]imidazo[1,2-a]pyridine (Compound 145)

Melting point: 69.0°-70.0° C.

Elemental analysis for C$_{12}$H$_{15}$N$_3$O$_2$S, Calcd.: C, 54.32; H, 5.70; N, 15.84. Found: C, 54.48; H, 5.74; N, 15.72.

NMR (200MHz, CDCl$_3$) δ: 1.85 (2H, m), 3.02 (2H, t, J=7Hz), 3.32 (2H, m), 3.67 (3H, s), 4.85 (1H, br), 6.91 (1H, dd, J=7, 1.2Hz), 7.15 (1H, dd, J=9, 7Hz), 7.58 (1H, d, J=9Hz), 7.70 (1H, d, J=1.2Hz), 7.84 (1H, s).

(2) 5-[3-(Isopropyloxycarbonylamino)propylthio]imidazo[1,2-a]pyridine (Compound 146)

NMR (200MHz, CDCl$_3$) δ: 1.22 (6H, d, J=6.2Hz), 1.85 (2H, m), 3.03 (2H, m), 3.31 (2H, m), 4.82 (1H, br), 4.90 (1H, heptet, J=6.2Hz), 6.90 (1H, dd, J=7, 1Hz), 7.15 (1H, dd, J=9, 7Hz), 7.57 (1H, m), 7.69 (1H, d, J=1.4Hz), 7.84 (1H, m).

IR (KBr) cm$^{-1}$: 3210, 3025, 2965, 1695, 1620, 1545, 1490, 1275.

(3) 5-[1-(tert-Butoxycarbonyl)-4-piperidylthio]imidazo[1,2-a]pyridine (Compound 147)

NMR (200MHz, CDCl$_3$) δ: 1.45 (9H, s), 1.50-1.98 (4H, m), 2.90 (2H, m), 3.36 (1H, m), 3.98 (2H, m), 7.03 (1H, dd, J=7, 1.2Hz), 7.15 (1H, dd, J=9, 7Hz), 7.64 (1H, m), 7.70 (1H, d, J=1.2Hz), 7.96 (1H, m).

(4) 5-[1-(Isopropyloxycarbonyl)-4-piperidylthio]imidazo[1,2-a]pyridine (Compound 148)

NMR (200MHz, CDCl$_3$) δ: 1.23 (6H, d, J=6.2Hz), 1.50-1.98 (4H, m), 2.94 (2H, m), 3.37 (1H, m), 4.03 (2H, m), 4.91 (1H, heptet, J=6.2Hz), 7.03 (1H, dd, J=7, 1.2Hz), 7.16 (1H, dd, J=9, 7Hz), 7.65 (1H, d, J=9Hz), 7.71 (1H, d, J=1.2Hz), 7.97 (1H, s).

EXAMPLE 24

(1) Synthesis of 5-[2-(tert-butoxycarbonylamino)ethoxy]imidazo[1,2-a]pyridine (Compound 149)

To a suspension of 60% sodium hydride (oily; 4.8 g, 0.12 mmoles) in DMF (150 ml) was added a solution of 5-chloroimidazo[1,2-a]pyridine (15.26 g, 0.1 moles) and 2-aminoethanol (6.72 g, 0.11 mole) in DMF (120 ml) with stirring at room temperature and the mixture was stirred at the same temperature for 33 hours. To the reaction mixture was added di-tert-butyl dicarbonate (32.74 g, 0.15 moles), followed by stirring at room temperature for 13 hours. After the solvent was distilled off, water (800 ml) was added to the residue, which was extracted twice with ether. The extract was washed with water, dried over anhydrous magnesium sulfate and concentrated, and then ether was added. The crystals precipitated were filtered off and washed with ether to obtain 10.77 g of the desired product (38.8%, colorless crystals). As second crystals, 1.31 g or the desired product was obtained (4.7%, colorless crystals).

NMR (200MHz, CDCl$_3$) δ: 1.46 (9H, s), 3.68 (2H, s), 4.31 (2H, t, J=5.2Hz), 5.00 (1H, br), 6.06 (1H, d, J=7Hz), 7.17 (1H, dd, J=9, 7Hz), 7.30 (1H, d, J=9Hz), 7.60 (1H, d, J=1.2Hz), 7.66 (1H, s).

According to the same manner as that described in Example 24 (1), the following compound was obtained.

(2)
5-[3-(tert-Butoxycarbonyl)propoxy]imidazo[1,2-a]pyridine (compound 150)

NMR (200MHz, CDCl$_3$) δ: 1.44 (9H, s), 2.14 (2H, q, J=6.2Hz), 3.40 (2H, m), 4.31 (2H, t, J=6.2Hz), 4.83 (1H, br), 6.04 (1H, d, J=7.2Hz), 7.16 (1H, dd, J=9, 7.2Hz), 7.28 (1H, d, J=9Hz), 7.59 (1H, d, J=1.2Hz), 7.66 (1H, s).

EXAMPLE 25

(1) Synthesis of 5-[2-(tert-butoxycarbonylamino)ethylsulfonyl]imidazo[1,2-a]pyridine (Compound 151) and 5-[2-(tert-butoxycarbonylamino)ethylsulfinyl]imidazo[1,2-a]pyridine (Compound 152)

To a solution of 5-[2-(tert-butoxycarbonylamino)ethylthio]imidazo[1,2-a]pyridine (2.93 g, 10 mmoles) in chloroform (50 ml) was added 85% m-chloroperbenzoic acid (5.08 g, 25 mmoles) under ice-cooling with stirring and the mixture was stirred at room temperature for 4 hours. Then, chloroform (50 ml) was added to the mixture, which was washed in turn with an aqueous sodium bicarbonate solution and saturated saline, dried over anhydrous magnesium sulfate and the solvent was distilled off. The residue was purified by column chromatography (eluent: ethyl acetate) to obtain 560 mg of 5-[2-(tert-butoxycarbonylamino)ethylsulfonyl]imidazo[1,2-a]pyridine (Compound 151; 17.2%, colorless crystals) as Fraction 1.

Elemental analysis for $C_{14}H_{19}N_3O_2S.0.3H_2O$, Calcd.: C, 50.83; H, 5.97; N, 12.70. Found: C, 50.97; H, 5.91; N, 12.80.

NMR (200MHz, CDCl$_3$) δ: 1.37 (9H, s), 3.42–3.63 (4H, m), 5.03 (1H, br), 7.36 (1H, dd, J=9.7Hz), 7.68 (1H, dd, J=7, 1.5Hz), 7.85 (1H, d, J=1.5Hz), 7.96 (1H, d, J=9Hz), 8.25 (1H, m).

As Fraction 2, 5-[2-(tert-butoxycarbonylamino)ethylsulfinyl]imidazo[1,2-a]pyridine (Compound 152; 27.5%, colorless crystals) was obtained.

Elemental analysis for $C_{14}H_{19}N_3O_4S.0.4H_2O$, Calcd.: C, 53.11; H, 6.30; N, 13.27. Found: C, 53.27; H, 6.18; N, 13.36.

NMR (200MHz, CDCl$_3$) δ: 1.43 (9H, s), 3.14–3.75 (4H, m), 5.07 (1H, br), 7.30–7.41 (2H, m), 7.73–7.87 (3H, m).

EXAMPLE 26

Synthesis of 5-(phthalimidomethylthio)imidazo[1,2-a]pyridine (Compound 153)

To a suspension of 5-mercaptoimidazo[1,2-a]pyridine (3.00 g, 20 mmoles) and N-bromomethylphthalimide (5.28 g, 22 mmoles) in ethanol (200 ml) was added triethylamine (4.2 ml, 30 mmoles) and the mixture was stirred at room temperature for 1 hour. After the solvent was distilled off, chloroform was added to the residue, which was washed with water, dried over anhydrous magnesium sulfate and the solvent was distilled off. Then, the residue was purified by column chromatography (eluent: ethyl acetate) to obtain 4.29 g of the desired product (69.4%, pale yellow crystals).

NMR (200MHz, CDCl$_3$) δ: 5.10 (2H, s), 7.02–7.13 (2H, m), 7.61–7.84 (6H, m), 7.99 (1H, m).

EXAMPLE 27

Synthesis of 5-[2-(phthalimido)ethylthio]imidazo[1,2-a]pyridine (Compound 99)

To a suspension of 5-mercaptoimidazo[1,2-a]pyridine (3.00g, 20 mmoles) and N-[2-(bromo)ethyl]phthalimide (5.59 g, 22 mmoles) in ethanol (200 ml) was added triethylamine (4.2 ml, 30 mmoles) and the mixture was stirred at room temperature for 3 hours and heated at reflux for 4 hours. After the solvent was distilled off, chloroform was added to the residue, which was washed with water, dried over anhydrous magnesium sulfate and the solvent was distilled off. Then, the residue was purified by column chromatography (eluent: ethyl acetate) to obtain 3.95 g of the desired product (61.1%, yellow crystals).

NMR (200MHz, CDCl$_3$) δ: 3.33 (2H, t, J=6.6Hz), 3.97 (2H, t, J=6.6Hz), 7.11–7.21 (2H, m), 7.55 (1H, m), 7.67–7.87 (6H, m).

EXAMPLE 28

Synthesis of 5-[3-(phthalimido)propylthio]imidazo[1,2-a]pyridine (Compound 154)

To a suspension of 5-mercaptoimidazo[1,2-a]pyridine (3.00g, 20 mmoles) and N-[3-(bromo)propyl]phthalimide (5.90 g, 22 mmoles) in ethanol (200 ml) was added triethylamine (4.2 ml, 30 mmoles) and the mixture was stirred at room temperature for 1 hour and heated at reflux for 1 hour. After the solvent was distilled off, chloroform was added to the residue, which was washed with water, dried over anhydrous magnesium sulfate and the solvent was distilled off. Then, the residue was purified by column chromatography (eluent: ethyl acetate) to obtain 4.79 g of the desired product (71.1%, colorless crystals).

NMR (200MHz, CDCl$_3$) δ: 2.02 (2H, m), 3.02 (2H, t, J=7.2Hz), 3.85 (2H, t, J=6.8Hz), 6.98 (1H, dd, J=7, 1Hz), 7.16 (1H, dd, J=9, 7Hz), 7.58 (1H, m), 7.67–7.88 (6H, m).

EXAMPLE 29

Synthesis of 5-[4-(phthalimido)butylthio]imidazo[1,2-a]pyridine (Compound 155)

To a suspension of 5-mercaptoimidazo[1,2-a]pyridine (3.00g, 20 mmoles) and N-[4-(bromo)butyl]phthalimide (6.21 g, 22 mmoles) in ethanol (200 ml) was added triethylamine (4.2 ml, 30 mmoles) and the mixture was stirred at room temperature for 1 hour and heated at reflux for 45 minutes. After the solvent was distilled off, chloroform was added to the residue, which was washed with saturated saline, dried over anhydrous magnesium sulfate and the solvent was distilled off. Then, the residue was purified by column chromatography (eluent: ethyl acetate) to obtain 4.50 g of the desired product (64.1%, pale yellow crystals).

NMR (200MHz, CDCl$_3$) δ: 1.62–1.95 (4H, m), 3.04 (2H, t, J=7Hz), 3.71 (2H, t, J=6.8Hz), 6.89 (1H, dd, J=7, 1Hz), 7.10 (1H, dd, J=9, 7Hz), 7.54 (1H, d, J=9Hz), 7.65–7.86 (6H, m).

EXAMPLE 30

Synthesis of 5-[6-(phthalimido)hexylthio]imidazo[1,2-a]pyridine (Compound 156)

To a suspension of 5-mercaptoimidazo[1,2-a]pyridine (1.50g, 10 mmoles) and N-[6-(bromo)hexyl]phthalimide (3.10 g, 10 mmoles) in ethanol (100 ml) was added triethylamine (2.1 ml, 15 mmoles) and the mixture was stirred at room temperature for 12 hours. After the solvent was distilled off, chloroform was added to the residue, which was washed with water, dried over anhydrous magnesium sulfate and the solvent was distilled off. Then the residue was purified by column chromatography (eluent: ethyl acetate) to obtain 2.86 g of the desired product (75.5%, light tan solid).

NMR (200MHz, CDCl$_3$) δ: 1.24–1.77 (8H, m), 2.99 (2H, t, J=7.2Hz), 3.68 (2H, t, J=7.2Hz), 6.87 (1H, dd, J=7, 1Hz), 7.15 (1H, dd, J=9, 7Hz), 7.56 (1H, d, J=9Hz), 7.65–7.88 (6H, m).

EXAMPLE 31

Synthesis of 5-[2-[2-(phthalimido)ethyloxy]ethylthio]imidazo[1,2-a]pyridine (Compound 157)

To a suspension of 5-mercaptoimidazo[1,2-a]pyridine (3.00g, 20 mmoles) and N-[2-[2-(bromo)ethyloxy]ethyl]phthalimide (5.96 g, 20 mmoles) in ethanol (200 ml) was added triethylamine (4.2 ml, 30 mmoles) and the mixture was stirred at room temperature for 12 hours and heated at reflux for 3 hours. After the solvent was distilled off, chloroform was added to the residue, which was washed with water, dried over anhydrous magnesium sulfate and the solvent was distilled off. Then, the residue was purified by column chromatography (eluent: ethyl acetate) to obtain 4.00 g of the desired product (54.5%, light tan solid).

NMR (200MHz, CDCl$_3$) δ: 3.12 (2H, t, J=6.4Hz), 3.64–3.77 (4H, m), 3.89 (2H, t, J=5.4Hz), 6.91 (1H, dd, J=7.1Hz), 7.20 (1H, dd, J=9, 7Hz), 7.56 (1H, d, J=9Hz), 7.63–7.88 (6H, m).

EXAMPLE 32

According to the same manner as that described in Example 31, the following compounds were obtained.

(1)

5-[3-[[2-(Anilino)ethyl]-N-(acetyl)amino]propylthio]imidazo[1,2-a]pyridine (Compound 158)

NMR (200MHz, CDCl$_3$) δ: 1.89 (2H, m), 2.05 and 2.09 (each 1.5H, s), 2.97 (2H, m), 3.25–3.60 (6H, m), 6.53–6.63 (2H, m), 6.63–6.80 (1H, m), 6.89 (1H, m), 7.07–7.25 (3H, m), 7.59 (1H, m), 7.70 (1H, m), 7.83 (1H, s).

(2)

5-[3-[[2-N-(acetyl)anilino]ethyl]-N-(acetyl)amino]propylthio]imidazo[1,2-a]pyridine (Compound 159)

NMR (200MHz, CDCl$_3$) δ: 1.70–2.07 (8H, m), 2.88–3.06 (2H, m), 3.32–3.58 (4H, m), 3.70–3.85 (2H, m), 6.88–7.00 (1H, m), 7.08–7.26 (3H, m), 7.32–7.50 (3H, m), 7.57–7.68 (1H, m), 7.68–7.74 (1H, m), 7.80–7.88 (1H, m).

(3)

5-[3-[[2-(anilino)ethyl]-N-(tert-butoxycarbonyl)amino]propylthio]imidazo[1,2-a]pyridine (Compound 160)

NMR (200MHz, CDCl$_3$) δ: 1.45 (9H, s), 1.87 (2H, m), 2.96 (2H, t, J=7.2Hz), 3.27 (2H, m), 3.34 (2H, m), 6.52–6.62 (2H, m), 6.69 (1H, dd, J=9, 7.4Hz), 6.85 (1H, d, J=7.4Hz), 7.07–7.22 (3H, m), 7.56 (1H, m), 7.69 (1H, d, J=1.4Hz), 7.81 (1H, s).

(4)

5-[3-[[2-[N-(acetyl)anilino]ethyl]-N-(tert-butoxycarbonyl)amino]propylthio]imidazo[1,2-a]pyridine (Compound 161)

NMR (200MHz, CDCl$_3$) δ: 1.13–1.48 (9H, m), 1.72–1.98 (5H, m), 2.97 (2H, t, J=7.2Hz), 3.38 (4H, m), 3.75 (2H, m), 6.94 (1H, d, J=7Hz), 7.08–7.47 (6H, m), 7.61 (1H, d, J=9Hz), 7.70 (1H, d, J=1.2Hz), 7.85 (1H, m).

EXAMPLE 33

Synthesis of 5-[2-[2-(hydroxy)benzoylamino]ethylthio]imidazo[1,2-a]pyridine (Compound 162)

To a solution of 5-[2-(amino)ethylthio]imidazo[1,2-a]pyridine (3.87 g, 20 mmoles) and triethylamine (5.58 ml, 40 mmoles) in methylene chloride (200 ml) was added o-acetylsalicyloyl chloride (4.77 g, 24 mmoles) under ice-cooling with stirring and the mixture was stirred at room temperature for 30 minutes. After the solvent was distilled off, ethanol (60 ml) and 1N NaOH (40 ml) were added to the residue, followed by stirring for 1 hour. 1N HCl (40 ml) was added and ethanol was distilled off, and then the residue was extracted with chloroform and dried over anhydrous magnesium sulfate. After the solvent was distilled off, the residue was purified by column chromatography (eluent: ethyl acetate/ethanol=10:1) to obtain 3.51 g of the desired product (56.0%, colorless solid).

Melting point: 156°–157° C.

Elemental analysis for C$_{16}$H$_{15}$N$_3$O$_2$S, Calcd.: C, 61.32; H, 4.82; N, 13.41. Found: C, 61.44; H, 5.04; N, 13.45.

NMR (200Hz, DMSO-d$_6$) δ: 3.34 (2H, m), 3.58 (2H, m), 6.83–6.93 (2H, m), 7.18 (1H, dd, J=7, 1.2Hz), 7.27 (1H, dd, J=8.6, 7.0Hz), 7.39 (1H, m), 7.54 (1H, m), 7.68 (1H, d, J=1.2Hz), 7.77 (1H, m), 7.95 (1H, d, J=1.2Hz), 9.04 (1H, br).

EXAMPLE 34

Synthesis of 5-[2-[2H-1,3-benzoxazine-2-thion-4(3H)-on-3-yl]ethylthio]imidazo[1,2-a]pyridine (Compound 163)

To a suspension of 5-[2-[2-(hydroxy)benzoylamino]ethylthio]imidazo[1,2-a]pyridine (627 mg, 2.00 mmoles) in dry tetrahydrofuran (30 ml) was added 1,1'-thiocarbonyldiimidazole (713 mg, 4.00 mmoles) and the mixture was stirred at room temperature for 46 hours. After the solvent was distilled off, chloroform was added to the residue, which was washed with water and dried over anhydrous magnesium sulfate. After the solvent was distilled off, the residue was purified by column chromatography (eluent: ethyl acetate) to obtain 600 mg of the desired product. The product was recrystallized from methylene chloride-ethyl acetate to obtain 448 mg of the desired product (63.0%, light red powder).

NMR (200MHz, CDCl₃) δ: 3.45 (2H, m), 4.73 (2H, m), 7.15–7.47 (4H, m), 7.60 (1H, m), 7.71 (1H, d, J=1.4Hz), 7.75 (1H, m), 7.85 (1H, m), 8.04 (1H, m).

EXAMPLE 35

Synthesis of 5-[2-[2H-1,3-benzooxazine-2,4(3H)-dion-3-yl]ethylthio]imidazo[1,2-a]pyridine (Compound 164)

To a solution of 5-[2-[2-(hydroxy)benzoylamino]ethylthio]imidazo[1,2-a]pyridine (627 mg, 2.00 mmoles) in dry tetrahydrofuran (30 ml) was added 1,1'-carbonyldiimidazole (649 mg, 4.00 mmoles) and the mixture was stirred at room temperature for 15 hours. After the solvent was distilled off, chloroform was added to the residue, which was washed with water and dried over anhydrous magnesium sulfate. After the solvent was distilled off, the residue was purified by column chromatography (eluent: ethyl acetate) to obtain 528 mg of the desired product (77.8%, colorless crystals).

NMR (200MHz, CDCl₃) δ: 3.38 (2H, m), 4.34 (2H, m), 7.13–7.33 (3H, m), 7.39 (1H, m), 7.57 (1H, m), 7.67–7.78 (2H, m), 7.83 (1H, s), 8.05 (1H, dd, J=7.8, 1.8Hz).

EXAMPLE 36

Synthesis of 5-[1-(trifluoromethanesulfonyl)4-piperidylthio]imidazo[1,2-a]pyridine (Compound 165)

To a solution of 5-(4-piperidylthio)imidazo[1,2-a]pyridine dihydrochloride (919 mg, 3 mmoles) and triethylamine (1.39 ml, 9.89 mmoles) in methylene chloride (40 ml) was added trifluoromethanesulfonic anhydride (0.61 ml, 3.63 mmoles) under ice-cooling with stirring and the mixture was stirred at room temperature for 1 hour. The residue was washed with saturated saline and dried over anhydrous magnesium sulfate. After the solvent was distilled off, the residue was purified by column chromatography (eluent: ethyl acetate/n-hexane=1:1) to obtain 0.66 g of the desired product (60.2%, colorless solid).

Melting point: 102°–103° C.

NMR (200MHz, CDCl₃) δ: 1.68–1.90 (2H, m), 1.97–2.13 (2H, m), 3.22 (2H, m), 3.41 (1H, m), 3.89 (2H, m), 7.05 (1H, dd, J=7, 1.2Hz), 7.17 (1H, dd, J=8.8, 7Hz), 7.68 (1H, m), 7.72 (1H, d, J=1.2Hz), 7.95 (1H, m).

EXAMPLE 37

Synthesis of 5-[4-(methanesulfonamido)butylthio]imidazo[1,2-a]pyridine (Compound 166)

To a solution of 5-[4-(amino)butylthio]imidazo[1,2-a]pyridine (440 mg, 1.99 mmoles) and triethylamine (0.42 ml, 3.01 mmoles) in methylene chloride (20 ml) was added methanesulfonyl chloride (0.19 ml, 2.45 mmoles) under ice-cooling with stirring and the mixture was stirred under ice-cooling for 1 hour. The reaction mixture was washed in turn with an aqueous saturated sodium bicarbonate solution and saturated saline and dried over anhydrous magnesium sulfate. After the solvent was distilled off, the residue was purified by column chromatography (eluent: ethyl acetate) to obtain 302 mg of the desired product (50.8%, light red brown solid).

NMR (200MHz, CDCl₃) δ: 1.74 (4H, m), 2.94 (3H, s), 3.02 (2H, m), 3.15 (2H, m), 4.53 (1H, br), 6.92 (1H, dd, J=7.1Hz), 7.16 (1H, dd, J=9, 7Hz), 7.59 (1H, m), 7.70 (1H, d, J=1.2Hz), 7.84 (1H, m).

EXAMPLE 38

Synthesis of 5-[4-(trifluoromethanesulfonamido)butylthio]imidazo[1,2-a]pyridine (Compound 167)

To a solution of 5-[4-(amino)butylthio]imidazo[1,2-a]pyridine (460 mg, 2.08 mmoles) and triethylamine (0.44 ml, 3.16 mmoles) in methylene chloride (20 ml) was added trifluoromethanesulfonic anhydride (0.38 ml, 2.26 mmoles) under ice-cooling with stirring and the mixture was stirred under ice-cooling for 30 minutes. The reaction mixture was washed with water and dried over anhydrous magnesium sulfate. After the solvent was distilled off, the residue was purified by column chromatography (eluent: ethyl acetate) to obtain 277 mg of the desired product (37.7%, colorless crystals).

NMR (200MHz, CDCl₃) δ: 1.74 (4H, m), 3.04 (2H, m), 3.22 (2H, m), 6.94 (1H, dd, J=7, 1Hz), 7.19 (1H, dd, J=9, 7Hz), 7.56 (1H, d, J=9Hz), 7.69 (1H, d, J=1.2Hz), 7.86 (1H, m), 8.71 (1H, br).

EXAMPLE 39

Synthesis of 5-[4-(1-naphthalenesulfonylamino)butylthio]imidazo[1,2-a]pyridine (Compound 168)

To a solution of 5-[4-(amino)butylthio]imidazo[1,2-a]pyridine (300 mg, 1.36 mmoles) and triethylamine (0.29 ml, 2.08 mmoles) in methylene chloride (15 ml) was added 1-naphthalenesulfonyl chloride (307 mg, 1.35 mmoles) under ice-cooling with stirring and the mixture was stirred at room temperature for 1 hour. The reaction mixture was washed in turn with an aqueous sodium bicarbonate solution and water and dried over anhydrous magnesium sulfate. After the solvent was distilled off, the residue was purified by column chromatography (eluent: ethyl acetate) to obtain 296 mg of the desired product (53.0%, colorless solid).

NMR (200MHz, CDCl₃) δ: 1.55 (4H, m), 2.81 (2H, m), 2.92 (2H, m), 4.83 (1H, br), 6.78 (1H, dd, J=7, 1Hz), 7.11 (1H, dd, J=9, 7Hz), 7.45–7.75 (6H, m), 7.93 (1H, m), 8.05 (1H, d, J=8.4Hz), 8.25 (1H, dd, J=7.2, 1.2Hz), 8.62 (1H, m).

EXAMPLE 40

Synthesis of 5-[4-(isopropyloxycarbonylamino)butylthio]imidazo[1,2-a]pyridine (Compound 169)

To a solution of 5-[4-(amino)butylthio]imidazo[1,2-a]pyridine (370 mg, 1.67 mmoles) and triethylamine (0.35 ml, 2.51 mmoles) in metylene chloride (20 ml) was added isopropyl chloroformate (0.25 g, 2.04 mmoles) under ice-cooling with stirring and the mixture was stirred under ice-cooling for 1 hour. The reaction mixture was washed in turn with an aqueous sodium bicarbonate solution and saturated saline and dried over anhydrous magnesium sulfate. After the solvent was distilled off, the residue was purified by column chromatography (eluent: ethyl acetate) to obtain 215 mg of the desired product (41.8%, light tan oily product).

NMR (200MHz, CDCl₃) δ: 1.22 (6H, d, J=6.2Hz), 1.54–1.72 (4H, m), 3.02 (2H, m), 3.18 (2H, m), 4.66 (1H, br), 4.90 (1H, hept, J=6.2Hz), 6.90 (1H, dd, J=7, 1Hz), 7.15 (1H, dd, J=9, 7Hz), 7.58 (1H, d, J=9Hz), 7.84 (1H, m).

EXAMPLE 41

Synthesis of 5-[3-(benzenesulfonamido)propyloxy]imidazo[1,2-a]pyridine (Compound 170)

To a suspension of 5-[3-(amino)propyloxy]imidazo[1,2-a]pyridine dihydrochloride (2.64 g, 10 mmoles) and triethylamine (4.88 ml, 35 mmoles) in methylene chloride (100 ml)-acetonitrile (30 ml) was added benzenesulfonyl chloride (1.53 ml, 12 mmoles) under ice-cooling with stirring and the mixture was stirred at room temperature for 1 hour. The reaction mixture was washed in turn with an aqueous sodium bicarbonate solution and saturated saline and dried over anhydrous magnesium sulfate. After the solvent was distilled off, the crude product thus obtained was recrystallized from methylene-ethanol to obtain 1.97 g of the desired product (59.5%, light brown crystals).

Melting point: 155°-156° C.

NMR (200MHz, CDCl$_3$) δ: 2.14 (2H, m), 3.26 (2H, m), 4.27 (2H, t, J=5.8Hz), 5.93 (1H, dd, J=7, 1.2Hz), 6.08 (1H, br), 7.11 (1H, dd, J=9, 7Hz), 7.17 (1H, m), 7.33 (1H, m), 7.37-7.56 (4H, m), 7.84-7.92 (2H, m).

EXAMPLE 42

Synthesis of 5-[2-[2-(methanesulfonamido)ethyloxy]ethylthio]imidazo[1,2-a]pyridine (Compound 171)

To a suspension of 5-[2-[2-(phthalimido)ethyloxy]ethylthio]imidazo[1,2-a]pyridine (1.10 g, 3 mmoles) in ethanol (15 ml) was added hydrazine monohydrate (0.44 ml, 9.1 mmoles) and the mixture was heated at reflux for 1 hour. After the mixture was cooled by standing, methylene chlordie (30 ml) was added and an insoluble product was filtered off, and then the solvent was distilled off from the filtrate. Methylene chloride (30 ml) and triethylamine (0.84 ml, 6 mmoles) were added to the residue, to which was further added methanesulfonic anhydride (679 mg, 3.9 mmoles) under ice-cooling with stirring and the mixture was stirred at room temperature for 1 hour. Then, it was washed with saturated saline and dried over anhydrous magnesium sulfate. After the solvent was distilled off, the residue was purified by column chromatography (eluent: ethyl acetate/ethanol=10:1) to obtain 0.82 g of the desired product (86.9%, pale yellow oily product).

NMR (200MHz, CDCl$_3$) δ: 2.96 (3H, s), 3.16 (2H, t, J=6Hz), 3.22 (2H, m), 3.54 (2H, t, J=5Hz), 3.68 (2H, t, J=6Hz), 5.12 (1H, br), 6.99 (1H, dd, J=7, 6Hz), 7.16 (1H, dd, J=9, 7Hz), 7.61 (1H, m), 7.70 (1H, d, J=1.2Hz), 7.88 (1H, m).

EXAMPLE 43

Synthesis of 5-[3-[1,2-benzisothiazole-3(2H)-on-1,1-dioxido-2-yl]porpylthio]imidazo[1,2-a]pyridine (Compound 172)

To a solution of 5-[3-(chloro)propylthio]imidazo[1,2-a]pyridine (1.17 g, 5.16 mmoles) and saccharin (1.50 g, 8.19 mmoles) in DMF (30 ml) was added 1,8-diazabicyclo[5.4.0]-7-undecene (0.78 ml, 5.22 mmoles) and the mixture was stirred at 80° C. for 24 hours. The reaction mixture was poured into an aqueous sodium bicarbonate solution, which was extracted with ethyl acetate. The extract was washed with water and dried over anhydrous magnesium sulfate. After the solvent was distilled off, the residue was purified by column chromatography (eluent: ethyl acetate) to obtain 658 mg of the desired product (34.1%, colorless crystals).

Melting point: 99°-200° C.

NMR (200MHz, CDCl$_3$) δ: 2.17 (2H, m), 3.09 (2H, t, J=7Hz), 3.95 (2H, t, J=6.8Hz), 7.00 (1H, dd, J=7, 1Hz), 7.16 (1H, dd, J=8.8, 7Hz), 7.60 (1H, m), 7.69 (1H, d, J=1.2Hz), 7.80-7.97 (4H, m), 8.06 (1H, m).

EXAMPLE 44

Synthesis of 5-[3-(methanesulfonamido)benzyl]imidazo[1,2-a]pyridine (Compound 173)

To a solution of 3-aminobenzyl alcohol (1.23 g, 10 mmoles) and triethylamine (3.07 ml, 22 moles) in methylene chloride (50 ml) was added methanesulfonyl (1.55 ml, 20 mmoles) under ice-cooling with stirring and the mixture was stirred at room temperature for 1 hour. Then, 5-mercaptoimidazo[1,2-a]pyridine (1.50 g, 10 mmoles) and triethylamine (1.40 ml, 10 mmoles) were added, followed by stirring for 5 hours. The mixture was washed in turn with an aqueous saturated solid bicarbonate solution and saturated saline and dried over anhydrous magnesium sulfate. After the solvent was distilled off, the residue was purified by column chromatography (eluent: ethyl acetate) to obtain 0.88 g of the desired product (26.4%, light brown product).

NMR (200MHz, CDCl$_3$) δ: 2.91 (3H, s), 4.13 (2H, s), 6.52 (1H, m), 6.81 (1H, m), 6.92-7.28 (4H, m), 7.58 (1H, m), 7.66 (1H, m), 7.86 (1H, m).

EXAMPLE 45

Synthesis of 5-[3-(acetyloxy)propylthio]imidazo[1,2-a]pyridine (Compound 174)

To a solution of 5-[3-(hydroxy)propylthio]imidazo[1,2-a]pyridine (2.00 g, 9.60 mmoles) and triethylamine (1.60 ml, 11.5 mmoles) in methylene chloride (50 ml) was added acetic anhydride (1.10 ml, 11.6 mmoles) with stirring at room temperature and the mixture was further stirred at room temperature for 7.5 hours. The reaction mixture was washed with an aqueous 1N sodium hydroxide solution and dried. After the solvent was distilled off, the residue was purified by column chromatography [eluent: hexane/acetone (1:1)] to obtain 2.40 g of the desired product (100%, brown oily product).

NMR (200MHz, CDCl$_3$) δ: 1.98 (2H, quint, J=6.6Hz), 2.04 (3H, s), 3.06 (2H, t, J=7.0Hz), 4.19 (2H, t, J=6.2Hz), 6.94 (1H, d, J=6.8Hz), 7.17 (1H, dd, J=8.8, 6.8Hz), 7.62 (1H, d, J=8.8Hz), 7.71 (1H, s), 7.85 (1H, s).

IR (Neat) cm$^{-1}$: 1740, 1488, 1240.

EXAMPLE 46

Synthesis of 5-[3-(acetyloxy)propylthio]imidazo[1,2-a]pyridine (Compound 174)

To a solution of 3-bromo-1-propanol (0.50 g, 3.60 mmoles) and triethylamine (0.60 ml, 0.40 mmoles) in methylene chloride (15 ml) was added acetic anhydride (0.40 ml, 4.24 mmoles) with stirring at room temperature and the mixture was further stirred at room temperature overnight. The reaction mixture was washed with an aqueous 1N sodim hydroxide solution and dried. After the solvent was distilled off, ethanol (10 ml) and triethylamine (1.00 ml, 7.17 mmoles) was added to the residue. To the mixture was added 5-mercaptopyridine (0.49 g, 3.26 mmoles) with stirring at room temperature and the mixture was stirred at room temperature for 5 minutes. The solvent was distilled off and the residue was purified by column chromatography [eluent: hexane/acetone (1:1)] to obtain 0.54 g of the desired product (66.3%, brown oily product).

NMR (200MHz, CDCl$_3$) δ: 1.98 (2H, quint, J=6.6Hz), 2.04 (3H, s), 3.06 (2H, t, J=7.0Hz), 4.19 (2H, t, J=6.2Hz), 6.94 (1H, d, J=6.8Hz), 7.17 (1H, dd, J=8.8, 6.8Hz), 7.62 (1H, d, J=8.8Hz), 7.71 (1H, s), 7.85 (1H, s).

IR (Neat) cm$^{-1}$: 1740, 1488, 1240.

EXAMPLE 47

Synthesis of
5-[3-(benzoyloxy)propylthio]imidazo[1,2-a]pyridine
(Compound 175)

To a solution of 5-[3-(hydroxy)propylthio]imidazo[1,2-a]pyridine (1.00 g, 4.80 mmoles) and triethylamine (0.80 ml, 5.74 mmoles) in methylene chloride (25 ml) was added benzoyl chloride (1.10 ml, 11.6 mmoles) with stirring at room temperature and the mixture was further stirred at room temperature for 30 minutes. The reaction mixture was washed with an aqueous 1N sodium hydroxide solution and dried. After the solvent was distilled off, the residue was purified by column chromatography [eluent: hexane/acetone (1:1)] to obtain 1.32 g of the desired product (88.1%, white solid).

Melting point: 60°-61° C.

Elemental analysis for C$_{17}$H$_{16}$N$_2$O$_2$S, Calcd.: C, 65.36; H, 5.16; N, 8.97. Found: C, 65.52; H, 5.17; N, 8.84.

NMR (200MHz, CDCl$_3$) δ: 2.13 (2H, quint, J=6.6Hz), 3.16 (2H, t, J=7.2Hz), 4.46 (2H, t, J=6.2Hz), 6.96 (1H, d, J=7.0Hz), 7.15 (1H, dd, J=9.2, 7.0Hz), 7.38-7.64 (4H, m), 7.69 (1H, s), 7.86 (1H, s), 7.99 (2H, dd, J=7.2, 1.6Hz).

IR (Neat) cm$^{-1}$: 1713, 1487, 1280.

EXAMPLE 48

Synthesis of
5-[3-[2-(phenyl)ethylcarbonyloxy]propylthio]imidazo[1,2-a]pyridine (Compound 176)

To a solution of 5-[3-(hydroxy)propylthio]imidazo[1,2-a]pyridine (1.00 g, 4.80 mmoles) and triethylamine (0.80 ml, 5.74 mmoles) in methylene chloride (25 ml) was added 3-phenylpropionyl chloride (1.01 g, 5.99 mmoles) with stirring at room temperature and the mixture was further stirred at room temperature for 2 hours. The reaction mixture was washed with an aqueous 1N sodium hydroxide solution and dried. After the solvent was distilled off, the residue was purified by column chromatography [eluent: hexane/acetone (1:1)] to obtain 1.37 g of the desired product (84.2%, yellow oily product).

Elemental analysis for C$_{19}$H$_{20}$N$_2$O$_2$S, Calcd.: C, 67.03; H, 5.92; N, 8.23. Found: C, 66.86; H, 6.01; N, 7.81.

NMR (200MHz, CDCl$_3$) δ: 1.92 (2H, quint, J=6.6Hz), 2.63 (2H, t, J=7.7Hz), 2.94 (4H, t, J=7.2Hz), 4.19 (2H, t, J=6.2Hz), 6.91 (1H, d, J=7.2Hz), 7.10-7.35 (6H, m), 7.61 (1H, d, J=9.0Hz), 7.72 (1H, s), 7.84 (1H, s).

IR (Neat) cm$^{-1}$: 1730, 1487, 1288.

EXAMPLE 49

Synthesis of
5-[3-(acetyloxy)propylsulfinyl]imidazo[1,2-a]pyridine
(Compound 177) and
5-[3-(acetyloxy)propylsulfonyl]imidazo[1,2-a]pyridine
(Compound 178)

To a solution of 5-[3-(acetyloxy)propylthio]imidazo[1,2-a]pyridine (1.00 g, 3.99 mmoles) in chloroform (25 ml) was added m-chloroperbenzoic acid (1.47 g, 5.96 mmoles) with stirring under ice-cooling and the mixture was further stirred under ice-cooling for 1.5 hours. The reaction mixture was washed in turn with an aqueous 20% sodium bisulfite solution and an aqueous saturated sodium bicarbonate solution and dried. After the solvent was distilled off, the residue was purified by column chromatography [eluent: hexane/acetone (1:1)] to obtain 0.19 g of 5-[3-(acetyloxy)propylsulfinyl]imidazo[1,2-a]pyridine (Compound 177) (34.6%, yellow oily product) and 0.19 g of 5-[ 3-(acetyloxy)propylsulfonyl]imidazo[1,2-a]pyridine (Compound 178) (16.5%, yellow oily product).

5-[3-(acetyloxy)propylsulfinyl]imidazo[1,2-a]pyridine
(Compound 177)

NMR (200MHz, CDCl$_3$) δ: 1.90-2.30 (2H, m), 2.02 (3H, s), 3.05-3.30 (2H, m), 4.10-4.30 (2H, m), 7.31-7.38 (2H, m), 7.47-7.87 (2H, m), 7.92 (1H, s).

IR (Neat) cm$^{-1}$: 1740, 1240, 1063, 1033 5-[3-(acetyloxy)propylsulfonyl]imidazo[1,2-a]pyridine (Compound 178).

NMR (200MHz, CDCl$_3$) δ: 1.98 (3H, s), 2.03-2.20 (2H, m), 3.30-3.40 (2H, m), 4.13 (2H, t, J=6.2Hz), 7.36 (1H, dd, J=9.0, 7.2Hz), 7.68 (1H, dd J=7.2, 1.2Hz), 7.86 (1H, s), 7.96 (1H, d, J=9.0Hz), 8.28 (1H, s).

IR (Neat) cm$^{-1}$: 1740, 1325, 1240, 1130.

EXAMPLE 50

Synthesis of
5-[3-(methoxy)propylthio]imidazo[1,2-a]pyridine(Compound 179)

To a solution of 5-[3-(hydroxy)propylthio]imidazo[1,2-a]pyridine (803 mg, 3.86 mmoles) in tetrahydrofuran (30 ml) was added 60% sodium hydride in oil (0.19 g, 4.6 mmoles) with stirring under ice-cooling and the mixture was further stirred under ice-cooling for 30 minutes. To the reaction mixture was added methyl iodide (0.36 ml, 5.8 mmoles), followed by stirring at room temperature overnight. The reaction mixture was poured into water, which was extracted with methylene chloride (30 ml×3). The methylene chloride layers were combined and dried over anhydrous magnesium sulfate. After the solvent was distilled off, the residue was purified by column chromatography (eluent: ethyl acetate) to obtain 308 mg of the desired product (35.9%, light brown oily product).

NMR (200MHz, CDCl$_3$) δ: 1.92 (2H, tt, J=6.0, 7.2Hz), 3.10 (2H, t, J=7.3Hz), 3.32 (3H, s), 3.48 (2H, t, J=5.8Hz), 6.91 (1H, dd, J=1.2, 7.0Hz), 7.15 (1H, dd, J=7.2, 9.0Hz), 7.57 (1H, td, J=1.0, 9.0Hz), 7.70 (1H, d, J=1.2Hz), 7.84 (1H, t, J=0.8Hz).

EXAMPLE 51

Synthesis of
5-[3-(phenoxy)propylthio]imidazo[1,2-a]pyridine
(Compound 180)

(1) Synthesis of
5-[3-(methanesulfonyloxy)propylthio]imidazo[1,2-a]pyridine

To a solution of 5-[3-(hydroxy)propylthio]imidazo[1,2-a]pyridine (1.030 g, 4.95 mmoles) and triethylamine (1.03 ml, 7.4 mmoles) in methylene chloride (30 ml) was added methanesulfonyl chloride (0.46 ml, 5.9 mmoles) with stirring under ice-cooling and the mixture was further stirred under ice-cooling for 10 minutes. The reaction mixture was washed with water and the aqueous layer was extracted with methylene chloride (30 ml×3). The methylene chloride layers were combined and dried over anhydrous magnesium sulfate. Then, the solvent was distilled off to obtain crude 5-[3-(methanesulfonyloxy)propylthio]imidazo[1,2-a]pyridine as a yellow oily product.

(2) Synthesis of
5-[3-(phenoxy)propylthio]imidazo[1,2-a]pyridine
(Compound 180)

To a solution of phenol (0.70 g, 7.4 mmoles) in tetrahydrofuran (20 ml) was added 60% sodium hydride in oil (0.30 ml, 7.4 mmoles) with stirring under ice-cooling and the mixture was further stirred under ice-cooling for 30 minutes. To the reaction mixture was added a solution of crude 5-[3-(methanesulfonyloxy)propylthio]imidazo[1,2-a]pyridine obtained in the above (1) in tetrahydrofuran (10 ml), followed by heating under reflux overnight. The reaction mixture was poured into water, which was extracted with methylene chloride (30 ml×4). The methylene chloride layers were combined and dried over anhydrous megnesium sulfate. After the solvent was distilled off, the residue was purified by column chromatography (eluent: ethyl acetate) to obtain 1.220 g of the desired product (86.8%, light brown oily product).

NMR (200MHz, CDCl$_3$) δ: 2.13 (2H, tt, J=5.9, 7.1Hz), 3.22 (2H, t, J=7.2Hz), 4.09 (2H, t, J=5.8Hz), 6.85–7.00 (4H, m), 7.13 (1H, dd, J=7.0, 9.0Hz), 7.25–7.33 (2H, m), 7.57 (1H, td, J=0.8, 9.0Hz), 7.71 (1H, d, J=1.4Hz), 7.85 (1H, s).

EXAMPLE 52

Synthesis of 5-[3-[2-(phenoxy)ethyloxy] propylthio]imidazo[1,2-a]pyridine (Compound 181)

(1) Synthesis of
1-methanesulfonyloxy-2-(phenoxy)ethane

To a solution of 2-(phenoxy)ethanol (1.35 g, 9.78 mmoles) and triethylamine (2.04 ml, 14.7 mmoles) in methylene chloride (30 ml) was added methanesulfonyl chloride (0.91 ml, 12 mmoles) with stirring under ice-cooling and the mixture was further stirred under ice-cooling for 10 minutes. The reaction solution was washed with water and the aqueous layer was extracted with methylene chloride (30 ml×3). The methylene chloride layers were combined and dried over anhydrous magnesium sulfate. After the solvent was distilled off, the residue was subjected to column chromatography [eluent: hexane/methyl (1:1)] to obtain crude 1-methanesulfonyloxy-2-(phenoxy)ethane as a pale yellow oily product.

(2) Synthesis of
5-[3-[2-(phenoxy)ethyloxy]propylthio]imidazo[1,2-a]pyridine (Compound 181)

To a solution of 5-[3-(hydroxy)propylthio]imidazo[1,2-a]pyridine (1.018 g, 4.89 mmoles) in tetrahydrofuran (20 ml) was added 60% sodium hydride in oil (0.30 ml, 7.4 mmoles) with stirring under ice-cooling and the mixture was further stirred under ice-cooling for 30 minutes. To the reaction mixture was added a solution of crude 1 methanesulfonyloxy-2-(phenoxy)ethane obtained in the above (1) in tetrahydrofuran (10 ml), followed by heating under reflux for 4.5 hours. The reaction solution was poured into water, which was extracted with methylene chloride (30 ml×4). The methylene chloride layers were combined and dried over anhydrous megnesium sulfate. After the solvent was distilled off, the residue was purified by column chromatography (eluent: ethyl acetate) to obtain 0.870 g of the desired product (54.2%, light brown oily product).

NMR (200MHZ, CDCl$_3$) δ: 1.96 (2H, tt, J=6.1, 7.1Hz), 3.13 (2H, t, J=7.2Hz), 3.66 (2H, t, J=5.9Hz), 3.78 (2H, dd, J=3.3, 6.1Hz), 4.11 (2H, dd, J=3.9, 5.5Hz), 6.88–7.00 (4H, m), 7.13 (1H, dd, J=7.0, 9.0Hz), 7.24–7.32 (2H, m), 7.56 (1H, td, J=0.9, 9.0Hz), 7.69 (1H, d, J=1.2Hz), 7.83 (1H, t, J=0.8Hz).

EXAMPLE 53

Synthesis of
5-[3-[3-(phenyl)propyloxy]propylthio]imidazo[1,2-a]pyridine (Compound 182)

To a solution of 5-[3-(hydroxy)propylthio]imidazo[1,2-a]pyridine (1.070 g, 5.137 mmoles) in tetrahydrofuran (30 ml) was added 60% sodium hydride in oil (0.25 g, 6.2 mmoles) with stirring under ice-cooling and the mixture was stirred under ice-cooling for 30 minutes. To the reaction mixture was added methyl iodie (1.53 g, 7.71 mmoles), followed by stirring at room temperature overnight. The reaction mixture was poured into water, which was extracted with methylene chloride (30 ml×3). The methylene chloride layers were combined and dried over anhydrous magnesium sulfate. After the solvent was distilled off, the residue was purified by column chromatography (eluent: ethyl acetate) to obtain 0.987 g of the desired compound (58.9%, light brown oily product).

NMR (200MHz, CDCl$_3$) δ: 1.81–1.99 (4H, m), 2.68 (2H, t, J=7.6Hz), 3.12 (2H, t, J=7.2Hz), 3.41 (2H, t, J=6.4Hz), 3.51 (2H, t, J=5.8Hz), 6.91 (1H, dd, J=1.1, 7.1Hz), 7.10–7.32 (6H, m), 7.56 (1H, td, J=1.0, 9.0Hz), 7.69 (1H, d, J=1.4Hz), 7.84 (1H, t, J=1.0Hz).

EXAMPLE 54

Synthesis of
5-[3-[2-(anilino)ethyloxy]propylthio]imidazo[1,2-a]pyridine (Compound 183)

(1) Synthesis of
5-[3-(methanesulfonyloxy)propylthio]imidazo[1,2-a]pyridine

To a solution of 5-[3-(hydroxy)propylthio]imidazo[1,2-a]pyridine (2.003 g, 9.62 mmoles) and triethylamine (2.01 ml, 14.4 mmoles) in methylene chloride (30 ml) was added methanesulfonyl chloride (0.89 ml, 12 mmoles) with stirring under ice-cooling and the mixture was further stirred under ice-cooling for 10 minutes. The reaction mixture was washed with water and the aqueous layer was extracted with methylene chloride (30 ml×3). The methylene chloride layers were combined and dried over anhydrous magnesium sulfate. Then, the solvent was distilled off to obtain crude 5-[3-(methanesulfonyloxy)propylthio]imidazo[1,2-a]pyridine as a yellow oily product.

(2) Synthesis of 5-[3-[2-(anilino)ethyloxy]propylthio]imidazo[1,2-a]pyridine (Compound 183)

To a solution of 2-anilinoethanol (1.98 g, 14.4 mmoles) in tetrahydrofuran (20 ml) was added 60% sodium hydride in oil (1.15 ml, 28.9 mmoles) with stirring under ice-cooling and the mixture was further stirred under ice-cooling for 30 minutes. To the reaction mixture was added a solution of crude 5-[3-(methanesulfonyloxy)propylthio]imidazo[1,2-a]pyridine obtained in the above (1) in tetrahydrofuran (10 ml), followed by heating under reflux for 1 hour. The reaction mixture was poured into water which was extracted with methylene chloride (30 ml×4). The methylene chloride layers were combined and dried over anhydrous magnesium sulfate. After the solvent was distilled off, the residue was purified by column chromatography (eluent: ethyl acetate) to obtain 0.951 g of the desired product (30.2%, light green crystals).

NMR (200MHz, CDCl$_3$) δ: 1.94 (2H, tt, J=5.9, 7.1Hz), 3.10 (2H, t, J=7.2Hz), 3.28 (2H, t, J=5.2Hz), 3.57 (2H, t, J=6.0Hz), 3.62 (2H, t, J=5.1Hz), 3.98 (1H, br, s), 6.63 (2H, d, J=7.3Hz), 6.72 (1H, t, J=7.3Hz), 6.89 (1H, dd, J=1.0, 7.4Hz), 7.10-7.22 (3H, m), 7.57 (1H, d, J=9.0Hz), 7.70 (1H, d, J=1.4Hz), 7.83 (1H, s).

EXAMPLE 55

Synthesis of 5-[3-[2-(N-methanesulfonylanilino)ethyloxy]propylthio]imidazo[1,2-a]pyridine (Compound 184)

To a solution of 5-[3-[2-(phenylamino)ethyloxy]propylthio]imidazo[1,2-a]pyridine (1.034 g, 3.158 mmoles) and triethylamine (0.88 ml, 6.3 mmoles) in methylene chloride (30 ml) was added methanesulfonyl chloride (0.37 ml, 4.7 mmoles) with stirring under ice-cooling and the mixture was further stirred under ice-cooling for 10 minutes. The reaction mixture was washed with water and the aqueous layer was extracted with methylene chloride (30 ml×3). The methylene chloride layers were combined and dried over anhydrous magnesium sulfate. After the solvent was distilled off, the residue was purified by column chromatography (eluent: ethyl acetate) to obtain 16 mg of the desired product (brown oily product)

NMR (200MHz, CDCl$_3$) δ: 1.86 (2H, tt, J=5.9, 7.2H), 2.92 (3H, s), 3.03 (2H, t, J=7.2Hz), 3.50 (2H, t, J=5.3Hz), 3.50 (2H, t, J=5.8Hz), 3.84 (2H, t, J=5.7Hz), 6.89 (1H, dd, J=1.0, 7.0Hz), 7.15 (1H, dd, J=7.0, 9.0Hz), 7.31-7.40 (5H, m), 7.57 (1H, d, J=9.0Hz), 7.70 (1H, d, J=1.0Hz), 7.82 (1H, s).

EXAMPLE 56

Synthesis of 5-[1-(2-thienylcarbonyl)-4-piperidyloxy]imidazo[1,2-a]pyridine (Compound 185)

To a suspension of 60% sodium hydride in oil (0.40 g, 10 mmoles) in dimethylformamide (30 ml) was added 1-(2-thienylcarbonyl)-4-hydroxypiperidine (2.11 g, 10 mmoles) with stirring under ice-cooling and the mixture was stirred at room temperature for 30 minutes. To this reaction mixture was added 5-chloroimidazo[1,2-a]pyridine (1.53 g, 10 mmoles) with stirring under ice-cooling, followed by stirring at room temperature for 7 hours. Water was added to the reaction mixture, which was extracted with ethyl acetate and dried. After the solvent was distilled off, the residue was purified with column chromatography [eluent: ethyl acetate/hexane (1:1)→ethyl acetate/hexane (2:1)→ethyl acetate/ethanol (50:1)] to obtain 0.15 g of the desired product (4.6%, pale yellow oily product).

NMR (200MHz, CDCl$_3$) δ: 2.03-2.16 (4H, m), 3.85-3.96 (4H, m), 4.84-4.93 (1H, m), 6.09 (1H, d, J=7.0Hz), 7.06 (1H, dd, J=3.6, 5.0Hz), 7.12-7.35 (3H, m), 7.47 (1H, dd J=1.2, 5.0Hz), 7.62 (1H, d, J=1.2Hz), 7.67 (1H, d, J=0.8Hz).

EXAMPLE 57

Synthesis of 5-[2-(N-benzylmethylsulfonylamino)ethyloxy]imidazo[1,2-a]pyridine (Compound 186)

(1) Synthesis of 2-(N-benzylmethylsulfonylamino)1-ethanol

To a solution of N-benzylamino ethanol (7.10 ml, 50 mmoles) and triethylamine (7.67 ml, 55 mmoles) in dichloromethane (100 ml) was added methylsulfonyl chloride (4.26 ml, 55 mmoles) with stirring under ice-cooling and the mixture was stirred at room temperature for 30 minutes. The reaction mixture was washed in turn with an aqueous saturated sodium bicarbonate solution and water and dried. After the solvent was distilled off, the residue was purified by column chromatography [eluent: ethyl acetate/hexane (1:1)→ethyl acetate/hexane (2:1)→ethyl acetate] to obtain 1.99 g of the desired product (17.4%, pale yellow oily product).

NMR (200MHz, CDCl$_3$) δ: 1.89 (1H, bs), 2.94 (3H, s), 3.37 (2H, t, J=5.0Hz), 3.65 (2H, t, J=5.0Hz), 4.47 (2H, s), 7.35-7.39 (5H, m).

IR (Neat) cm$^{-1}$: 3520, 3030, 2930, 1600, 1595, 1455, 1320, 1140.

(2) Synthesis of 5-[2-(N-benzylmethylsulfonylamino)ethyloxy]imidazo[1,2-a]pyridine (Compound 186)

To a suspension of 60% sodium hydride in oil (0.20 g, 5 mmoles) in dimethylformamide (20 ml) was added 2-(N-benzylmethylsulfonylamino)-1-ethanol (1.14 g, 5 mmoles) with stirring under ice-cooling and the mixture was stirred at room temperature for 30 minutes. To this reaction mixture was added 5-chloroimidazo[1,2-a]pyridine (0.763 g, 5 mmoles) with stirring under ice-cooling, followed by stirring at 80° C. for 16 hours. After cooling, water was added to the reaction mixture, which was extracted with ethyl acetate and dried. After the solvent was distilled off, the residue was purified by column chromatography [eluent: ethyl acetate/hexane (1:1)→ethyl acetate/hexane (2:1)] to obtain 0.68 g of the desired product (39.4%, pale yellow oily product).

NMR (200MHz, CDCl$_3$) δ: 2.94 (3H, s), 3.72 (2H, t, J=6.0Hz), 4.23 (2H, t, J=5.8Hz), 4.52 (2H, s), 5.87 (1H, d, J=6.8Hz), 7.11 (1H, d, J=7.2, 9.0Hz), 7.25-7.40 (6H, m), 7.58 (2H, s).

IR (Neat) cm$^{-1}$: 3150, 3030, 2930, 1640, 1540.

EXAMPLE 58

Synthesis of 5-[3-(methylsulfonylamino)propylthio]imidazo[1,2-a]pyridine (Compound 27)

(1) Synthesis of 3-methylsulfonylamino-1-methylsulfonyloxypropane

To a solution of 3-amino-1-propanol (11.47 ml, 150 mmoles) and triethylamine (46 ml, 330 mmoles) in dichloromethane (250 ml) was added methylsulfonyl chloride (25.5 ml, 330 mmoles) with stirring under ice-cooling and the mixture was stirred at room temperature for 30 minutes. The reaction mixture was washed in turn with an aqueous sodium bicarbnonate and water and dried. After the solvent was distilled off, the residue was purified by column chromatography (eluent: ethyl acetate) to obtain 24.22 g of the desired product (69.8%, white crystals).

Melting point: 53.5°–55.5° C.

NMR (200MHz, CDCl$_3$) δ: 2.02 (2H, quint, J=6.4Hz), 2.98 (3H, s), 3.05 (3H, s), 3.31 (2H, q, J=6.4Hz), 4.37 (2H, t, J=5.8Hz), 4.68 (1H, bs).

(2) Synthesis of 5-[3-(methylsulfonylamino)propylthio]imidazo[1,2-a]pyridine (Compound 27)

To a solution of 5-mercaptoimidazo[1,2-a]pyridine (1.50 g, 10 mmoles) and 4M sodium methylate (2.93 ml, 12 mmoles) in ethanol (50 ml) was added 3-methylsulfonylamino-1-methylsulfonyloxypropane (2.77 g, 12 mmoles) at room temperature and the mixture was heated under reflux for 16 hours. After cooling, the solvent was distilled off. The residue was dissolved in chloroform, washed with an aqueous saturated sodium bicarbonate solution and dried. After the solvent was distilled off, the residue was purified by column chromatography [eluent: ethyl acetate/ethanol (50:1)] to obtain 1.34 g of the desired product (47.5%, pale yellow crystals).

Melting point: 114°–116° C.

NMR (200MHz, CDCl$_3$) δ: 1.92 (2H, quint, J=6.8Hz), 2.95 (3H, s), 3.09 (2H, t, J=7.0Hz), 3.30 (2H, q, J=6.6Hz), 4.82 (1H, bs), 6.94 (1H, d, J=7.0Hz), 7.15 (1H, dd, J=7.0, 9.0Hz), 7.60 (1H, d, J=9.0Hz), 7.69 (1H, s), 7.84 (1H, s).

IR (KBr) cm$^{-1}$: 3440, 3080, 2850, 1615, 1485, 1315, 1140.

EXAMPLE 59

Synthesis of 5-[1-(methyhlsulfonyl)-4-piperidylsulfinyl]imidazo[1,2-a]pyridine (Compound 187) and 5-[1-(methylsulfonyl)-4-piperidylsulfonyl]imidazo[1,2-a]pyridine (Compound 188)

To a solution of 5-[1-(methylsulfonyl)-4-piperidylthio]imidazo[1,2-a]pyridine (0.934 ml, 3.0 mmoles) in chloroform (30 ml) was added m-chloroperbenzoic acid (0.914 g, 4.5 mmoles) with stirring under ice-cooling and the mixture was stirred at room temperature for 2 hours. To this reaction mixture was added m-chloroperbenzoic acid (0.609 g, 3.0 mmoles) with stirring under ice-cooling and the mixture was stirred at room temperature for 1 hour. The reaction mixture was washed with an aqueous 1N sodium hydroxide solution and dried. After the solvent was distilled off, the residue was purified by column chromatography [eluent: ethyl acetate/ethanol (25:1→10:1)] to obtain 0.272 g of the sulfone compound (24.2%, white crystals) as Fraction 1 and 0.273 g of the sulfoxide compound (26.5%, white crystals) as Fraction 2.

5-[1-(methylsulfonyl)-4-piperidylsulfonyl]imidazo[1,2-a]pyridine (Compound 188)

Melting point: 224°–226° C.

NMR (200MHz, CDCl$_3$) δ: 1.96–2.12 (4H, m), 2.68–2.82 (1H, m), 2.79 (3H, s), 3.22 (1H, m), 3.85–3.97 (2H, m), 7.36 (1H, dd, J=7.2, 8.8Hz), 7.64 (1H, d, J=7.2Hz), 7.86 (1H, bs), 7.98 (1H, d, J=9.0Hz), 8.34 (1H, bs).

5-[1-(methylsulfonyl)-4-piperidylsulfinyl]imidazo[1,2-a]pyridine (Compound 189)

Melting point: 205° C. (decomp.).

NMR (200MHz, CDCl$_3$) δ: 1.69–2.08 (4H, m), 2.66–2.85 (1H, m), 2.79 (3H, s), 3.29 (1H, m), 3.82–3.79 (2H, m), 7.25–7.38 (2H, m), 7.81–7.86 (2H, m), 8.09 (1H, bs).

EXAMPLE 60

Synthesis of 5-[2-[3-(hydroxy)isoindolin-1-one-2-yl]ethylthio]imidazo[1,2-a]pyridine (Compound 189)

To a suspension of 5-mercaptoimidazo[1,2-a]pyridine (159 mg, 1 mmole) and 2-[2-(bromo)ethyl]-3-hydroxyindolin-1-one (256 mg, 1 moole) in ethanol (15 ml) was added trimethylamine (0.21 ml, 1.5 mmoles) and the mixture was stirred at room temperature for 12 hours and heated under reflux for 2 hours. After the solvent was distilled off, chloroform was added to the residue, which was washed with water and dried over anhydrous magnesium sulfate. After the solvent was distilled off, the residue was purified by column chromatography [eluent: ethyl acetate/ethanol (10:1)] to obtain 11.9 g of the desired product (36.6%, pale yellow solid).

NMR (200MHz, CDCl$_3$-DMSO-d$_6$) δ: 3.38 (2H, m), 3.88 (2H, m), 5.82 (1H, m), 6.47 (1H, m), 7.14–7.67 (2H, m), 7.44–7.67 (5H, m), 7.76 (1H, m), 7.85 (1H, m).

EXAMPLE 61

Synthesis of 5-[2-(isoindolin-1-one-2-yl)ethylthio]imidazo[1,2-a]pyridine (Compound 190)

To a suspension of 5-mercaptoimidazo[1,2-a]pyridine (150 mg, 1 mmole) and 2-[2-(bromo)ethyl]isoindolin-1-one (240 mg, 1 mmole) in ethanol (15 ml) was added triethylamine (0.21 ml, 1.5 mmoles) and the mixture Was stirred at room temperature for 12 hours and heated at reflux for 2 hours. After the solvent was distilled off, chloroform was added to the residue which was washed with water and dried over anhydrous magnesium sulfate. After the solvent was distilled off, the residue was purified by column chromatography [eluent: ethyl acetate/ethanol (15:1)] to obtain 238 mg of the desired product (77.0%, light brown solid).

NMR (200MHz, CDCl$_3$) δ: 3.32 (2H, t, J=6.8Hz), 3.89 (2H, t, J=6.8Hz), 4.39 (2H, s), 7.05–7.18 (2H, m), 7.37–7.60 (4H, m), 7.70 (1H, d, J=1.2Hz), 7.82–7.88 (2H, m).

EXAMPLE 62

Synthesis of
5-[2-(phenylsulfonylamino)ethylsulfinyl]imidazo[1,2-a]pyridine (Compound 191)

To a suspension of 5-[2-(phenylsulfonylamino)ethyhlthio]imidazo[1,2-a]pyridine (600 mg, 1.8 mmoles) in chloroform (50 ml) was added m-chloroperbenzoic acid (913 mg, 4.5 mmoles) with stirring under ice-cooling and the mixture was stirred at room temperature for 22 hours. The reaction mixture was washed in turn with an aqueous 1N sodium hydroxide solution and saturated saline and dried over anhydrous magnesium sulfate. After the solvent was distilled off, the residue was purified by column chromatography [eluent: ethyl acetate-/ethnol (10:1)] to obtain 200 mg of the desired product (31.8%, light brown solid).

NMR (200MHz, CDCl$_3$) δ: 3.16 (1H, m), 3.35–3.65 (3H, m), 5.96 (1H, br), 7.28–7.36 (2H, m), 7.48–7.67 (3H, m), 7.75–7.90 (5H, m).

EXAMPLE 63

Synthesis of
5-[2-(tert-bothoxycarbonylamino)ethylthio]-3-nitroimidazo[1,2-a]pyridine (Compound 192)

To a solution of cysteamine (2.95 g, 38.2 mmoles) in DMF (50 ml) was added 60% sodium hydride in oil (1.53 g, 38.2 mmoles) with stirring under ice-cooling and the mixture was stirred at room temperature for 10 minutes. To the mixture was added 5-chloro-3-nitroimidazo[1,2-a]pyridine (5.81 g, 29.4 mmoles), followed by stirring under ice-cooling for 30 minutes and further stirring at room temperature for 30 minuters. Di-tert-butyl dicarbonate (9.62 g, 44 mmmles) was added, followed by stirring at room temperature for 4 hours. The reaction mixture was poured into water, which was extracted with ethhyl acetate, washed with water and dried over anhydrous magensium sulfate. After the solvent was distilled off, the residue was purified by column chromatography (eluent: ethyl acetate) to obtain 2.06 g of the desired product (20.7%, tan solid).

NMR (200MHz, CDCl$_3$) δ: 1.41 (9H, s), 3.17–3.41 (4H, m), 5.00 (1H, br), 7.36 (1H, dd, J=6.2, 2.6Hz), 7.59–7.71 (2H, m), 8.54 (1H, s).

EXAMPLE 64

Synthesis of
5-[2-(methylsulfonylamino)ethylthio]-3-nitroimidazo[1,2-a]pyridine (Compound 193)

(1) Synthesis of
5-[2-(amino)ethylthio]-3-nitroimidazo[1,2-a]pyridine.-dihydrochloride To a suspension of 5-[2-(tert-butoxycarbonylamino)ethylthio]-3-nitroimidazo[1,2-a]pyridine (364 mg, 1.08 mmoles) in methanol (3 ml) was added conc. hydrochloric acid (2 ml) and the mixture was stirred at room temperature for 1 hour. Then, the solvent was distilled off to obtain 340 mg of the desired product (quantitative, brown solid).

(2) Synthesis of
5-[2-(methylsulfonylamino)ethylthio]-3-nitroimidazo[1,2-a]pyridine (Compound 193)

To a solution of 5-[2-(amino)ethylthio]-3-nitroimidazo[1,2-a]pyridine.dihydrochloride (221 mg, 0.71 mmole) and triethylamine (0.33 ml, 2.37 mmoles) in methylene chloride (30 ml) was added methanelsulfonyl chloride (0.08 ml, 1.03 mmoles) with stirring under ice-cooling and the mixture was further stirred at the same temperature for 10 minutes. After washing with water, the reaction mixture was dried over anhydrous magnesium sulfate. After the solvent was distilled off, the residue was purified by column chromatography (eluent: ethyl acetate) to obtain 108 mg of the desired product (48.0%, orange solid).

NMR (200MHz, CDCl$_3$) δ: 2.84 (3H, s}, 3.09 (3H, s), 3.33 (2H, m), 7.24 (1H, br), 7.65 (1H, m), 7.77–7.90 (2H, m), 8.78 (1H, s).

EXAMPLE 65

Synthesis of
5-[1-(methylsulfonyl)-4-piperidyloxy]-3-nitroimidazo[1,2-a]pyridine (Compound 194)

To a solution of 4-hydroxy-1-methylsulfonylpiperidine (2.15 g, 12 mmoles) in dimethylformamide (3 ml) was added 60% sodium hydride in oil (0.48 g, 12 mmoles) with stirring under ice-cooling and the mixture was stirred at room temperature for 10 minutes. To the reaction mixture was added 5-chloro-3-nitroimidazo[1,2-a]pyridine (1.976 g, 10 mmoles) with stirring under ice-cooling and the mixture was stirred at the same temperature for 30 minutes. The reaction mixture was poured into water, which was extracted with ethyl acetate. The precipitate was filtered off, washed with water and dried to obtain 1.862 g of the desired product (54.7%, yellow solid). The organic layer was washed with water and dried over anhydrous magnesium sulfate. After the solventy was distilled off, the crude crystlals thus obtained were recrystallized from methylene-n-hexane to obtain 460 mg of the desired product (460 mg, tan solid).

NMR (200MHz, CDCl$_3$) δ: 2.02–2.23 (3H, s), 2.90 (3H, s), 3.29 (2H, m), 3.66 (2H, m}, 4.95 (1H, m}, 6.44 (1H, d, J=7.6Hz), 7.43 (1H, d, J=8.8Hz), 7.58 (1H, dd, J=8.8, 7.6Hz), 8.40 (1H, s).

EXAMPLE 66

Synthesis of
3-amino-5-[1-(methylsulfonyl)-4-piperidyloxy]imidazo[1,2-a]pyridine (Compound 195)

To a solution of 5-[1-(methylsulfonyl)-4-piperidyloxy]-3-nitroimidazo[1,2-a]pyridine (70 mg, 0.226 mmole) in methylene chloride (10 ml) was added 10% palladium-carbon (50 ml) and the mixture was stirred in hydrogen atmosphere at room temperature for 1.5 hours. After the reaction mixture was treated with Cellite, the solvent was distilled off. To the residue was added chloroform, which was washed in turn with an aqueous saturated sodium bicarbonate solution and water and dried over anhydrous magnesium sulfate. After the solvent was distilled off, the residue was purified by column chromatography [eluent: chloroform/methanol (15:1)] to obtain 93 mg of the desired product (30.0%, brown oily product).

NMR (200MHz, CDCl$_3$) δ: 2.17 (4H, m), 2.84 (3H, s), 3.28–3.53 (4H, m), 4.70 (1H, m), 5.87 (1H, dd, J=7.2Hz), 6.87 (1H, dd, J=9, 7.2Hz), 7.07 (1H, d, J=9Hz), 7.27 (1H, s).

EXAMPLE 67

Synthesis of 2-isobutylcarbamoyl-5-[2-(methylsulfonylamino)ethylthio][1,2-a]pyridine (Compound 196)

A mixture of 2-ethoxycarbonyl-5-[2-(methylsulfonylamino)ethylthio][1,2-a]pyridine (148 mg, 0.431 mmole), isobutylamine (0.86 ml, 8.65 mmoles) and ethanol (10 ml) was heated under reflux for 18 hours. To the mixture was further added isobutylamine (1.72 ml, 17.3 mmoles) and the mixture was heated under reflux for 17 hours. To the mixture was further added isobutylamine (1.72 ml., 17.3 mmoles) and the mixture was heated under reflux for 8 hours. After the solvent was distilled off, the residue was purified by column chromatography (eluent: ethyl acetate) to obtain 139 mg of the desired product (86.9%, pale yellow solid).

NMR (200MHz, CDCl$_3$) δ: 1.00 (6H, d, J=6.6Hz), 1.93 (1H, nonet, J=6.6Hz), 2.98 (3H, s), 3.15–3.43 (6H, m), 5.51 (1H, brt, J=6Hz), 7.10 (1H, dd, J=7, 1.2Hz), 7.24 (1H, dd, J=9, 7Hz), 7.49 (1H, br), 7.55 (1H, m), 8.47 (1H, s).

EXAMPLE 68

According to the same manner as that described in Example 31, the following compound was obtained.

5-[3-[N-(methylsulfonyl)-3-(phenyl)propylamino]-propylthio]imidazo[1,2-a]pyridine (Compound 197)

NMR (200MHz, CDCl$_3$) δ: 1.80–2.00 (4H,), 2.62 (2H, t, J=7.6Hz), 2.80 (3H, s), 3.02 (2H, t, J=7Hz), 3.17 (2H, m), 3.28 (2H, m), 6.91 (1H, dd, J=7, 1Hz), 7.07–7.34 (6H, m), 7.59 (1H, d, J=9Hz), 7.85 (1H,m).

EXAMPLE 69

Synthesis of 5-[1-(methylsulfonyl)-4-piperidylthio]imidazo[1,2-a]pyridine (free compound of Compound 29)

(1) Synthesis of 1-methylsulfonyl-4-methylsulfonyloxypiperidine

To a solution of 4-hydroxypiperidine (5.10 g, 50 mmoles) and triethylamine (20.9 ml, 150 mmoles) in methylene chloride (150 ml) was added methanesulfonyl chloride (8.54 ml, 110 mmoles) with stirring under ice-cooling and the mixture was stirred at room temperature for 1 hour. The reaction mixture was washed in turn with an aqueous saturated sodium bicarbonate solution and saturated saline and dried over anhydrous magnesium sulfate. After the solvent was distilled off, the residue was solidified with ethyl acetate-n-hexane to obtain 11.45 g of the desired product (88.3%, pale yellow solid).

NMR (200MHz, CDCl$_3$) δ: 2.07 (4H, s), 2.81 (3H, s), 3.36 (4H, m), 4.93 (1H, m).

(2) Synthesis of 5-[1-(methylsulfonyl)-4-piperidylthio]imidazo[1,2-a]pyridine (free compound of Compound 29)

To a suspension of 5-mercaptoimidazo[1,2-a]pyridine (1.50 g, 10 mmoles) in ethanol (100 ml) was added a solution of 4.1M sodium methylate (2.44 ml, 10 mmoles) in methanol and the mixture was stirred at room temperature for 10 minutes. To the reaction mixture was added 1-methylsulfonyl-4-methylsulfonyloxypiperidine (2.83 g, 11 mmoles) at room temperature and the mixture was heated under reflux for 14 hours. After the solvent was distilled off, the residue was dissolved in chloroform, which was washed in turn with an aqueous 1N sodium hydroxide solution and water and dried over anhydrous magnesium sulfate. After the solvent was distilled off, the residue was purified by column chromatography [eluent: ethyl acetate/ethanol (10:1)] to obtain 1.27 g of the desired product (40.8%, light brown solid).

NMR (200MHz, CDCl$_3$) δ: 1.70–2.13 (4H, m), 2.79 (3H, s), 2.90 (2H, m), 3.35 (1H, m), 3.69 (2H, m), 7.05 (1H, dd, J=7, 1.2Hz), 7.17 (1H, dd, J=8.8, 7Hz), 7.67 (1H, d, J=8.8Hz), 7.71 (1H, d, J=1.2Hz), 7.96 (1H, s).

| Preparation 1 | |
|---|---|
| (1) Compound 1 | 100 g |
| (2) Lactose | 50 g |
| (3) Corn starch | 15 g |
| (4) Carboxymethylcellulose calcium | 44 g |
| (5) Magnesium stearate | 1 g |
| 1,000 Tablets | 210 g |

All the components (1), (2) and (3) and 30 g of the component (4) were kneaded with water, dried under vacuum and granulated. The granulated powder was mixed with 14 g of the component (4) and 1 g of the component (5) and the mixture was charged in a tabletting machine to obtain 1,000 tablets containing 100 mg of the component (1) per one tablet.

| Preparation 2 | |
|---|---|
| (1) Compound 1 | 10 g |
| (2) Lactose | 4.5 g |
| (3) Corn starch | 4.5 g |
| (4) Magnesium stearate | 1 g |
| 100 Capsules | 20 g |

All the components were thoroughly admixed and filled into a suitable gellatin capsule to obtain 100 capsules containing 100 mg of the component (1) per one capsule.

| Preparation 3 | |
|---|---|
| (1) Compound 2 | 10 g |
| (2) Sodium chloride | 1.8 g |
| (3) Distilled water for injection | suitable amount |
| Total amount | 200 ml |

The component (3) was added to all the components (1) and (2) to dissolve them and the total amount of the solution was adjusted to 200 ml. Then, the solution was sterilized and filled into ampoules of suitable size to obtain 100 ampoules containing 100 mg of the component (1) per one ampoule.

Experiment 1

Calmodulin inhibitory activity (Experimental method)

To a reaction system (0.45 ml) composed of 50 mM Tris-HCl buffer (pH 7.4), 5 mM MgCl$_2$, 10 μM CaCl$_2$ and calmodulin [2 units; manufactured by Sigma Co., p-0270] or 3 mM EGTA, cyclic nucleotide phosphodiesterase [0.01 unit; manufactured by Sigma Co., p-0520], and 1 μM cGMP ([$^3$H]cGMP, containing 3nCi) was added the compound of the present invention obtained in the above Example (0.1% DMSO solution, 50 μl )

and the reaction was carried out at 37° C. for 15 minutes. Then, the reaction was terminated by boiling the tubes for 2 minutes. The [$^3$H]5'-GMP products was converted to [$^3$H]guanosine by additional incubation at 37° C. for 10 minutes with 50 μg of snake venom (C. atrox), as 5'-nucleotidase. Following the addition of carrier guanosine, into the reaction tubes Dowex 1×8 resin was added, and the tubes were centrifuged for 1 minute. Radioactivity in the 250 μl of supernatant was counted. The determination of the inhibition was according to the following formula.

% Inhibition=100−(count in the presence of a medicine−count in the presence of EGTA)/(count in the absence of a medicine−count in the presence of EGTA)×100

The results are shown in Table 1.

TABLE 1

| Compound No. | (Calmodulin inhibitory activity) Inhibitory activity (%, $10^{-5}$M) |
|---|---|
| 1 | 94 |
| 5 | 50 |
| 9 | 100 |
| 14 | 85 |
| 16 | 66 |
| 26 | 100 |
| 27 | 51 |
| 28 | 72 |
| 30 | 64 |
| 32 | 62 |
| 34 | 53 |
| 37 | 58 |
| 42 | 100 |
| 44 | 65 |
| 48 | 50 |
| 50 | 65 |
| 51 | 83 |
| 56 | 62 |
| 62 | 79 |
| 69 | 57 |
| 64 | 82 |
| 67 | 72 |
| 69 | 57 |
| 74 | 50 |
| 75 | 55 |
| 77 | 80 |
| 78 | 56 |
| 79 | 50 |
| 83 | 76 |
| 84 | 69 |
| 87 | 51 |
| 89 | 54 |
| 101 | 56 |
| 102 | 52 |
| 103 | 52 |
| 105 | 67 |
| 109 | 50 |
| 115 | 53 |
| 118 | 74 |
| 127 | 57 |
| 128 | 50 |
| 130 | 50 |
| 132 | 50 |
| 135 | 60 |
| 136 | 52 |
| 144 | 60 |
| 145 | 63 |
| 158 | 81 |
| 165 | 65 |
| 168 | 56 |
| 169 | 58 |

As shown in Table 1, the compounds of the present invention have excellent calmodulin inhibitory activity.

Experiment 2

Hypotensive activity in spontaneous hypertensive rat (SHR)

(Experimental method)

SHR male rats of twenty weeks old were used. They were warmed in an incubator at 37° C. for 5 minutes and the measurement was conducted according to Plethysmograph method. Medicines (the compounds in the above Examples) were suspended in gum arabic-water and were orally administered in an amount of 2.5 ml/kg. Blood pressure was measured before administration of medicines, at 1 hour and at 5 hours after administration, and the change of the value from that before administration was determined, respectively.

The results are shown in Table 2.

TABLE 2

| | Hypotensive activity | | |
|---|---|---|---|
| Compound No. | Dose (mg/kg) | Change of blood pressure (mmHg) 1 hour | 5 hours |
| 1 | 100 | −11.2 | −11.5 |
| 28 | 100 | −13.5 | −43.0 |
| 64 | 100 | −31.0 | −27.0 |
| 67 | 100 | −15.0 | −22.0 |
| 69 | 100 | −7.0 | −32.0 |

As shown in Table 2, the compounds of the present invention have excellent hypotensive activity.

Experiment 3

Effect on incidence of arrhythmia caused by ischemia and following reperfusion in rat heart (Experimental method)

Male Sprague Dawley rats (Japan Clea) of 9 to 10 weeks old were anesthetized with 50 mg/kg (i.p.) of sodium pentobarbital. The heart was exposed by a left thoractomy under artificial ventilation with room air and silk suture was placed under the main left coronary artery (LAD) to ligate for 5 minutes. Then, the ligature was released again for reperfusion. The incidence of ventricular tachycardia (VT), ventricular fibrillation (VF) and cardiac arrest (CA) caused until 10 minutes after reperfusion were noted. Medicines (compounds obtained in the above Examples) were orally administered (5 ml/kg) at 1 hour before tightening the ligature. The effect of medicines were estimated in comparison with the frequency of a group received a vehicle according to $X^2$-test.

The results are shown in Table 3 below.

TABLE 3

| | Effect on incidence of arrhythmia caused by ischemia and following reperfusion in rat heart | | | |
|---|---|---|---|---|
| Compound No. | Dose (mg/kg) | VT (Frequency) | VF | CA |
| 1 | 10 | 2/4 | 2/4 | 1/4 |
| 1 | 30 | 1/4 | 1/4 | 0/4 |
| 14 | 10 | 1/3 | 0/3 | 0/3 |
| 26 | 10 | 2/3 | 1/3 | 1/3 |
| 32 | 30 | 1/3 | 1/3 | 1/3 |
| 64 | 30 | 1/3 | 1/3 | 1/3 |
| 118 | 30 | 1/3 | 1/3 | 0/3 |
| 127 | 30 | 1/3 | 1/3 | 0/3 |
| vehicle | — | 7/7 | 7/7 | 2/7 |

As shown in Table 3, the compounds of the present invention decrease the frequency of arrhythmia induced by 5 minutes of occlusion followed by reperfusion.

Experiment 4

Effect on acute renal failure caused by ischemia and following reperfusion in rat kidneys.

(Experimental method)

SD rats (male) of 6 to 7 weeks old were anesthetized with pentobarbital sodium (50 mg/kg, i.p.) and bilateral renal arteries were ligated. After 45 minutes, a clip was removed to reperfuse. After 20 hours, blood was collected from abdominal aorta under anesthesia with pentobarbital sodium and blood urea nitrogen (BUN) was measured. Medicines (compounds obtained in the above Examples) were orally administered (5 ml/kg) 1 hour before occulusion of renal artery.

The results are shown in Table 4.

TABLE 4

Effect on acute renal failure caused by ischemic renal/reperfusion in rat

| Compound No. | Dose (mg/kg) | Blood urea nitrogen (mg/dl) |
| --- | --- | --- |
| 1 | 10 | 83.3 ± 20.4 |
| 1 | 30 | 71.1 ± 11.4 |
| 1 | 50 | 65.6 ± 5.1 |
| vehicle | — | 118.2 ± 5.0 |

As shown in Table 4, the compounds of the present invention depress the increase in BUN in ischemic renal/reperfusion of rats.

Another aspect of the present invention to provide novel angiogenesis inhibitors.

It is well known that angiogenesis occurs in normal physiologic conditions of human or mammal such as embryogenesis and ovulation or placentation caused by female sexual cycle, wound healing, restoration process of inflammation, and in various morbidity wherein blood capillaries rapidly form and increase to cause serious damage to tissue and the like shown as follows. As the diseases caused by such a pathologic increase of blood capillaries, for example, there have been known diabetic retinopathy, retrolental fibroplasia, angiogenesis accompanying keratoplasty, glaucoma, opthalmic tumor and trachoma and the like in the opthalmologic field; psoriasis, suppurative granuloma and the like in the dermatologic field; angioma, fibrous angioma and the like in the pediatric field; hypergenic cicatrix, granulation and the like in the surgical field; arthritis rhuematica, edematous sclerosis and the like in the medical field; atherosclerosis and the like in cardiac diseases; various tumors and the like.

Particularly, a lot of people become blindness by abnormal increase of angiogenesis in diabetic retinopathy and trachoma. Further, a lot of people suffer from breakage of cartilage by abnormal angiogenesis in a joint due to arthritis rhuematica. Accordingly, it is requested to develop a compound useful as a medicine for treatment or prevention of diseases accompanying such an abnormal increase of angiogenesis. Furthermore, it is considered that rapid growth and extension of a tumor is caused by vascularization induced by an angiogensis factor which is produced by tumor cells. Therefore, it is expected that an angiogenesis inhibitor becomes a new medicine for treatment of various tumors and studies on angiogenesis inhibitors have been started [J. Folkman, Advance in Cancer Research, 43, 175 (1985), edited by George Klein and Sidney Weinhouse].

It has already been known that angiogenesis is inhibited by using heparin or heparin fragment in combination with a so-called "angiostatic steriod" (angiogenesis inhibiting steroid) such as cortison and the like [J. Folkman et al., Science, 221, 719 (1983); J. Folkman et al., Annals of Surgery, 206, 374 (1981)].

Further, it has been recognized that angiogenesis inhibitory activity is synergistically exhibited by using sulfated $\alpha$, $\beta$, and $\gamma$-cyclodextrin, particularly, $\beta$-cyclodetrin tetradecasulfate or heparin in combination with an angiostatic steroid as described above, fumagillin, a collagen synthesis inhibitor or the like [D. Ingber and J. Folkman, Laboratory Investigation, 59, 44 (1988)].

On the other hand, U.S. Pat. No. 4,599,331 discloses that angiogenesis inhibitory activity is observed by using a steroid (etianic acid derivative) alone. However, this steroid has also strong adrenocorticosteroid hormone activity and, therefore, there is a large dufficulty to use it as a medicine.

There has been a lot of reports concerning imidazo[1,2-a]pyridine derivatives. However, there are few reports of a pharmacological activity concerning a compound wherein an alkylthio group having a functional group is bound at 5-position thereof. Particularly, regarding such a compound having a carbamate ester as the functional group, only 5-(2-tert-butoxycarbonylaminoethylthio)imidazo[1,2-a]pyridine and 5-[2-(N-chloroacetylcarbamoyloxy)ethylthio]imidazo[1,2-a]pyridine are reported as a starting material of synthesis of cephem compounds having excellent antibacterial activity in European Patent Application P87108189.9. However, there is no description about a pharmacological activity thereof.

Under these circumstances, the present inventors have synthesized various imidazo[1,2-a]pyridine derivatives having a substituent at 5-position and intensively studied their pharmacological activities. As a result, it has been found that some of them have excellent angiogenesis inhibitory activities.

Thus, the present invention also provides a novel angiogensis inhibitory composition comprising a compound of the formula (1):

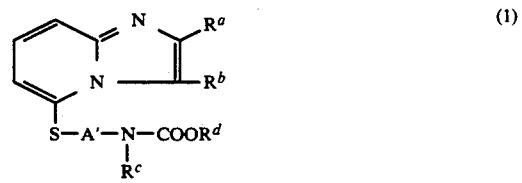

wherein A' is a divalent $C_{1-15}$ hydrocarbon group which may contain ethereal oxygen at any possible position and a branched part of the hydrocarbon group may be substituted; $R^a$ and $R^b$ are the same or different and are a hydrogen, an optionally substituted hydrocarbon group, a halogen, a nitro group, a nitroso group, an optionally protected amino group, a lower alkoxycarbonyl group or a lower alkyl carbamoyl group; $R^c$ is a hydrogen or an optionally substituted hydrocarbon group or may form a ring together with the carbon atom of A; and $R^d$ is an optionally substituted hydrocarbon group, or a salt thereof.

In the formula (1), examples of the group represented by A' include the formula:

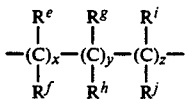

wherein x, y and z are integers of 0 to 5, respectively; $R^e$, $R^f$, $R^g$, $R^h$, $R^i$ and $R^j$ are a hydrogen, or an optionally substituted lower alkyl, lower alkenyl, aralkyl, aryl, or heterocyclic group; or $R^e$ and $R^f$ or $R^g$ and $R^h$ or $R^i$ and $R^j$ may bind together to form a ring, or $R^e$ or $R^g$ may bind together with $R^i$ or $R^j$ to form a ring, —$CH_2CH_2OCH_2CH_2$— or the formula:

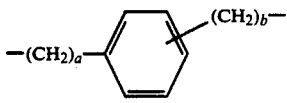

wherein a and b are integers of 0 to 5, respectively and the like.

Examples of the lower alkyl group represented by $R^e$, $R^f$, $R^g$, $R^h$, $R^i$ and $R^j$ include a straight or branched alkyl group having 1 to 6 carbon atoms such as methyl, ethyl, propyl, isopropyl, butyl, isobutyl, sec-butyl, tert-butyl, pentyl, hexyl and the like. Examples of the lower alkenyl group represented by $R^e$, $R^f$, $R^g$, $R^h$, $R^i$ and $R^j$ include a lower alkenyl group having 2 to 6 carbon atoms such as vinyl, allyl, 2-butenyl, 3-butenyl and the like. The lower alkyl and lower alkenyl group may have 1 to 5 substituents and examples thereof include halogen, nitro, amino, lower alkylamino, cyclic amino, lower alkoxy, aryloxy, carbamoyl, cyano, hydroxy, carboxy, lower alkoxycarbonyl, lower alkylcarbamoyl and the like. Examples of halogen include fluoro, bromo, chloro and iodo.

Examples of the lower alkylamino group as the above substituent include a N-monoalkylamino group of which alkyl moiety has 1 to 6 carbon atoms such as methylamino, ethylamino, propylamino, butylamino and the like, and a N,N-dialkylamino group of which alkyl moiety has 1 to 6 carbon atoms such as dimethylamino, diethylamino, dibutylamino, methylethylamino and the like.

Examples of the cyclic amino group as the above substituent include a 4 to 7 membered cyclic amino group such as N-pyrrolidino, piperazino, piperadinyl, morpholino, homopiperazino and the like.

Examples of the lower alkoxy group as the above sustituent include a straight or branched alkoxy group having 1 to 6 carbon atoms such as methoxy, ethoxy, propoxy, isopropoxy, butoxy, pentoxy and the like. Examples of the aryloxy group as the above substituent include a $C_{6-10}$ aryloxy group such as phenoxy, 1-naphthoxy, 2-naphthoxy and the like. Examples of the lower alkoxycarbonyl group as the above substituent include an alkoxycarbonyl group of which alkoxy moiety has 1 to 6 carbon atoms such as methoxycarbonyl, ethoxycarbonyl propoxycarbonyl, butoxycarbonyl and the like. Examples of the lower alkylcarbamoyl group as the above substituent include a N-monoalkylcarbamoyl group of which alkyl moiety has 1 to 6 carbon atoms such as methylcarbamoyl, ethylcarbamoyl, propylcarbamoyl, butylcarbamoyl and the like and a N,N-dialkylcarbamoyl group of which alkyl moiety has 1 to 6 carbon atoms such as dimethylcarbamoyl, diethylcarbamoyl, dibutylcarbamoyl, methylethylcarbamoyl and the like.

As the aralkyl group represented by $R^e$, $R^f$, $R^g$, $R^h$, $R^i$ and $R^j$, for example, there is a phenyl lower alkyl group of which alkyl moiety has 1 to 6 carbon atoms such as benzyl, phenethyl, 3-phenylpropyl, 4-phenylbutyl and the like and a naphthyl-lower alkyl of which alkyl moiety has 1 to 6 carbon atoms such as (1-naphthyl)methyl, 2-(1-naphthyl)ethyl, 2-(2-naphthyl)ethyl and the like. The phenyl moiety of the phenyl-lower alkyl group and the naphthyl part of the naphthyl-lower alkyl group may substituted with 1 to 4 substituents such as halogen, lower alkyl, lower alkoxy, nitro, cyano, hydroxy, lower alkoxycarbonyl, carbamoyl, lower alkylcarbamoyl and the like. Examples of halogen include fluoro, bromo, chloro and iodo. Examples of the lower alkyl group and the lower alkenyl group include those similar to the lower alkyl group or a lower alkenyl group represented by $R^e$, $R^f$, $R^g$, $R^h$, $R^i$ and $R^j$. As the lower alkoxy group, for example, there is a straight or branched alkoxy group having 1 to 6 carbon atoms such as methoxy, ethoxy, propoxy, isopropoxy, butoxy, pentoxy and the like. As the lower alkoxycarbonyl group, for example, there are an alkoxycarbonyl group of which alkoxy moiety has 1 to 6 carbon atoms such as methoxycarbonyl, ethoxycarbonyl, propoxycarbonyl, butoxycarbonyl and the like. As the lower alkylcarbamoyl group, for example, there are a N-alkylcarbamoyl group of which alkyl moiety has 1 to 6 carbon atoms such as methylcarbamoyl, ethylcarbamoyl, propylcarbamoyl, butylcarbamoyl and the like, and a N,N-dialkylcarbamoyl group of which alkyl moiety has 1 to 6 carbon atoms such as dimethylcarbamoyl, diethylcarbamoyl, dibutylcarbamoyl, methylethylcarbamoyl and the like.

As the aryl group represented by $R^e$, $R^f$, $R^g$, $R^h$, $R^i$ and $R^j$, for example, there are an aromatic monocyclic, bicyclic or tricyclic hydrocarbon group such as phenyl, 1-naphthyl, 2-naphthyl, phenanthryl, anthryl and the like, and examples of the heterocyclic group include an aromatic monocyclic group or bicyclic hetero ring bound via carbon atoms, which contains 1 to 4 hetero atoms such as sulfur, oxygen, nitorgen and the like, such as thienyl, furyl, benzothienyl, benzofranyl and the like. The aryl group and the heterocyclic group may be substituted with 1 to 4, preferably 1 or 2 substituents such as halogen, lower alkyl, lower alkoxy, nitro, cyano, oxo, hydroxy, amino, lower alkoxycarbonyl, carbamoyl, lower alkylcarbamoyl and the like. Examples of halogen in the above substituents include fluoro, bromo, chloro and iodo. As the lower alkyl group, for example, there is the alkyl group having 1 to 6 carbon atoms as described above and, as the lower alkenyl group, for example, there is a lower alkenyl group having 2 to 6 carbon atoms as described above. As the alkoxy group, for example, there is an alkoxy group having 1 to 6 carbon atoms and, as the lower alkoxycarbonyl group, for example, there is an alkoxycarbonyl group of which alkoxy moiety has 1 to 6 carbon atoms. As the lower alkylcarbamoyl group, for example, there is a N-monoalkylcarbamoyl group of which alkyl moiety has 1 to 6 carbon atoms and a N,N-dialkylcarbamoyl group of which alkyl moiety has 1 to 6 carbon atoms. Examples of these groups include groups similar to the lower alkoxy group, the lower alkoxycarbonyl group and the lower alkylcarbamoyl group as the substituents of the phenyl moiety in the above aralkyl group. As the aryl group having oxo group, for example, there is benzoquinolyl, naphthoquinolyl, anthraquinolyl and the like.

As the ring formed by binding $R^e$ and $R^f$, $R^g$ and $R^h$, or $R^i$ and $R^j$, for example, there is $C_{3-8}$ cycloalkane such as cyclopropane, cyclobutane, cyclohexane and the like. As the ring formed by binding $R^e$ or $R^g$ with $R^h$ or $R^i$, for example, there is $C_{3-8}$ cycloalkane such as cyclopropane, cyclobutane, cyclopentane, cyclohexane, cycloheptane and the like.

As the optionally substituted hydrocarbon group in $R^a$ and $R^b$, for example, there are a lower alkyl group, a lower alkenyl group, an aralkyl group and an aryl group which are optionally substituted with the substituents in the above group represented by A'. Further, examples of halogen include fluoro, chloro, bromo and iodo. As the optionally protected amino group, for example, there are an amino group, an acylamino group and the like. As the acyl group of the above acylamino group, there is a group represented by —$COR^d$ or —$CO_2R^d$, for example, a lower alkylcarbonyl group (e.g. $C_{1-6}$alkylcarbonyl group such as acetyl, etc.), aralkylcarbonyl group (e.g. $C_{7-10}$aralkylcarbonyl group such as benzylcarbonyl, etc.), arylcarbonyl group (i.e. $C_{6-10}$aryl-carbonyl group such as benzoyl, etc.), a lower alkyloxycarbonyl group (e.g. $C_{1-4}$ alkyloxycarbonyl group such as methoxycarbonyl, etc.), aralkyloxycarbonyl group (e.g. $C_{7-10}$ aralkyloxycarbonyl group such as benzyloxycarbonyl, etc.), aryloxycarbonyl group (e.g. $C_{6-10}$ aryloxycarbonyl group such as phenoxycarbonyl, etc.) and the like.

As the lower alkoxycarbonyl group and the lower alkylcarbamoyl group in $R^a$ and $R^b$, for example, there is a group similar to a lower alkoxycarbonyl group and a lower alkylcarbamoyl group as the substituent of the phenyl moiety in the arakyl group represented by $R^e$, $R^f$, $R^g$, $R^h$, $R^i$ and $R^j$.

As the optionally substituted hydrocarbon group of $R^c$ and $R^d$, for example, there are an optionally substituted lower alkyl group, a lower alkenyl group, a cycloalkyl group, an aralkyl group, an aryl group and the like. As the optionally substituted lower alkyl group, the lower alkenyl group, aralkyl group and aryl group, for example, there is a group similar to those described with respect to the group represented by A'. As the cycloalkyl group, for example, there is a cycloalkyl group having 3 to 8 carbon atoms such as cyclopropyl, cyclobutyl, cyclopentyl, cyclohexyl, cycloheptyl, cyclooctyl and the like. As the substituent of the cycloalkyl group, for example, there are those similar to the substituent of the optionally substituted lower alkyl group as described in A' and the number thereof is 1 to 5. Examples of the group wherein $R^c$ is connedted with $R^e$, $R^f$, $R^g$, $R^h$, $R^i$ or $R^j$ in A' to form a ring include a group represented by the formula:

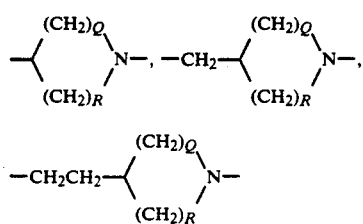

wherein Q and R are 2 or 3, repectively.

The compound of the formula (1) can form, for example, an acid addition salt with an inorganic acid such as hydrochloric acid, hydrobromic acid, sulfuric acid, phophoric acid or the like and an organic acid such as acetic acid, oxalic acid, methanesulfonic acid, maleic acid, fumaric acid, citric acid, tartaric acid, lactic acid or the like.

The compound (1) or a salt thereof may be a solvate and examples of a solvent of the solvate include alcohols such as methanol, ethanol, propanol, isopropanol and the like; ketones such as acetone and the like; ethers such as tetrahydrofuran, dioxane and the like.

As the preferred embodiment of the compound of the above formula (1) or a salt thereof, for example, there is a compound represented by the formula:

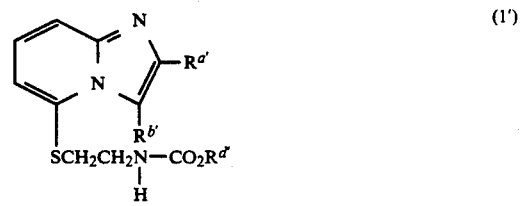

wherein $R^{a'}$ is a hydrogen or a lower alkyl group; $R^{b'}$ is a hydrogen or an optionally substituted lower alkyl group; and $R^{d'}$ is an optionally substituted lower alkyl group, a cycloalkyl group or a lower alkenyl group, or a salt thereof.

In the formula (1'), examples of the lower alkyl group represented by $R^{a'}$, the optionally substituted lower alkyl group represented by $R^{b'}$, and lower alkyl group and lower alkenyl group represented $R^{d'}$ include those described with respect to the groups represented by $R^e$, $R^f$, $R^g$, $R^h$, $R^i$ and $R^j$. Examples of the optionally substituted lower alkyl group represented by $R^{d'}$ include those described in the above $R^d$. $R^{d'}$ is preferably $C_{1-6}$ alkyl or $C_{1-6}$ alkenyl.

The compound (1) may contain an assymetric carbon in the molecule. When stereoisomers of R-and S- configurations are present, not only these isomers, but also a mixture thereof are included in the scope of the present invention.

Imidazo[1,2-a]pyridine derivatives (1) of the present invention or a salt thereof can be synthesized, for example, according to the following method.

(A) A compound of the formula:

wherein X' is a halogen such as chloro, bromo, iodo or the like and $R^a$ and $R^b$ are as defined above is reacted with a compound of the formula:

wherein A', $R^c$ and $R^d$ are as defined above, or a salt thereof.

(B) A compound of the formula:

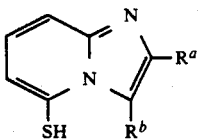
(4)

wherein $R^a$ and $R^b$ are as defined above or a salt thereof is reacted with a compound of the formula:

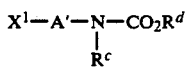
(5)

wherein A', $R^c$ and $R^d$ are as defined above, $X^1$ is a leaving group such as halogen (e.g. chloro, bromo, iodo, etc.), an arylsulfonyloxy group such as toluenesulfonyloxy group or an alkylsulfonyloxy group such as methanesulfonyloxy group, or a salt thereof.

(C) A compound of the formula:

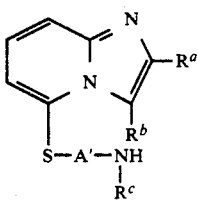
(6)

wherein A', $R^a$, $R^b$ and $R^c$ are as defined above, or a salt thereof is reacted with a compound of the formula:

(7)

wherein $R^d$ and X' are as defined above.

(D) A compound of the formula:

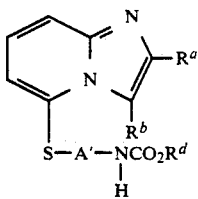
(8)

wherein A', $R^a$, $R^b$ and $R^d$ are as defined above, or a salt thereof is reacted with a compound of the formula:

(9)

wherein $X^1$ is as defined above and $R^{c'}$ is an optionally substituted hydrocarbon group.

(E) A compound of the formula:

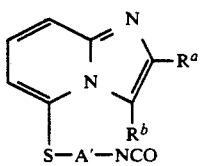
(10)

wherein A', $R^a$ and $R^b$ are as defined above is reacted with a compound of the formula:

(11)

wherein $R^d$ is as defined above.

(F) A compound of the formula:

(12)

wherein $X^2$ is a leaving group such as halogen (e.g. chloro, etc.), phenoxy group, imidazolyl and the like and A', $R^a$, $R^b$ and $R^c$ are as defined above, or a salt thereof is reacted with a compound of the formula:

(11)

wherein $R^d$ is as defined above.

(G) A compound of the formula:

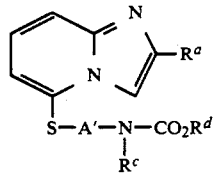
(1a)

wherein A', $R^a$, $R^c$ and $R^d$ are as defined above, or a salt thereof is reacted with a halogenating agent to obtain a compound of the formula:

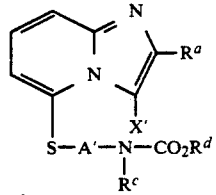
(1b)

wherein A', $R^a$, $R^c$ and $R^d$ are as defined above and X' is halogen, or a salt thereof.

(H) A compound of the formula (1a) or a salt thereof is nitrosated to obtain a compound of the formula:

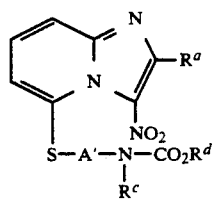
(1c)

wherein A', $R^a$, $R^c$ and $R^d$ are as defined above, or a salt.

(I) A compound of the formula (1a) is nitrosated to obtain a compound of the formula:

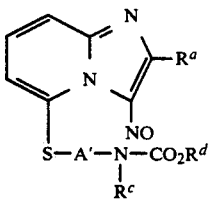

(1d)

wherein A', $R^a$, $R^c$ and $R^d$ are as defined above, or a salt thereof.

(J) A compound of the formula (1c) or (1d), or a salt thereof is reduced to obtain a compound of the formula:

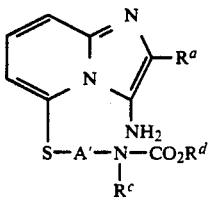

(1e)

wherein A', $R^a$, $R^c$ and $R^d$ are as defined above, or a salt thereof, or the compound (1e) or a salt thereof is further reacted with a compound (7) or a compound X'COR$^d$ (wherein X' and $R^d$ are as defined above) to obtain a compound of the formula:

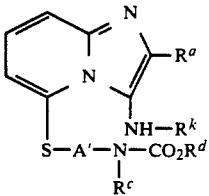

(1f)

wherein $R^k$ is —CO$_2$R$^d$ or —COR$^d$ and A, $R^a$, $R^c$ and $R^d$ are as defined above, or a salt thereof.

(K) According to the following scheme, the compound (1g) or a salt thereof is obtained.

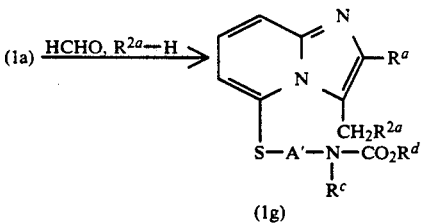

wherein $R^{2a}$ is a lower dialkylamino group or a cyclic amino group and A', $R^a$, $R^c$ and $R^d$ are as defined above.

The reaction of the compound (2) or a salt thereof with the compound (3) in the process A can be conducted at −10° C. to +200° C. in a solvent in the presence of a basic compound such as sodium hydroxide, potassium hydroxide, sodium hydride, potassium carbonate and the like by using 1 equivalent to excess amount (but not interfereing with the reaction) of the compound (3) per 1 equivalent of the compound (2) or a salt thereof. Examples of the solvent to be used include water; lower alcohols such as methanol, ethanol, propanol and the like; ketones such as acetone, methyl ethyl ketone and the like; ethers such as tetrahydrofuran and the like; aprotic polar solvents such as N,N-dimethylformamide, dimethylsulfoxide and the like. The reaction time is normally 1 hour to 2 days, preferably 1 to 8 hours.

The reaction of the compound (4) or a salt thereof with the compound (5) in the process B is conducted under conditions similar to those of the reaction of the compound (2) with the compound (3) in the process A.

The reaction of the compound (6) or a salt thereof with the compound (7) in the process C is conducted in a solvent at −30° C. to +200° C. in the presence of an inorganic base such as portassium carbonate, sodium bicarbonate or the like or an organic base such as triethylamine, pyridine, dimethylanilin, 1,4-azabicyclo[2.2.2]octane (DABCO) or the like by using 1 equivalent to extremely excess amount of the compound (7) based on the compound (6) or a salt thereof. Examples of the solvent to be used include water; lower alcohols such as methanol, ethanol, propanol and the like; ketones such as acetone, methyl ethyl ketone and the like; ethers such as tetrahydrofuran and the like; aprotic polar solvents such as N,N-dimethylformamide, dimethylsulfoxide and the like. The reaction time is normally 10 minutes to 24 hours, preferably 30 minutes to 6 hours.

The reaction of the compound (8) or a salt thereof with the compound (9) in the process D can be conducted in a solvent at −30° to +20° C. in the presence of a base such as potassium hydride, sodium hydride, sodium amide and the like by using 1 equivalent to extremely excess amount of the compound (9) based on the compound (8) or a salt thereof. Examples of the solvent to be used include ethers such as diethyl ether, tetrahydrofuran, dimethoxyethane and the like; aprotic polar solvents such as N,N-dimethylformamide, dimethylsulfoxide and the like. The reaction time is normally 30 minutes to 24 hours, preferably 30 minutes to 6 hours.

The reaction of the compound (10) with the compound (11) in the process E can be conducted at −10° to +150° C. in the absence or presence of a solvent by using 1 equivalent to extremely excess amount of the compound (11) based on the compound (10). Examples of the solvent to be used include ethers such as diethyl ether, tetrahydrofuran, dimethoxyethane and the like; halogenated hydrocarbons such as methylene chloride, chloroform, dichloroethane and the like; aprotic polar solvents such as N,N-dimethylformamide, dimethylsulfoxide and the like. In order to promote the reaction, a tertiary amine such as triethylamine, pyridine, dimethylaminopyridine, N-methylpiperidine or the like, or boron trifluoride ether (BF$_3$.Et$_2$O) can be added. The reaction time is normally 30 minutes to 24 hours, preferably 30 minuts to 6 hours.

The reaction of the compound (12) or a salt thereof with the compound (11) in the process F can be conducted at −30° C. to +200° C. in the absence or presence of a solvent by using 1 equivalent to extremely excess amount of the compound (11) based on the compound (12) or a salt thereof. Examples of the solvent to be used include ethers such as diethyl ether, tetrahydrofuran, dimethoxyethane and the like; halogenated hydrocarbons such as methylene chloride, chloroform, dichloroethane and the like; aprotic polar solvents such as N,N-dimethylformamide, dimethylsulfoxide and the like. In order to promote the reaction, a tertiary amines such as triethylamine, pyridine, dimethylaminopyridine, N-methylpiperidine or the like may be added. The reaction time is normally 30 minutes to 24 hours, preferably 30 minutes to 6 hours.

The reaction of the compound (1a) or a salt thereof with the halogenating agent in the process G can be conducted at −20° to +150° C. in the absence or presence of a solvent by using 1 equivalent to extremely excess amount of the harogenating agent based on the compound (1a) or a salt thereof. Examples of the solvent to be used include halogenated hydrocarbons such as methylene chloride, chloroform, dichloroethane, carbon tetrachloride and the like, acetic acid, propionic acid and the like. Examples of the hydrogenating agent include halogen molecules such as chlorine, bromine and the like; and N-halogenated succinimides such as N-chlorosuccinimide, N-bromosuccinimide, N-iodosuccinimide and the like. Further, upon reaction, a radical reaction initiator such as benzoyl peroxide or the like may be added. The reaction time is normally 30 minutes to 12 hours, preferably 1 to 12 hours.

The nitration of the compound (1a) or a salt thereof in the process H can be conducted at −20 to +100° C. in the absence or presence of a solvent by using 1 equivalent to extremely excess amount of a nitrating agent based on the compound (1a) or a salt thereof. Examples of the solvent to be used include acetic acid, acetic anhydride, sulfuric acid and the like. As the nitrating agent, for example, there is fuming nitric acid, conc. nitric acid, mixed acid (nitric acid with sulfuric acid, phosphoric acid or acetic anhydride) and the like. The reaction time is normally 30 minutes to 1 day, preferably 30 minutes to 6 hours.

The nitrosation of the compound (1a) or a salt thereof in the process I can be conducted at −20° to +100° C. in the absence or presence of a solvent by using 1 equivalent to extremely excess amount of a nitrosating agent based on the compound (1a) or a salt thereof. Examples of the solvent to be used include water; lower fatty acids such as acetic acid, propionic acid and the like; ethers such as tetrahydrofuran, dioxane and the like; aprotic polar solvents such as N,N-dimethylformamide, dimethylsulfoxide and the like. As the nitrosating agent, for example, there are potassium nitrite, sodium nitrite and the like. The above reaction is conducted in the presence of an acid such as hydrochloric acid, sulfuric acid, phophoric acid, acetic acid or the like. The reaction time is normally 30 minutes to 1 day, preferably 30 minutes to 6 hours.

The reduction of the compound (1c) or (1d) or a salt thereof in the process J can be conducted at −20° to +200° C. in the presence of a solvent by using 1 equivalent to extremely excess amount of a reducing agent based on the compound (1c) or (1d). Examples of the solvent to be used include water, methanol, ethanol, propanol, acetic acid and the like. As the reducing agent, for example, there is a mixture of iron and hydrochloric acid, zinc and acetic acid and the like. Further, the reaction can also be conducted at −20° to +200° C. in the presence of a solvent under atmospheric pressure of hydrogen by using a hydrogenation catalyst such as palladium black, palladium on carbon, raney-nickel or the like. The reaction time is normally 30 minutes to 2 days, preferably 1 to 12 hours.

Further, the reaction of the compound (1e) or a salt thereof with the compound (7), or the reaction of the compound (1e) or a salt thereof with X'COR⁴ is conducted under conditions similar to those of the reaction of the compound (6) or a salt thereof with the compound (7) in the process C.

The Mannich reaction of the compound (1a) or a salt thereof with a lower dialkylamine and formalin, or cyclic amine and formalin in the process K can be conducted at −20° to +10° C. in the presence of a solvent by using 1 equivalent to extremely excess amount of a Mannich reagent based on the compound (1a) or a salt thereof. Examples of the solvent to be used include water; lower alcohols such as methanol, ethanol, propanol, isopropanol and the like; lower fatty acids such as acetic acid, propionic acid and the like. The reaction time is normally 30 minutes to 1 day, preferably 1 to 12 hours.

In the above processes A to K, the compound which forms a salt may be used in the form of a salt and examples of such a salt include those described in the salt of the compound (1).

In the starting material used in the processes A to K, for example, the compound (2) can be obtained by the following process.

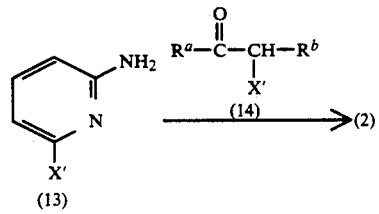

The reaction of the compound (13) with the compound (14) can be conducted at 0° to +200° C. in the absence or presence of a solvent by using 1 equivalent to extremely excess amount of the compound (14) based on the compound (13). Examples of the solvent to be used include water; lower alcohols such as methanol, ethanol, propanol and the like; ethers such as tetrahydrofuran, dimethoxyethane, dioxane and the like; nitriles such as acetonitrile, propionitrile and the like; aprotic polar solvents such as N,N-dimethylformamide, dimethylsulfoxide and the like. Further, on the above reaction, an inorganic base such as potassium carbonate, sodium bicarbonate or the like, or an organic base such as triethylamine, pyridine, dimethylanilin or the like may be added as an acid-trapping agent. The reaction time is normally 10 minutes to 7 days, preferably 1 hour to 2 days.

The compound (4) can be obtained, for example, by the following processes.

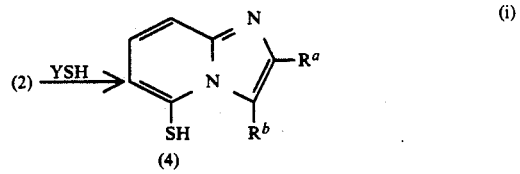

wherein Y is sodium or potassium and R$^a$ and R$^b$ are as defined above.

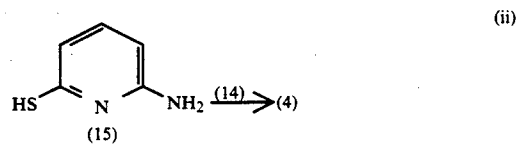

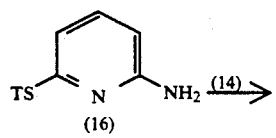 (iii)

(16)

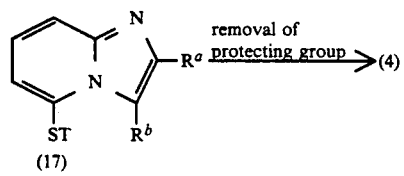

(17)

wherein T is a protecting group such as p-methoxybenzyl, benzyl or the like and $R^a$ and $R^b$ are as defined above.

The reaction of the compound (2) with YSH is conducted under conditions similar to those of the reaction of the compound (2) with the compound (3).

The reaction of the compound (15) with the compound (14) is conducted under conditions similar to those of the above reaction of the compound (13) with the compound (14).

The reaction of the compound (16) with the the compound (14) is conducted under conditions similar to those of the reaction of the compound (13) with the compound (14).

The compound (6) can be obtained, for example, by the following processes.

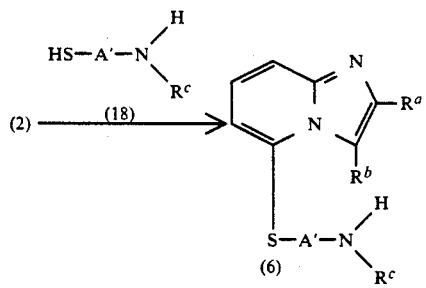

wherein A', $R^a$, $R^b$, $R^c$ and $R^d$ are as defined above.

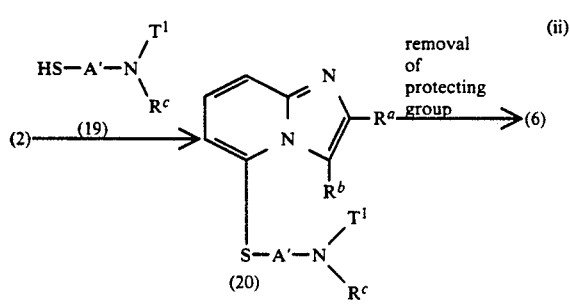

wherein $T^1$ is an amino protecting group such as benzyloxycarbonyl, tert-butoxycarbonyl, trifluoroacetyl, trityl, benzyl or the like; and A', $R^a$, $R^b$ and $R^c$ are as defined above.

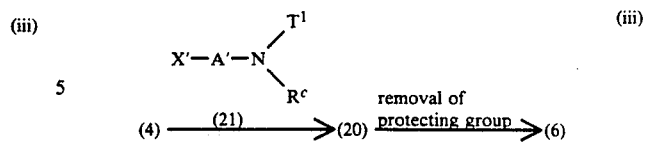

wherein A', $T^1$ and $R^c$ are as defined above, but further including that —$NT^1R^c$ is phthalimide.

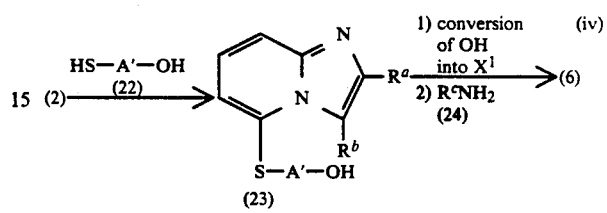

wherein A', $R^a$, $R^b$, $R^c$, $R^d$ and $X^1$ are as defined above.

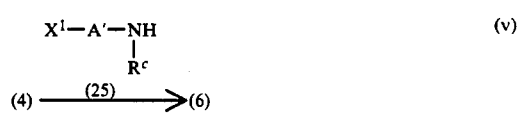

wherein $X^1$ and $R^c$ are as defined above.

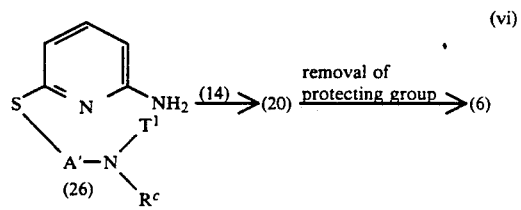

wherein A', $R^c$ and $T^1$ are as defined above, but further including that —$NT^1R^c$ is phthalimide.

The reaction of the compound (2) with the compound (18), the reaction of the compound (2) with the compound (19), the reaction of the compound (4) with the compound (21), the reaction of the compound (2) with the compound (22) and the reaction of the compound (4) with the compound (25) are conducted under conditions similar to those of the reaction of the compound (2) with the compound (3) in the above process A.

When $X^1$ is halogen, the conversion of the hydroxyl group of the compound (22) into $X^1$ is conducted by treating the compound (23) with phosphorous halide such as phosphorous trichloride, phosphorous oxychloride, phosphorous pentachloride, phosphorous tribromide and the like; a halogenating agent such as red phosphorous and halogen, thionyl chloride and the like. When $X^1$ is toluenesulfonyloxy group or methanesulfonyloxy group, it can be obtained by treating the compound (23) with toluenesulfonyl chloride or methanesulfonyl chloride. The subsequent reaction with the compound (24) is conducted at 0° to 200° C. in the absence or presence of a suitable solvent. All of these reactions are known and they can be conducted according to known conditions.

The reaction of the compound (26) with the compound (14) is conducted under conditions similar to those of the above reaction of the compound (13) with the compound (14).

The compound (10) is obtained, for example, by the following processes.

(i) The compound (27) is reacted with phosgene and the reaction mixture is heated to conduct dehydrochlorination.

(ii) The compound (28) is reacted with silver cyanate.

All of these reactions are also known and they can be conducted according to known conditions.

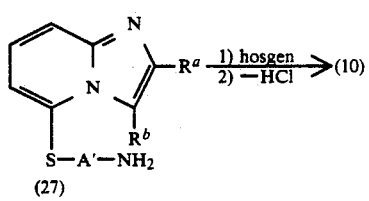
(27)

wherein A', $R^a$ and $R^b$ are as defined above.

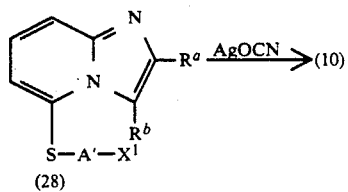
(28)

wherein A', $R^a$ and $R^b$ are as defined above.

The compound (12) can be obtained, for example, by the following processes.

(i) When $X^2$ is Cl, the compound (6) is reacted with phosgene.

(ii) When $X^2$ is phenoxy, the compound (6) is reacted with phenyl chlorocarbonate.

(iii) When $X^2$ is imidazolyl, the compound (6) is reacted with carbonyldiimidazole.

All of these reactions are known and they can be conducted according to known conditions.

All of the reactions for removing the above protecting group are known and they can be conducted according to known conditions. For example, p-methoxybenzyl group as a protecting group of a mercapto group can be removed by treating with mercuric acetate in trifluoroacetic acid and treating with hydrogen sulfide or 2-mercaptoethanol. Benzyl group can be removed by sodium metal in liquid ammonia.

For example, benzyloxycarbonyl group and benzyl group as protecting groups of amino group can be removed by conducting catalytic reduction (reaction temperature: 0° to 100° C.) in a solvent (e.g., alcohols, acetic acid, water, tetrahydrofuran, a mixed solvent thereof, etc.) in the presence of a catalyst (e.g., palladium on carbon, platinum oxide, etc.).

In the case of trityl group and tert-butoxycarbonyl group, they can be removed at 0° to 150° C. in a solvent (e.g., water, alcohols, tetrahydrofuran, dioxane, etc.) in the presence of an acid (e.g., mineral acids such as hydrochloric acid, phophoric acid, sulfuric acid, etc.; organic acids such as toluenesulfonic acid, methanesulfonic acid, acetic acid, etc.). Trifluoroacetyl group can be readily removed by treating with an alkali (e.g., sodium hydroxide, sodium bicarbonate solution, etc.)

Phthalimide group can be removed by treating with hydrazine hydrate in a solvent (e.g. methanol, ethanol, etc.).

The compounds (2), (4), (6), (10) and (12) can be isolated by the following conventional separation methods, but they may also be used in the form of a reaction mixture as a starting material for producing the desired compound (1) or a salt thereof. Further, among the above compounds, the compounds (3), (5), (7), (13), (14), (18), (19), (21), (22), (24) and (25) can be produced, for example, according to the processes described in Shinzikken Kagaku Koza, Vol.14, "Synthesis and Reaction of Organic compouds I-V", Japan Chemical Society, published by Maruzen K.K., Tokyo; Shinzikken Kagaku Koza, Vol.15, "Oxidation and Reduction I-V", Japan Chemical Society, published by Maruzen K.K., Tokyo; "Organic Syntheses", John Wiley and Sons, Inc., New York; "Theilheimer's Synthetic Methods of Organic Chemistry", Basel, New York, Karger and the like or modification thereof.

The isolation and purification of the compound (1) or a salt thereof from a reaction mixture is conducted according to conventional separation means (e.g. extraction, concentration, filtration, recrystallization, column chromatography, thin layer chromatography, etc.).

The compounds (1) or a salt thereof of the present invention have angiogenesis inhibitory activity and are useful as angiogenesis inhibitors, for example, antineoplastic agents, antiinflammatory agents, antirheumatoid arthritis agents, anti-diabetic retinopathy agents and the like.

The compound (1) or a salt thereof has low toxicity, and therefore, it can be orally or parenterally administered to mammal (e.g., human, rabbit, dog, cat, rat, mouse, guinea pig, etc.) as it is as a powder or a pharameceutical composition in a suitable dosage form. The dosage varies depending upon a particular administration route, conditions to be treated, age, weight of the patient or the like. When the compound (1) or a salt thereof is used as an antineoplastic agent, such an agent can be obtained by admixing the compound (1) or a salt thereof with a phramaceutically acceptable carrier. The compound (1) or a salt thereof can also be used by formulating it into a suitable dosage form such as instillations, injections, capsules, tablets, suppositories, solutions, emulsions, suspensions and other suitable dosage forms.

When a dosage form for parenterally administration, for example, injection is produced, isotonicities (e.g., glucose, D-sorbitol, D-mannitol, sodium chloride, etc.), preservatives (e.g., benzyl alcohol, chlorobutanol, methyl parahydroxybenzoate, propyl parahydroxybenzoate, etc.), anticoagulants (e.g., dextran sulfuric acid, heparin, etc.) and buffer agents (e.g., phophoric acid buffer, sodium acetate buffer, etc.) may be used. Further, a dosage form for oral administration can be used as capsules wherein the compound (1) or a salt thereof is admixed with lactose and the like, or used as sugar-coated tablets produced by a conventional method.

For example, in the case of administering the compound (1) or a salt thereof parenterally by injection to the diseased part (s.c., i.v. or i.m.), the dosage may be about 0.05 to 50 mg/kg/day, preferably about 0.2 to 20 mg/kg/day, more preferably about 0.5 to 10 mg/kg/day. In the case of oral administration, the dosage may be about 0.1 to 500 mg/kg/day, preferably about 1 to 100 mg/kg/day, more preferably 5 to 50 mg/kg/day. Further, the compound (1) or a salt thereof can be used for topical application. For example, by washing a diseased part of the body such as head, breast, abdomen, limb and the like with a solution wherein the compound (1) or a salt thereof is dissolved in an isotonic solution in a concentration of about 0.01 to 2 w/v %, or by applying an ointment containing the compound (1) or a salt thereof in an amount of about 0.1 to 50 mg/1 g to the above diseased part, the compound (1) of a salt thereof can be used for preventing and treating tumor of these parts.

As described hereinabove, an agiogenesis inhibitory composition comprising the compound (1) and a salt thereof of the present invention have excellent activity and, in view of this activity, they are useful as medicines for prevention and treatment of tumor, rheumatoid arthritis and the like of human and mammal.

The following Reference Examples, Examples, Preparations and Experiments further illustrate this aspect of the present invention in detail but are not to be construed to limit the scope thereof. In the Reference Examples, Examples and Preparations, "room temperature" is 15° to 25° C.

Reference Example 1'

(1) Synthesis of 5-[2-(methylsulfonyloxy)ethylthio]imidazo[1,2-a]pyridine

To a solution of 5-(2-hydroxy)ethylthioimidazo[1,2-a]pyridine (9.71 g, 50 mmoles) and triethylamine (10.5 ml, 75.3 mmoles) in methylene chloride (300 ml) was added methanesulfonyl chloride (4.26 ml, 55 mmoles) under ice-cooling with stirring and the mixture was stirred under ice-cooling for 2 hours. The reaction mixture was washed in turn with aqueous saturated sodium bicarbonate and saturated saline and dried over anhydrous magnesium sulfate. Then, the solvent was distilled off to obtain 13.6 g of the desired product (quantitative, brown oily product).

NMR (200MHz, CDCl$_3$) δ: 2.97 (3H, s), 3.28 (2H, t, J=6.4Hz), 4.35 (2H, t, J=6.4Hz), 7.08 (1H, dd, J=7, 1.2Hz), 7.18 (1H, dd, J=8.8, 7Hz), 7.64 (1H, m), 7.73 (1H, d, J=1.4Hz), 7.91 (1H, m).

Reference Example 2'

(1) Synthesis of 5-[2-(methylamino)ethylthio]imidazo[1,2-a]pyridine

A solution of 5-[2-(methylsulfonyloxy)etylthio]imidazo[1,2-a]pyridine (2.18 g, 8 mmoles), triethylamine (2.24 ml, 16 mmoles) and a 40% methylamine-methanol solution (20 ml) in chloroform (20 ml) was heated at reflux for 3 hours. The reaction mixture was washed with 3N NaOH and dried over anhydrous magnesium sulfate. After the solvent was distilled off, the residue was purified by column chromatography [eluent: methanol/chloroform (1:10)] to obtain 781 mg of the desired product (47.1%, light brown oily product).

NMR (200MHz, CDCl$_3$) δ: 2.31 (1H, br), 2.88 (2H, t, J=6.4Hz), 3.16 (2H, t, J=6.4Hz), 6.94 (1H, dd, J=7, 1Hz), 7.15 (1H, dd, J=9, 7Hz), 7.58 (1H, dd, J=9, 1Hz), 7.69 (1H, d, J=1.2Hz).

IR (KBr) cm$^{-1}$: 3290, 3105, 2930, 2850, 2790, 1655, 1615, 1530, 1490.

According to the same manner as that described in Reference Example 2' (1), the following compound was obtained.

(2) 5-[2-(Ethylamino)ethylthio]imidazo[1,2-a]pyridine

NMR (200MHz, CDCl$_3$) δ: 1.11 (3H, t, J=7Hz), 1.88 (1H, br), 2.70 (2H, m), 2.90 (2H, t, J=6.2Hz), 3.15 (2H, t, J=6.2Hz), 6.94 (1H, dd, J=7, 1Hz), 7.16 (1H, dd, J=9, 7Hz), 7.59 (1H, dd, J=9, 1Hz), 7.70 (1H, d, J=1.2Hz), 7.87 (1H, s).

IR (KBr) cm$^{-1}$: 3280, 3105, 2965, 2930, 2890, 2820, 1655, 1620, 1530, 1490.

Reference Example 3'

(1) Synthesis of 5-[2-(amino)ethylthio]imidazo[1,2-a]pyridine

After a suspension of 5-[2-(amino)ethylthio]imidazo-[1,2-a]pyridine dihydrochloride (13.31 g, 50 mmloes) in chloroform (200 ml) was washed with 3N sodium hydroxide (50 ml), the aqueous layer was extracted with chloroform, the combined chloroform layer was dried over anhydrous magnesium sulfate. Then, the solvent was distilled off to obtain 9.63 g of the desired product (99.7%, pale yellow oily product).

NMR (200MHz, CDCl$_3$) δ: 1.67 (2H, br), 2.95 (2H, m), 3.08 (2H, m), 6.95 (1H, d, J=7Hz), 7.15 (1H, dd, J=9.2, 7Hz), 7.59 (1H, d, J=9.2Hz), 7.71 (1H, s), 7.88 (1H, s).

Reference Example 4'

Synthesis of 5-[3-(amino)propylthio]imidazo[1,2-a]pyridine

To a mixed solution of 10% (w/w) potassium hydroxide (69.3 g, 105 mmoles) and dimethylsulfoxide (50 ml) was added S-(3-aminopropyl)isothiourea dihydrobromide (8.85 g, 39 mmoles) and the mixture was stirred at room temperature for 1.5 hours. To the reaction mixture was added 5-chloroimidazo[1,2-a]pyridine (3.05 g, 20 mmoles), followed by stirring at room temperature and additionally at 65° C. for 20 hours. Water was added to the reaction mixture, which was extracted with chloroform, washed with 1N sodium hydroxide several times and dried over anhydrous magnesium sulfate. Then, the solvent was distilled off to obtain 2.66 g of the desired product (64.3%, pale yellow oily product).

NMR (200MHz, CDCl$_3$) δ: 1.29 (2H, br), 1.80 (2H, m), 2.85 (2H, t, J=6.8Hz), 3.08 (2H, t, J=7.2Hz), 6.91 (1H, dd, J=7, 1Hz), 7.16 (1H, dd, J=9, 7Hz), 7.58 (1H, d, J=9, 1Hz), 7.71 (1H, d, J=1.2Hz), 7.85 (1H, d, J=1.2Hz).

EXAMPLE 1'

(1) Synsthesis of 5-[2-(methoxycarbonylamino)ethylthio]imidazo[1,2-a]pyridine (Compound 1')

To a solution of 5-[2-(amino)ethylthio]imidazo[1,2-a]pyridine (1.93 g, 10 mmoles) and triethylamine (1.53 ml, 11 mmoles) in methylene chloride (30 ml) was added methyl chloroformate (0.77 ml, 10 mmoles) under ice-cooling with stirring and the mixture was stirred at room temperature for 20 minutes. The reaction mixture was washed in turn with aqueous sodium bicarbonate and water and dried over anhydrous magnesium sulfate. After the solvent was distilled off, the residue was purified by column chromatography [eluent: ethanol/etyl acetate (1:10)] to obtain 1.68 g of the desired product (66.9%, colorless crystals).

Melting point: 198°-200.0° C.

Elemental analysis for $C_{11}H_{13}N_3O_2S$, Calcd.: C, 52.57; H, 5.21; N, 16.72. Found: C, 52.68; H, 5.22; N, 16.60.

NMR (200MHz, CDCl₃) δ: 3.12 (2H, m), 3.40 (2H, m), 3.68 (3H, s), 5.10 (1H, br), 7.00 (1H, d, J=7Hz), 7.16 (1H, dd, J=9, 7Hz), 7.61 (1H, d, J=9Hz), 7.72 (1H, s), 7.87 (1H, s).

According to the same manner as that described in Example 1' (1), the following compounds were obtained.

(2)

5-[2-(Ethoxycarbonylamino)ethylthio]imidazo[1,2-a]pyridine (Compound 2')

Melting point: 68°–70° C.

Elemental analysis for $C_{12}H_{15}N_3O_2S$, Calcd.: C, 54.32; H, 5.70; N, 15.84. Found: C, 54.33; H, 5.75; N, 15.83.

(3)

5-[2-(Propyloxycarbonylamino)ethylthio]imidazo[1,2-a]pyridine (Compound 3')

Melting point: 62°–64° C.

Elemental analysis for $C_{13}H_{17}N_3O_2S$, Calcd.: C, 55.89; H, 6.13; N, 15.04. Found: C, 55.87; H, 6.09; N, 14.96.

NMR (200MHz, CDCl₃) δ: 0.92 (3H, t, J=7.4Hz), 1.62 (2H, m), 3.14 (2H, t, J=6.6Hz), 3.42 (1H, m), 4.01 (1H, t, J=6.6Hz), 5.07 (1H, br), 7.02 (1H, d, J=7Hz), 7.17 (1H, dd, J=9, 7Hz), 7.60 (1H, d, J=9Hz), 7.71 (1H, d, J=1.2Hz), 7.86 (1H, s).

IR (KBr) cm⁻¹: 3210, 3025, 2965, 1695, 1620, 1545, 1490, 1275.

(4)

5-[2-(Butyloxycarbonylamino)ethylthio]imidazo[1,2-a]pyridine (Compound 4')

Melting point: 75°–76° C.

Elemental analysis for $C_{14}H_{19}N_3O_2S$, Calcd.: C, 57.31; H, 6.53; N, 14.32. Found: C, 57.32; H, 6.55; N, 14.23.

NMR (200MHz, CDCl₃) δ: 0.93 (3H, t, J=7Hz), 1.35 (2H, m), 1.58 (2H, m), 3.14 (2H, t, J=6.4Hz), 3.41 (2H, m), 4.05 (2H, t, J=6.6Hz}, 5.04 (1H, br), 7.16 (1H, dd, J=9, 7Hz), 7.60 (1H, d, J=9Hz), 7.71 (1H, d, 1.2Hz), 7.85 (1H, s).

IR (KBr) cm⁻¹: 3490, 3210, 2970, 1695, 1615, 1500, 1285.

(5)

5-[2-(Isopropyloxycarbonylamino)ethylthio]imidazo[1,2-a]pyridine (Compound 5')

Melting point: 80.0°–81.0° C.

Elemental analysis for $C_{13}H_{17}N_3O_2S$, Calcd.: C, 55.89; H, 6.13; N, 15.04. Found: C, 55.85; H, 6.14; N, 14.96.

NMR (200Hz, CDCl₃) δ: 1.22 (6H, d, J=6.2Hz), 3.14 (2H, t, J=6.4Hz), 3.41 (2H, m), 4.94 (1H, br), 7.02 (1H, d, J=7Hz), 7.17 (1H, dd, J=9, 7Hz), 7.61 (1H, d, J=9, 7Hz), 7.71 (1H, d, J=1.4Hz), 7.86 (1H, s).

IR (KBr) cm⁻¹: 3220, 3025, 2970, 1705, 1630, 1545, 1300, 1240.

(6)

5-[2-(Isobutyloxycarbonylamino)ethylthio]imidazo[1,2-a]pyridine (Compound 6')

Melting point: 75°–76° C.

Elemental analysis for $C_{14}H_{19}N_3O_2S$, Calcd.: C, 57.31; H, 6.53; N, 1432. Found: C, 57.29; H, 6.53; N, 14.41.

NMR (200Hz, CDCl₃) δ: 0.91 (6H, d, J=6.8Hz), 1.89 (1H, m), 3.14 (2H, t, J=6.4Hz), 3.42 (2H, m), 3.84 (2H, t, J=6.6Hz), 5.15 (1H, br), 7.01 (1H, dd, J=7Hz), 7.16 (1H, dd, J=9, 7Hz), 7.59 (1H, d, J=9Hz), 7.70 (1H, d, J=1.2Hz), 7.85 (1H, s).

(7)

5-[2-(Allyloxycarbonylamino)ethylthio]imidazo[1,2-a]pyridine (Compound 7')

Melting point: 72.5°–73.5° C.

Elemental analysis for $C_{13}H_{15}N_3O_2S$, Calcd.: C, 56.30; H, 5.45; N, 15.15. Found: C, 56.34; H, 5.44; N, 15.04.

NMR (200Hz, CDCl₃) δ: 3.15 (2H, t, J=6.4Hz), 3.43 (2H, m), 4.56 (2H, m), 5.07 (1H, br), 5.18–5.36 (2H, m), 5.90 (1H, m), 7.02 (1H, d, J=7Hz), 7.17 (1H, dd, J=9, 7Hz), 7.61 (1H, d, J=9Hz), 7.72 (1H, d, J=1.4Hz), 7.86 (1H, m).

IR (KBr) cm⁻¹: 3205, 3020, 1700, 1625, 1570, 1490, 1270.

(8)

5-[2-[2,2,2-(Trichloro)ethoxycarbonylamino]ethylthio]imidazo[1,2-a]pyridine (Compound 8')

Melting point: 113.0°–114.0° C.

Elemental analysis for $C_{12}H_{12}N_3O_2SCl_3$, Calcd.: C, 39.10; H, 3.28; N, 11.4. Found: C, 39.23; H, 3.27; N, 11.25.

NMR (200Hz, CDCl₃) δ: 3.17 (2H, t, J=6.4Hz), 3.48 (2H, m), 4.73 (2H, s), 5.52 (1H, br), 7.03 (1H, d, J=7Hz), 7.17 (1H, dd, J=9, 7Hz), 7.62 (1H, d, J=9Hz), 7.71 (1H, d, J=1.2Hz), 7.87 (1H, m).

IR (KBr) cm⁻¹: 3195, 2975, 1725, 1615, 1545, 1485, 1260, 1210.

(9)

5-[2-(Benzyloxycarbonylamino)ethylthio]imidazo[1,2-a]pyridine (Compound 9')

Melting point: 52.0°–53.0° C.

Elemental analysis for $C_{17}H_{17}N_3O_2S$, Calcd.: C, 62.36; H, 5.23; N, 12.83. Found: C, 62.34; H, 5.22; N, 12.75.

NMR (200Hz, CDCl₃) δ: 3.14 (2H, t, J=6.4Hz), 3.43 (2H, m), 5.09 (2H, s), 5.17 (1H, br), 6.99 (1H, d, J=6.8Hz), 7.13 (1H, dd, J=9.2, 6.8Hz), 7.35 (5H, s), 7.59 (1H, d, J=9.2Hz), 7.69 (1H, s), 7.84 (1H, s).

(10)

5-[2-[(9-Fluorenyl)methyloxycarbonylamino]ethylthio]imidazo[1,2-a]pyridine (Compound 10')

Melting point: 105.0°–108.0° C.

Elemental analysis for $C_{24}H_{21}N_3O_2S \cdot 0.4H_2O$, Calcd.: C, 69.07; H, 5.05; N, 9.67. Found: C, 69.14; H, 5.23; N, 9.96.

NMR (200MHz, CDCl₃) δ: 3.13 (2H, t, J=6Hz), 3.42 (2H, m), 4.21 (1H, t, J=6.6Hz), 4.43 (2H, d, J=6.6Hz), 5.17 (1H, br), 7.01 (1H, d, J=7.4Hz), 7.15 (1H, dd, J=8.6, 7.4Hz), 7.29–7.46 (4H, m), 7.53–7.65 (3H, m), 7.60–7.87 (4H, m).

IR (KBr) cm⁻¹: 3205, 3020, 1710, 1625, 1550, 1485, 1450, 1270.

(11)
5-[2-(Phenoxycarbonylamino)ethylthio]imidazo[1,2-a]pyridine (Compound 11')

Melting point: 96.0°-97.0° C.
Elemental analysis for $C_{16}H_{15}N_3O_2S$, Calcd.: C, 61.32; H, 4.82; N, 13.41. Found: C, 61.35; H, 4.86; N, 13.30.
IR (KBr) cm$^{-1}$: 3200, 3005, 1725, 1615, 1555, 1485, 1270, 1210.

(12)
5-[2-(N-Methyl-N-isopropyloxycarbonylamino)ethythio]imidazo[1,2-a]pyridine (Compound 12')

NMR (200MHz, CDCl$_3$) δ: 1.02-1.35 (6H, m), 2.91 (3H, s), 3.05-3.26 (2H, m), 3.38-3.60 (2H, m), 4.89 (1H, m), 7.01 (1H, br), 7.18 (1H, dd, J=9, 7Hz), 7.60 (1H, d, J=9Hz), 7.71 (1H, s), 7.84 (1H, s).
IR (KBr) cm$^{-1}$: 3220, 3025, 2970, 1705, 1630, 1545.

(13)
5-[2-(N-Ethyl-N-isoporpyooxycarbonylamino)ethylthio]imidazo[1,2-a]pyridine (Compound 13')

NMR (200MHz, CDCl$_3$) δ: 0.95-1.35 (9H, m), 3.02-3.68 (6H, m), 4.90 (1H, m), 7.04 (1H, m), 7.19 (1H, dd, J=9, 7Hz), 7.60 (1H, d, J=9Hz), 7.72 (1H, s), 7.83 (1H, s).
IR (KBr) cm$^{-1}$: 3220, 3025, 2970, 1705, 1630, 1545.

(14)
5-[3-(Methoxycarbonylamino)propylthio]imidazo[1,2-a]pyridine (Compound 14')

Melting point: 69.0°-70.0° C.
Elemental analysis for $C_{12}H_{15}N_3O_2S$, Calcd.: C, 54.32; H, 5.70; N, 15.84. Found: C, 54.48; H, 5.74; N, 15.72.
NMR (200MHz, CDCl$_3$) δ: 1.85 (2H, m), 3.02 (2H, t, J=7Hz), 3.32 (2H, m), 3.67 (3H, s), 4.85 (1H, br), 6.91 (1H, dd, J=7, 1.2Hz), 7.15 (1H, dd, J=9, 7Hz), 7.58 (1H, d, J=9Hz), 7.70 (1H, d, J=1.2Hz), 7.84 (1H, s).

(15)
5-[3-(isopropyloxycarbonylamino)propylthio]imidazo[1,2-a]pyridine (Compound 15')

NMR (200MHz, CDCl$_3$) δ: 1.22 (6H, d, J=6.2Hz), 1.85 (2H, m), 3.03 (2H, m), 3.31 (2H, m), 4.82 (1H, br), 4.90 (1H, heptet, J=6.2Hz), 6.90 (1H, dd, J=7, 1Hz), 7.15 (1H, dd, J=9, 7Hz), 7.57 (1H, m), 7.69 (1H, d, J=1.4Hz), 7.84 (1H, m).
IR (KBr) cm$^{-1}$: 3210, 3025, 2965, 1695, 1620, 1545, 1490, 1275.

(16)
5-[1-(tert-Butoxycarbonyl)-4-piperidylthio]imidazo[1,2-a]pyridine (Compound 16')

NMR (200MHz, CDCl$_3$) δ: 1.45 (9H, s), 1.50-1.98 (4H, m), 2.90 (2H, m), 3.36 (1H, m), 3.98 (2H, m), 7.03 (1H, dd, J=7, 1.2Hz), 7.15 (1H, dd, J=9, 7Hz), 7.64 (1H, m), 7.70 (1H, d, J=1.2Hz), 7.96 (1H, m).

(17)
5-[1-(Isopropyloxycarbonyl)-4-piperidylthio]imidazo[1,2-a]pyridine (Compound 17')

NMR (200MHz, CDCl$_3$) δ: 1.23 (6H, d, J=6.2Hz), 1.50-1.98 (4H, m), 2.94 (2H, m), 3.37 (1H, m), 4.03 (2H, m), 4.91 (1H, heptet, J=6.2Hz), 7.03 (1H, dd, J=7, 1.2Hz), 7.16 (1H, dd, J=9, 7Hz), 7.65 (1H, d, J=9Hz), 7.71 (1H, d, J=1.2Hz), 7.97 (1H, s).

EXAMPLE 2'

(1) Synthesis of 3-bromo-5-[2-(isopropyloxycarbonylamino)ethylthio]imidazo[1,2-a]pyridine (Compound 18')

To a solution of 5-[2-(isopropyloxycarbonylamino)ethylthio]imidazo[1,2-a]pyridine (279 mg, 1 mmole) in chloroform (5 ml) was added N-bromosuccinimide (187 ml, 1.05 mmoles) and the mixture was stirred at room temperature for 1 hour. The reaction solution was washed with water and dried over anhydrous magnesium sulfate. After the solvent was distilled off, the residue was purified by column chromatography (eluent: ethyl acetate) to obtain 296 mg of the desired product (82.7%, colorless solid).

Melting point: 103.0°-104.0° C.
Elemental analysis for $C_{13}H_{16}N_3O_2SBr$, Calcd.: C, 43.58; H, 4.50; N, 11.73. Found: C, 43.60; H, 4.53; N, 11.74.
NMR (200MHz, CDCl$_3$) δ: 1.22 (6H, d, J=6.2Hz), 3.11 (2H, t, J=6.6Hz), 3.42 (2H, m), 4.90 (1H, heptet, J=6.2Hz), 4.96 (1H, br), 7.00 (1H, dd, J=7, 1.2Hz), 7.14 (1H, dd, J=8.8, 7Hz), 7.57 (1H, dd, J=8.8, 1.2Hz), 7.59 (1H, s).

According to the same manner as that described in Example 2' (1), the following compound was obtained.

(2) 3-Chloro-5-[2-(isopropyloxycarbonylamino)ethylthio]imidazo[1,2-a]pyridine (Compound 19')

Melting point: 113.0°-114.0° C.
Elemental analysis for $C_{13}H_{16}N_3O_2SCl.0.2H_2O$, Calcd.: C, 49.19; H, 5.21; N, 13.24. Found: C, 49.38; H, 5.26; N, 13.22.
NMR (200Hz, CDCl$_3$) δ: 1.22 (6H, d, J=6.4Hz), 3.12 (2H, t, J=6.4Hz), 3.43 (2H, m), 4.90 (1H, heptet, J=6.4Hz), 4.96 (1H, br), 6.99 (1H, dd, J=7.2, 1.2Hz), 7.10 (1H, dd, J=8.8, 7.2Hz), 7.53 (1H, dd, J=8.8, 1.2Hz), 7.54 (1H, s).

EXAMPLE 3'

(1) Synthesis of 5-[2-(isopropyloxycarbonylamino)ethylthio]-3-morpholinomethylimidazo[1,2-a]pyridine (Compound 20')

To a solution of an aqueous 37% formalin solution (210 mg, 2.59 mmoles) in acetic acid (2 ml) was added morpholine (226 μl, 2.59 mmoles) under ice-cooling and the mixture was stirred at room temperature for 45 minutes. 5-[2-(isopropyloxycarbonylamino)ethylthio]imidazo[1,2-a]pyridine (651 mg, 2.33 mmoles) was added, followed by stirring at 60° C. for 2 hours. After the solvent was distilled off, the residue was diluted with chloroform, washed in turn with aqueous 1N NaOH and saturated saline, and then dried over anhydrous magnesium sulfate. After the solvent was distilled off, the residue was purified by column chromatography [eluent: ethanol/ethyl acetate=1:10] to obtain 442 mg of the desired product (50.1%, light brown solid).

NMR (200MHz, CDCl$_3$) δ: 0.96 (6H, d, J=6.2Hz), 2.56 (4H, m), 3.26 (2H, m), 3.36 (2H, m), 3.69 (4H, m), 4.10 (2H, s), 4.59 (1H, heptet, J=6.2Hz), 6.85 (1H, br), 7.01 (1H, d, J=5Hz), 7.13 (1H, dd, J=8.6, 6.6Hz), 7.51 (1H, s), 7.53 (1H, d, J=8.6Hz).

EXAMPLE 4'

Synthesis of 5-[2-(isopropyloxycarbonylamino)ethylthio]imidazo[1,2-a]pyridine hydrochloride (Compound 21')

A solution of 5-[2-(isopropyloxycarbonylamino)ethylthio]imidazo[1,2-a]pyridine (279 mg, 1 mmoles) in methanol (10 ml) was treated with hydrogen chloridemethanol. After the solvent was distilled off, the residue was crystallized from isopropanol-ethyl acetate-methanol. The crystals thus obtained were washed with water and dried to obtain 290 mg of the desired product (92.1%, colorless crystals).

Melting point: 145°–150° C.

Elemental analysis for $C_{13}H_{17}N_3O_2S$ HCl, Calcd.: C, 49.44; H, 5.74; N, 13.30. Found: C, 49.51; H, 5.64; N, 13.14.

EXAMPLE 5'

Synthesis of 5-[4-(isopropyloxycarbonylamino)butylthio]imidazo[1,2-a]pyridine (Compound 22')

To 5-(4-amino)butylthioimidazo[1,2-a]pyridine (370 mg, 1.67 mmoles) and triethylamine (0.35 ml, 2.51 mmoles) in methylene chloride (20 ml) was added isopropyl chloroformate (0.25 g, 2.04 mmoles) under ice-cooling with stirring and the mixture was stirred under ice-cooling for 1 hour. The reaction mixture was washed in turn with aqueous saturated sodium bicarbonate and saturated saline, and then dried over anhydrous magnesium sulfate. After the solvent was distilled off, the residue was purified by column chromatography (eluent: ethyl acetate) to obtain 215 mg of the desired product (41.8%, light tan oily product).

NMR (200MHz, CDCl$_3$) δ: 1.22 (6H, d, J=6.2Hz), 1.54–1.72 (4H, m), 3.02 (2H, m), 3.18 (2H, m), 4.66 (1H, br), 4.90 (1H, heptet, J=6.2Hz), 6.90 (1H, dd, J=7, 1Hz), 7.15 (1H, dd, J=9, 7Hz), 7.58 (1H, d, J=9Hz), 7.70 (1H, m), 7.84 (1H, m).

| Preparation 1' | |
|---|---|
| (1) Compound 5' | 50 g |
| (2) Lactose | 100 g |
| (3) Corn starch | 15 g |
| (4) Carboxymethylcellulose calcium | 44 g |
| (5) Magnesium stearate | 1 g |
| 1000 tablet | 210 g |

All the components (1), (2) and (3) and 30 g of the component (4) were kneaded with water, dried under vacuum and granulated. This granulated powder was mixed with 14 g of the component (4) and 1 g of the component (5) and the mixture was charged in a tableting machine to produce 1000 tablets containing 50 mg of the component (1) per one tablet.

Preparation 2'

An ointment was prepared by uniformly kneading the following components.

| | |
|---|---|
| Compound 5' | 0.5 g |
| Liquid paraffin | 1 g |
| White petrolatum | suitable amount |
| Total amount | 100 g |
| Preparation 3' | |
| (1) Compound 5' | 1 g |
| (2) Cacao fat | 19 g |

All the components (1) and (2) were kneaded on a water bath at about 60° C. Then, the mix was charged in a suppository mold and cooled to produce 10 suppositories, each containing 2 g of the mixture.

| Preparation 4' | |
|---|---|
| (1) Compound 5' | 10 g |
| (2) Lactose | 4.5 g |
| (3) Corn starch | 4.5 g |
| (4) Magnesium stearate | 1 g |
| 1000 capsules | 20 g |

All the components were thoroughly admixed and the mixture was filled in a suitable gelatin capsule to produce 100 capusules contaning 100 mg of the component (1) per one capsule.

Preparation 5'

An injection preparation filled in an ampoule was prepared by admixing and dissoving the following components.

| | per one ampoule |
|---|---|
| Compound 21' | 50 mg |
| Sodium chloride | 18 mg |
| Distilled water for injection | suitable amount |
| Total amount | 2 ml |

Experiment 1'

Effect of the desired compound on growth of endothelial cells

This experiment was conducted by using endothelial cells (HUVE cells) obtained from human umbilical vein. $2 \times 10^3$ HUVE cells were suspended in a complete medium prepared by adding 2.5% FBS (fetal bovine serum) to GIT medium (manufactured by Nihon Seiyaku K.K.). Then, the suspension was distributed in a 96-well microtiter plate, which was cultivated at 37° C. in an atmosphere of 5% carbon dioxide-7% oxygen-88% nitrogen. After 24 hours, human recombinant basic FGF (endothelial cell growth factor) was added thereto in the final concentration of 2 ng/ml and a test compound was further added, followed by cultivation for 3 days. After cultivation, growth rate of HUVE cells was measured by MTT method [Canser Treatment Reports, Vol. 71, page 1141–1149, 1987].

The test compounds inhibited growth of human umbilical endothelial cells.

IC$_{50}$ value (the concentration of the test compound inhibiting growth of endothelial cells by 50%) of the test compound was determined from a graph of growth curve of HUVE cells. The results are shown in Table 1'.

TABLE 1'

| Test compound | IC$_{50}$ (μM) |
|---|---|
| 1' | 18 |
| 2' | 7 |
| 3' | 27 |
| 5' | 4 |
| 7' | 29 |
| 8' | 12 |
| 10' | 43 |

TABLE 1'-continued

| Test compound | IC$_{50}$ (μM) |
|---|---|
| 18' | 20 |
| 19' | 6 |
| 21' | 5 |

As shown in Table 1', the compounds of the present invention have excellent inhibitory activity of endotherial cells growth.

Experiment 2'

Effect of the desired compound on growth of bovine artery endotherial cells

This experiment was conducted by using endotherial cells (BAE cells) derived from bovine aorta. $5 \times 10^3$ BAE cells were suspended in a complete medium prepared by adding 5% FBS (fetal bovine serum) to Dulbecco's modified Eagle's minimum essential medium (D-MEM medium). Then, the suspension was distributed in a 96-well microtiter plate, which was cultivated at 37° C. in an atmosphere of 5% carbon dioxide-95% air. After 24 hours, human recombinant basic FGF (endotherial cell growth factor) was added thereto in the final concentration of 2 ng/ml and a test compound was further added, followed by cultivation for 3 days. After cultivation, growth rate of BAE cells was measured by MTT method [Canser Treatment Reports, Vol. 71, page 1141-1149, 1987].

The test compounds inhibited growth of bovine artery endotherial cells.

IC$_{50}$ value (the concentration of the test compond inhibiting growth of endothelial cells by 50%) of Compound 1' was 48 μM.

Experiment 3'

Effect of the desired compound on growth of human umbilical vein endotherial cells by phorbol ester This experiment was conducted by using endothelial cells (HUVE cells) obtained from human umbilical vein. $2 \times 10^3$ HUVE cells were suspended in a complete medium prepared by adding 2.5% FBS (fetal bovine serum) to GIT medium (manufactured by Nihon Seiyaku K.K.). Then, the suspension was distributed in a 96-well microtiter plate, which was cultivated at 37° C. in an atmosphere of 5% carbon dioxide-7% oxygen-88% nitrogen. After 24 hours, 12-O-tetradecanoylphorbol 13-acetate (TPA) was added thereto in the final concentration of 1 nM and a test compound was added, followed by cultivation for 3 days. After cultivation, growth rate of HUVE cells was measured by MTT method [Canser Treatment Reports, Vol. 71, page 1141-1149, 1987].

The test compounds inhibited growth of human umbilical endotherial cells by phorbol ester.

IC$_{50}$ value (the concentration of the test compond inhibiting growth of endothelial cells by 50%) of Compound 1 was 15 μM.

Experiment 4'

Effect of the desired compound on inhibition of increse in intracellular calcium concentration by phorbol ester Bovine aorta endotherial cells (BAE cells) were cultivated on a cover glass loaded with 4 μM Flar 2 (manufactured by Dojin Kagaku Kenkyusho) and inserted into a quartz cuvette containing 2.5 ml of HEPES buffer (pH 7.5).

The quartz cubette was fixed so that the cover glass was positioned on the diagonal side at angles of 45° to the incident direction of an excited light.

Fluormetry was conducted with a spectrophotofluorometer F-4000 (manufactured by Hitachi Seisakusho K.K.). Excitation was obtained at 340 nm and 380 nm and fluorescence of 505 nm was recorded.

Fmax was determined by Ionomicine (2 μM, manufactured by Carbairochen Co.) which was a calcium ionophore and Fmin was determined by EGTA (8 mM) which was a chelating agent of calcium ion.

Intracellular calcium ion concentration [Ca$^{++}$]i was calculated by the following formula:

$$[Ca^{++}]i = Kd \times (R - Rmin) \times Sf_2/((Rmax - R) \times Sb_2R = \{D(W_1) - AutoF_1\}/\{D(W_2) - AutoF_2\}$$

wherein D (W$_1$) a measured value of excited wavelength W$_1$; D (W$_2$): a measured value of excited wavelength W$_2$; AutoF$_1$: autofluorescence at W$_1$; AutoF$_2$: autofluorescence at W$_2$; Rmin: R (Ca$^{++}$=0)=Fmin (W$_1$)/Fmin (W$_2$); Rmax: R (saturated Ca$^{++}$ concentration)=Fmax (W$_1$)/Fmax (W$_2$); Sf$_2$: fluorescence intensity in a free state at W$_2$; Sb$_2$: fluorescenec intensity in Ca$^{++}$ bound state at W$_2$, which was obtained by correcting the formula of Zehn et al.:

$$[Ca^{++}]i = Kd \times (F - Fmin)/(Fmax - F)$$

by taking Kd as 224 nM.

The experiment was conducted by adding a test compound at various concentrations to a solution in a cuvette and incubated for 5 minutes. Then, 12-O-tetradecanoylphorbol 13-acetate (TPA) of 2 nM in the final concentration was added and change of fluorescence intensity was observed.

It was found that the test compunds inhibited increase in intracellular calcium concentration by phorbol ester (TPA).

Change of inhibitory activity due to change of the concentration of Compound 1' is shown in Table 2'.

TABLE 2'

Effect of Compound 1' on inhibition of increase in intracellular calcium concentration by phorbol ester

| Concentration of Compound (M) | Inhibitory activity (%) |
|---|---|
| $8 \times 10^{-6}$ | 100 |
| $8 \times 10^{-7}$ | 88 |
| $8 \times 10^{-8}$ | 81 |

What is claimed is:
1. A compound of the formula (I'):

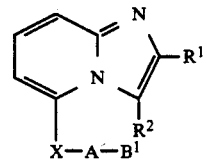

(I')

wherein X is S, S(O), S(O)$_2$, O or NR$^3$ wherein R$^3$ is selected from the group consisting of
(a) a straight or branched alkyl group having 1 to 6 carbon atoms which may be substituted with 1 to 4 substituents selected from the group consisting of halogen, nitro, amino, mono- or dialkylamino of which alkyl moiety has 1 to 6 carbon atoms, 4 to 7 membered cyclic amino, straight or branched alkoxy having 1 to 6 carbon atoms, aryloxy having 6 to 10 carbon atoms, carbamoyl, cyano, hydroxy, carboxy, alkoxycarbonyl of which alkoxy moiety has 1 to 6 carbon atoms and mono- or dialkylcarbamoyl of which alkyl moiety has 1 to 6 carbon atoms, (b) a straight or branched alkenyl group having 2 to 6 carbon atoms which may be substituted with 1 to 4 substituents selected from the group consisting of halogen, nitro, amino, mono- or dialkylamino or which alkyl moiety has 1 to 6 carbon atoms, 4 to 7 membered cyclic amino, straight or branched alkoxy having 1 to 6 carbon atoms, aryloxy having 6 to 10 carbon atoms, carbamoyl, cyano, hydroxy, carboxy, alkoxycarbonyl of which alkoxy moiety has 1 to 6 carbon atoms and mono- or dialkylcarbamoyl of which alkyl moiety has 1 to 6 carbon atoms, (c) a phenylalkyl group of which alkyl moiety has 1 to 6 carbon atoms, and of which phenyl moiety may be substituted with 1 to 4 substituents selected from the group consisting of halogen, straight or branched alkyl having 1 to 6 carbon atoms, straight or branched alkenyl having 2 to 6 carbon atoms, straight or branched alkoxy having 1 to 6 carbon atoms, nitro, cyano, hydroxy, alkoxycarbonyl of which alkoxy moiety has 1 to 6 carbon atoms and mono- or dialkylcarbamoyl of which alkyl moiety has 1 to 6 carbon atoms, (d) a naphthylalkyl group of which alkyl moiety has 1 to 6 carbon atoms, and of which naphthyl moiety may be substituted with 1 to 4 substituents selected from the group consisting of halogen, straight or branched alkyl having 1 to 6 carbon atoms, straight or branched alkenyl having 2 to 6 carbon atoms, straight or branched alkoxy having 1 to 6 carbon atoms, nitro, cyano, hydroxy, alkoxycarbonyl of which alkoxy moiety has 1 to 6 carbon atoms and mono- or dialkylcarbamoyl of which alkyl moiety has 1 to 6 carbon atoms (e) hydrogen; A is a divalent straight or branched $C_{1-15}$ hydrocarbon group which may contain an ethereal oxygen at any possible position and may have a substituent at a branched part of the hydrocarbon group wherein the substituent is $C_{1-6}$ alkyl, $C_{2-6}$ alkenyl, phenyl-$C_{1-6}$ alkyl, naphthyl-$C_{1-6}$ alkyl or $C_{4-24}$ aryl; $B^1$ is an amino group acylated by an acyl group derived from a carboxylic acid having 2 or more carbon atoms, a sulfonic acid, a carbamic acid or a thiocarbamic acid; and $R_1$ and $R_2$ are the same or different and are (a) a straight or branched alkyl group having 1 to 6 carbon atoms which may be substituted with 1 to 4 substituents selected from the group consisting of halogen, nitro, amino, mono- or dialkylamino of which alkyl moiety has 1 to 6 carbon atoms, 4 to 7 membered cyclic amino, straight or branched alkoxy having 1 to 6 carbon atoms, aryloxy having 6 to 10 carbon atoms, carbamoyl, cyano, hydroxy, carboxy, alkoxycarbonyl of which alkoxy moiety has 1 to 6 carbon atoms and mono- or dialkylcarbamoyl of which alkyl moiety has 1 to 6 carbon atoms, (b) a straight or branched alkenyl group having 2 to 6 carbon atoms which may be substituted with 1 to 4 substituents selected from the group consisting of halogen, nitro, amino, mono- or dialkylamino or which alkyl moiety has 1 to 6 carbon atoms, 4 to 7 membered cyclic amino, straight or branched alkoxy having 1 to 6 carbon atoms, aryloxy having 6 to 10 carbon atoms, carbamoyl, cyano, hydroxy, carboxy, alkoxycarbonyl of which alkoxy moiety has 1 to 6 carbon atoms and mono- or dialkylcarbamoyl of which alkyl moiety has 1 to 6 carbon atoms, (c) a phenylalkyl group of which alkyl moiety has 1 to 6 carbon atoms, and of which phenyl moiety may be substituted with 1 to 4 substituents selected from the group consisting of halogen, straight or branched alkyl having 1 to 6 carbon atoms, straight or branched alkenyl having 2 to 6 carbon atoms, straight or branched alkoxy having 1 to 6 carbon atoms, nitro, cyano, hydroxy, alkoxycarbonyl of which alkoxy moiety has 1 to 6 carbon atoms and mono- or dialkylcarbamoyl of which alkyl moiety has 1 to 6 carbon atoms, (d) a naphthylalkyl group of which alkyl moiety has 1 to 6 carbon atoms, and of which naphthyl moiety may be substituted with 1 to 4 substituents selected from the group consisting of halogen, straight or branched alkyl having 1 to 6 carbon atoms, straight or branched alkenyl having 2 to 6 carbon atoms, straight or branched alkoxy having 1 to 6 carbon atoms, nitro, cyano, hydroxy, alkoxycarbonyl of which alkoxy moiety has 1 to 6 carbon atoms and mono- or dialkylcarbamoyl of which alkyl moiety has 1 to 6 carbon atoms, (e) an aryl group having 4 to 24 carbon atoms which may be substituted with 1 to 4 substituents selected from the group consisting of halogen, straight or branched alkyl having 1 to 6 carbon atoms, straight or branched alkenyl having 2 to 6 carbon atoms, straight or branched alkoxy having 1 to 6 carbon atoms, nitro, cyano, oxo, hydroxy, amino, alkoxycarbonyl or which alkoxy moiety has 1 to 6 carbon atoms, carbamoyl and mono- or dialkylcarbamoyl of which alkyl moiety has 1 to 6 carbon atoms, (f) amino, (g) acylamino of which acyl moiety is a group of the formula $-CO-R^{16}$, $-COOR^{16}$, $-SO_2R^{17}$, $CO-NR^{14}R^{15}$ or $-CSNR^{14}R^{15}$, wherein $R^{14}$ and $R^{15}$ are (i) hydrogen, (ii) a straight or branched alkyl group having 1 to 6 carbon atoms which may be substituted with 1 to 4 substituents selected from the group consisting of halogen, nitro, amino, mono- or dialkylamino of which alkyl moiety has 1 to 6 carbon atoms, 4 to 7 membered cyclic amino, straight or branched alkoxy having 1 to 6 carbon atoms, aryloxy having 6 to 10 carbon atoms, carbamoyl, cyano, hydroxy, carboxy, alkoxycarbonyl of which alkoxy moiety has 1 to 6 carbon atoms and mono- or dialkylcarbamoyl of which alkyl moiety has 1 to 6 carbon atoms, (iii) a straight or branched alkenyl group having 2 to 6 carbon atoms which may be substituted with 1 to 4 substituents selected from the group consisting of halogen, nitro, amino, mono- or dialkylamino or which alkyl moiety has 1 to 6 carbon atoms, 4 to 7 membered cyclic amino, straight or branched alkoxy having 1 to 6 carbon atoms, aryloxy having 6 to 10 carbon atoms, carbamoyl, cyano, hydroxy, carboxy, alkoxycarbonyl of which alkoxy moiety has 1 to 6 carbon atoms and mono- or dialkylcarbamoyl of which alkyl moiety has 1 to 6 carbon atoms, (iv) a phenylalkyl group of which alkyl moiety has 1 to 6 carbon atoms, and of which phenyl moiety may be substituted with 1 to 4 substituents selected from the group consisting of halogen, straight or branched alkyl having 1 to 6 carbon atoms, straight or branched alkenyl having 2 to 6 carbon atoms, straight or branched alkoxy having 1 to 6 carbon atoms, nitro, cyano, hydroxy, alkoxycarbonyl of which alkoxy moiety has 1 to 6 carbon atoms and mono- or dialkylcarbamoyl of which alkyl moiety has 1 to 6 carbon atoms, (v) a naphthylalkyl group of which alkyl moiety has 1 to 6 carbon atoms, and of which naphthyl moiety may be substituted with 1 to 4 substituents selected from the group consisting of halogen, straight or branched alkyl having 1 to 6 carbon atoms, straight or branched alkenyl having 2 to 6 carbon atoms, straight or branched alkoxy having 1 to 6 carbon atoms, nitro, cyano, hydroxy, alkoxycarbonyl of which alkoxy moiety has 1 to 6 carbon atoms and mono- or dialkylcarbamoyl of which alkyl moiety has 1 to 6 carbon atoms, or (vi) an aryl group having 4 to 24 carbon atoms which may be substituted with 1 to 4 substituents selected from the group consisting of halogen, straight or branched alkyl having to 1 to carbon atoms, straight or branched alkenyl having 2 to 6 carbon atoms, straight or branched alkoxy having 1 to 6 carbon atoms, nitro, cyano, oxo, hydroxy, amino, alkoxycarbonyl of which alkoxy moiety has 1 to 6 carbon atoms, carbamoyl and mono- or dialkylcarbamoyl of which alkyl moiety has 1 to 6 carbon atoms, or $R^{14}$ and $R^{15}$ together with the adjacent nitrogen form a 3 to 8 membered monocyclic heterocyclic group, condensed bicyclic or bridged bicyclic heterocyclic group or a condensed tricyclic heterocyclic group, and $R^{16}$ and $R^{17}$ are (i) a straight or branched alkyl group having 1 to 6 carbon atoms which may be substituted with 1 to 4 substituents selected from the group consisting of halogen, nitro, amino, mono- or dialkylamino of which alkyl moiety has 1 to 6 carbon atoms, 4 to 7 membered cyclic amino, straight or branched alkoxy having 1 to 6 carbon atoms, aryloxy having 6 to 10 carbon atoms, carbamoyl, cyano, hydroxy, carboxy, alkoxycarbonyl of which alkoxy moiety has 1 to 6 carbon atoms and mono- or dialkylcarbamoyl of which alkyl moiety has 1 to 6 carbon atoms, (ii) a straight or branched alkenyl group having 2 to 6 carbon atoms which may be substituted with 1 to 4 substituents selected from the group consisting of halogen, nitro, amino, mono- or dialkylamino or which alkyl moiety has 1 to 6 carbon atoms, 4 to 7 membered cyclic amino, straight or branched alkoxy having 1 to 6 carbon atoms, aryloxy having 6 to 10 carbon atoms, carbamoyl, cyano, hydroxy, carboxy, alkoxycarbonyl of which alkoxy moiety has 1 to 6 carbon atoms and mono- or dialkylcarbamoyl of which alkyl moiety has 1 to 6 carbon atoms, (iii) a phenylalkyl group of which alkyl moiety has 1 to 6 carbon atoms, and of which phenyl moiety may be substituted with 1 to 4 substituents selected from the group consisting of halogen, straight or branched alkyl having 1 to 6 carbon atoms, straight or branched alkenyl having 2 to 6 carbon atoms, straight or branched alkoxy having 1 to 6 carbon atoms, nitro, cyano, hydroxy, alkoxycarbonyl of which alkoxy moiety has 1 to 6 carbon atoms and mono- or dialkylcarbamoyl of which alkyl moiety has 1 to 6 carbon atoms, (iv) a naphthylalkyl group of which alkyl moiety has 1 to 6 carbon atoms, and of which naphthyl moiety may be substituted with 1 to 4 substituents selected from the group consisting of halogen, straight or branched alkyl having 1 to 6 carbon atoms, straight or branched alkenyl having 2 to 6 carbon atoms, straight or branched alkoxy having 1 to 6 carbon atoms, nitro, cyano, hydroxy, alkoxycarbonyl of which alkoxy moiety has 1 to 6 carbon atoms and mono- or dialkylcarbamoyl of which alkyl moiety has 1 to 6 carbon atoms, or (v) an aryl group having 4 to 24 carbon atoms which may be substituted with 1 to 4 substituents selected from the group consisting of halogen, straight or branched alkyl having to 1 to carbon atoms, straight or branched alkenyl having 2 to 6 carbon atoms, straight or branched alkoxy having 1 to 6 carbon atoms, nitro, cyano, oxo, hydroxy, amino, alkoxycarbonyl or which alkoxy moiety has 1 to 6 carbon atoms, carbamoyl and mono- or dialkylcarbamoyl of which alkyl moiety has 1 to 6 carbon atoms, or (h) dimethylamino (i) hydrogen, (j) halogen, (k) a nitro group, (l) a nitroso group, (m) a lower alkoxycarbonyl group, or (n) a lower alkylcarbamoyl group;

or a salt or solvate thereof.

2. A compound according to claim 1, wherein each of $R^1$ and $R^2$ is independently $C_{1-6}$ alkyl, phenyl-$C_{1-6}$ alkyl, naphthyl-$C_{1-6}$ alkyl or $C_{4-24}$ aryl, which may have 1 to 4 substituents;

$R^3$ is $C_{1-6}$ alkyl phenyl-$C_{1-6}$ alkyl or naphthyl-$C_{1-6}$ alkyl, which may have 1 to 4 substituents;

A is a group of the formula:

$$-(\underset{R^5}{\overset{R^4}{C}})_l-(\underset{R^7}{\overset{R^6}{C}})_m-(\underset{R^9}{\overset{R^8}{C}})_n-$$

wherein l, m and n are integers of 0 to 5, respectively; and each of $R^4$, $R^5$, $R^6$, $R^7$, $R^8$ and $R^9$ is independently (1) hydrogen, or (2) $C_{1-6}$ alkyl, $C_{2-6}$ alkenyl, phenyl-$C_{1-6}$ alkyl, naphthyl-$C_{1-6}$ alkyl or $C_{4-24}$ aryl, or $R^4$ and $R^5$ or $R^6$ and $R^7$ or $R^8$ and $R^9$ may bind to each other to form a ring, or $R^4$ or $R^6$ may bind to $R^8$ or $R^9$, respectively, to form a ring, —$CH_2CH_2OCH_2CH_2$— or a group of the formula:

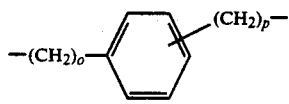

wherein o and p are integers of 0 to 5;
$B^1$ is a group of the formula:

$$-NR^{10'}R^{11'}$$

wherein $R^{10'}$ is (1) hydrogen, (2) $C_{1-30}$ straight or branched alkyl, $C_{3-8}$ cycloalkyl, saturated bi- or tricyclic hydrocarbon group formed by fusing 5 to 8 membered rings, phenyl $C_{1-6}$ alkyl, naphthyl $C_{1-6}$ alkyl or $C_{4-24}$ aryl, each of which may have 1 to 4 substituents, or (3) $-CO-R_{12}$, $-SO_2R^{13}$, $-CONR^{14}R^{15}$ or $-CS-NR^{14}R^{15}$; and
$R^{11'}$ is $-CO-R^{16}$, $-SO_2R^{17}$, $-CO-NR^{14}R^{15}$ or $-CS-NR^{14}R^{15}$;
wherein $R^{12}$, $R^{14}$ and $R^{15}$ are independently (1) hydrogen, or (2) $C_{1-30}$ straight or branched alkyl, $C_{3-8}$ cycloalkyl, saturated bi- or tricyclic hydrocarbon group formed by fusing 5 to 8 membered rings, $C_{2-30}$ alkenyl, phenyl-$C_{1-6}$ alkyl, naphthyl-$C_{1-6}$ alkyl or $C_{4-24}$ aryl,
$R^{13}$, $R^{16}$ and $R^{17}$ are independently $C_{1-30}$ straight or branched alkyl, $C_{3-8}$ cycloalkyl, saturated bi- or tricyclic hydrocarbon group formed by fusing 5 to 8 membered rings, $C_{2-30}$ alkenyl, phenyl-$C_{1-6}$ alkyl, naphthyl-$C_{1-6}$ alkyl or $C_{4-24}$ aryl,
said substituent of $C_{1-6}$ alkyl is halogen, nitro, amino, N-mono $C_{1-6}$ alkylamino, N,N-di $C_{1-6}$ alkylamino, 4 to 7 membered cyclic amino, $C_{1-6}$ alkoxy, $C_{6-10}$ aryloxy, carbamoyl, cyano, hydroxy, carboxy, $C_{1-6}$ alkoxycarbonyl or $C_{1-6}$ alkylcarbonyl;
said substituent of phenyl-$C_{1-6}$ alkyl or naphthyl-$C_{1-6}$ alkyl is halogen, $C_{1-6}$ alkyl, $C_{1-6}$ alkoxy, nitro, cyano, hydroxy, $C_{1-6}$ alkoxycarbonyl, carbamoyl or $C_{1-6}$ alkylcarbamoyl;
said substituent of $C_{4-24}$ aryl is halogen, $C_{1-6}$ alkyl, $C_{1-6}$ alkoxy, nitro, cyano, oxo, hydroxy, amino, $C_{1-6}$ alkoxycarbonyl, carbamoyl, or $C_{1-6}$ alkylcarbamoyl; and the lower alkyoxycarbonyl and lower alkylcarbamoyl of $R^1$ and $R^2$ are $C_{1-6}$ alkoxycarbonyl and $C_{1-6}$ alkylcarbamoyl, respectively.

3. A compound according to claim 1, wherein $B^1$ is $-NH-SO_2R^{17}$ wherein $R^{17}$ is $C_{1-30}$ straight or branched alkyl, $C_{3-8}$ cycloalkyl, saturated bi- or tricyclic hydrocarbon group formed by fusing 5 to 8 membered rings, $C_{2-30}$ alkenyl, phenyl-$C_{1-6}$ alkyl, naphthyl-$C_{1-6}$ alkyl or $C_{4-24}$ aryl.

4. A compound according to claim 1, wherein X is S or O, and $B^1$ is $-NH-SO_2R^{17}$ wherein $R^{17}$ is $C_{1-30}$ straight or branched alkyl, $C_{3-8}$ cycloalkyl, saturated bi- or tricyclic hydrocarbon group formed by fusing 5 to 8 membered rings, $C_{2-30}$ alkenyl, phenyl-$C_{1-6}$ alkyl, naphthyl-$C_{1-6}$ alkyl or $C_{4-24}$ aryl.

5. A compound according to claim 1 which is
5-[2-(methylsulfonylamino)ethylthio]imidazo[1,2-a]pyridine,
5-[2-(trifluoromethylsulfonylamino)ethylthio]imidazo[1,2-a]pyridine,
5-[3-(methylsulfonylamino)propyloxy]imidazo[1,2-a]pyridine,
5-[3-(trifluoromethylsulfonylamino)propoyloxy]imidazo[1,2-a]pyridine,
5-[3-(methylsulfonylamino)propylthio]imidazo[1,2-a]pyridine, or
5-[3-(trifluoromethylsulfonylamino)propylthio]imidazo[1,2-a]pyridine.

6. A calmodulin inhibitory composition comprising a compound of the formula (I') as defined in claim 1 or a pharmaceutically acceptable salt or solvate thereof, and a pharmaceutically acceptable carrier, diluent or excipient.

7. A method for inhibiting calmodulin comprising administering an effective amount of a compound of the formula (I') as defined in claim 1, or a pharmaceutically acceptable salt or solvate thereof optionally together with a pharmaceutically acceptable carrier, diluent or excipient to a patient requiring such inhibition.

* * * * *